US006630313B2

(12) United States Patent
Fadok et al.

(10) Patent No.: US 6,630,313 B2
(45) Date of Patent: Oct. 7, 2003

(54) PHOSPHATIDYL SERINE RECEPTORS AND USES THEREOF

(75) Inventors: Valerie A. Fadok, Denver, CO (US); Peter M. Henson, Denver, CO (US)

(73) Assignee: National Jewish Medical and Research Center, Denver, CO (US)

( * ) Notice: Subject to any disclaimer, the term of this patent is extended or adjusted under 35 U.S.C. 154(b) by 20 days.

(21) Appl. No.: 09/802,213

(22) Filed: Mar. 8, 2001

(65) Prior Publication Data

US 2001/0049122 A1 Dec. 6, 2001

Related U.S. Application Data

(60) Provisional application No. 60/188,930, filed on Mar. 8, 2000.

(51) Int. Cl.[7] .................. G01N 33/566; C07K 14/705; A61K 38/17
(52) U.S. Cl. .................. 435/7.1; 435/7.2; 514/2; 514/12; 530/300; 530/350
(58) Field of Search ................ 530/300, 350; 514/2, 12; 435/7.1, 7.2

(56) References Cited

FOREIGN PATENT DOCUMENTS

WO          WO 98/57985       12/1998

OTHER PUBLICATIONS

Promega Catalogue (2000) p 12.11.*
J. Skolnick, J.S. Fetrow (2000) From genes to protein structure and function:novel applications of computational approaches in the genomic era; Trends in Biotechnology 18(1): 34–39.*
NCBI Accession No. AB011157 (1998).
Fadok et al., *J. Clin. Invest.*, 101(4):890–898 (1996).
Fadok et al., *J. Immunol.*, 161:6250–6257 (1998).
Ishikawa et al., *DNA Research*, 4:307–313 (1997).
Nagase et al., *DNA Research*, 4:141–150 (1997).
Nagase et al., *DNA Research*, 5:31–39 (1998).
Ohara et al., *DNA Research*, 4:53–59 (1997).

* cited by examiner

Primary Examiner—Gary Kunz
Assistant Examiner—Stephen Gucker
(74) Attorney, Agent, or Firm—Sheridan Ross P.C.

(57) ABSTRACT

Disclosed are phosphatidylserine (PS) receptors, including PS receptors from human, mouse, *Drosophila melanogaster* and *Caenorhabditis elegans*. Also disclosed are homologues of such receptors, nucleic acids encoding such receptors and homologues thereof, as well as agonist and antagonist compounds that specifically associate with and affect the activation state of such receptors. Preferred agonists and antagonists of PS receptors according to the invention include antibodies, antibody fragments and binding partners that selectively bind to such a receptor. Also disclosed are methods of making and using the PS receptors, homologues thereof, and agonist and antagonist compounds of such receptors. In particular, methods for reducing inflammation, for treating an autoimmune disease, for enhancing transplantation of tissue grafts, methods of increasing anti-tumor immunity, and methods for inhibiting viral and parasitic infections are described.

24 Claims, 15 Drawing Sheets

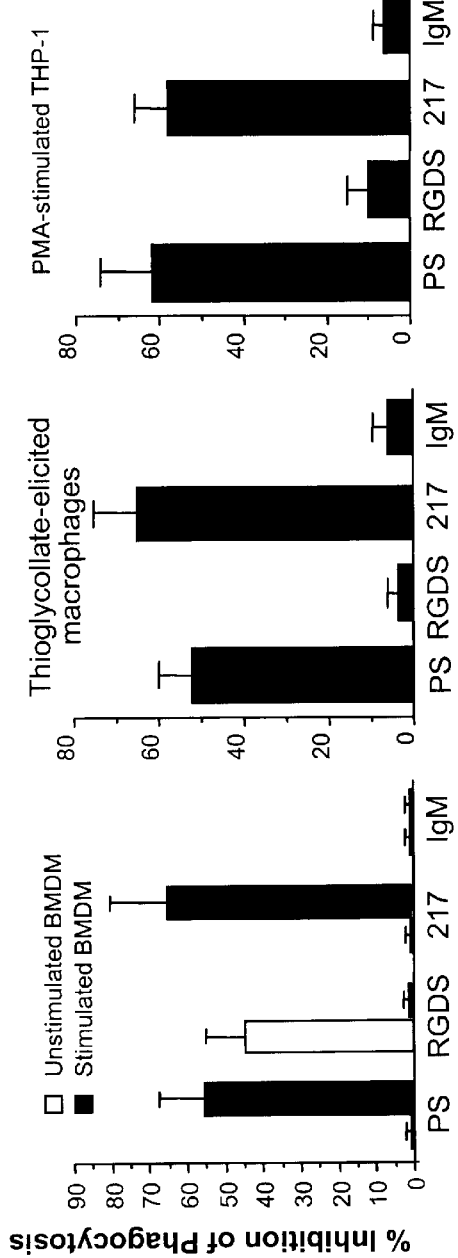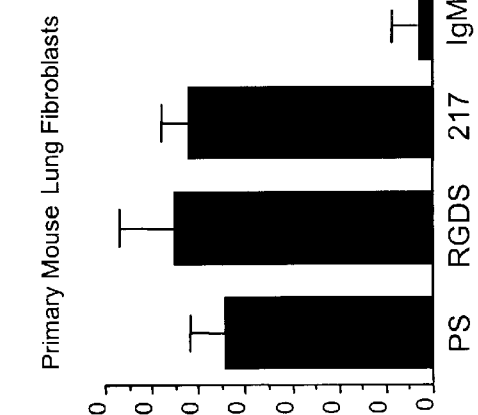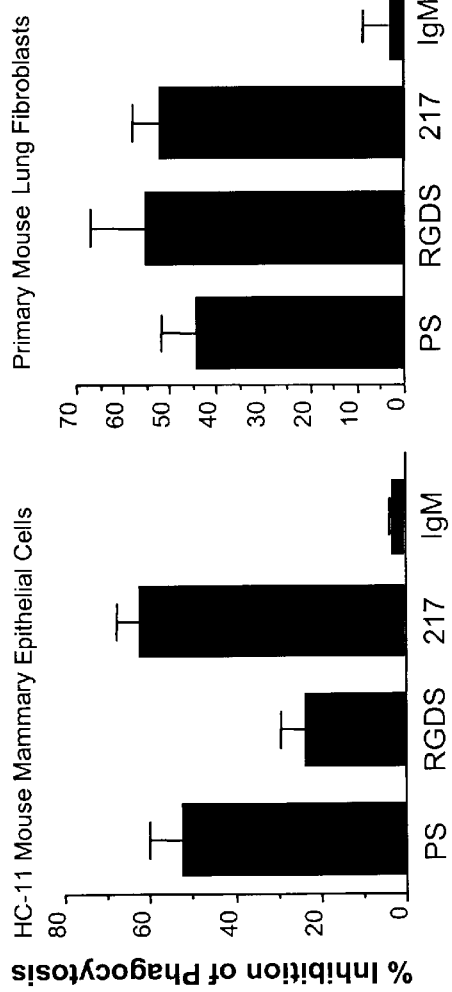

SEQUENCE LISTING

<160> NUMBER OF SEQ ID NOS: 11

<210> SEQ ID NO 1
<211> LENGTH: 1674
<212> TYPE: DNA
<213> ORGANISM: Homo sapiens

<400> SEQUENCE: 1
aagcttggca cgagggtgtc aggaagcggg ctgcgccgag gtcgtagcgg aaccagctgg     60

-continued

```
cgaccccgca gaatgaacca caagagcaag aagcgcatcc gcgaggccaa gcggagtgcg      120
cggccggagc tcaaggactc gctggattgg acccggcaca actactacga gagcttctcg      180
ctgagcccgg cggccgtggc ggataacgtg gaaagggcag atgctttaca gctgtctgtg      240
gaagaatttg tggagcggta tgaaagacct tacaagcccg tggttttgtt gaatgcgcaa      300
gagggctggt ctgcgcagga gaatggact ctggagcgcc taaaaaggaa atatcggaac       360
cagaagttca gtgtggtga ggataacgat ggctactcag tgaagatgaa gatgaaatac       420
tacatcgagt acatggagag cactcgagat gatagtcccc tttacatctt tgacagcagc      480
tatggtgaac ccctaaaag aaggaaactt ttggaagact acaaggtgcc aaagtttttc       540
actgatgacc ttttccagta tgctggggag aagcgcaggc ccccttacag gtggtttgtg      600
atggggccac cacgctccgg aactgggatt cacatcgacc ctctgggaac cagtgcctgg      660
aatgccttag ttcagggcca caagcgctgg tgcctgtttc ctaccagcac tcccagggaa      720
ctcatcaaag tgacccgaga cgaaggaggg aaccagcaag acgaagctat tacctggttt      780
aatgttattt atccccggac acagcttcca acctggccac tgaattcaa accctggaa       840 atcttacaaa aaccaggaga gactgtcttt gtaccaggag gctggtggca tgttgtcctc     900
aatctcgaca ctactatcgc catcacccaa aattttgcca gcagcaccaa cttccctgtg     960
gtatggcaca agacggtaag agggagacca agttatcaa ggaaatggta taggattttg     1020
aagcaagagc accccgagtt ggcagtcctc gcagactcgg ttgaccttca ggagtccaca    1080
gggatagctt ccgacagctc cagcgactct tccagctcct ccagctccag ttcgtcagac    1140
tccgactcag agtgcgagtc tggatccgag ggcgatggga cagtgcaccg caggaagaag    1200
aggaggacgt gcagcatggt gggaaacggg gacaccacct cccaggacga ctgtgtcagc    1260
aaagagcgca gctcctccag gattagggac acttgtggag gccgggctca cccctgagca    1320
aagagcgcag cttcttcagg tggacccaac aaggttgttg tctgtatggg aaggacacgc    1380
tcccggcaag gggaagggcc tggggggggg gggcttgtca agtccttcac acaaagggga    1440
gggcttgaca agagcccaag aatgagggac accccttggg accgggaacc ccattacctt    1500
aggggtttgg ttccatagct tttcccttt gctaccaaat gcagattaaa ccccgggttg    1560
gttttacctc aggcaagaaa aatggggaat aggggcccaa aaaaaatcct tttaccattt   1620
tttaataaaa aatagaatcc ctaaaaaaaa aaaaaaaaa aaaaagcgg ccgc            1674
```

<210> SEQ ID NO 2
<211> LENGTH: 1245
<212> TYPE: DNA
<213> ORGANISM: Homo sapiens
<220> FEATURE:
<221> NAME/KEY: CDS
<222> LOCATION: (1)..(1245)

<400> SEQUENCE: 2

```
atg aac cac aag agc aag aag cgc atc cgc gag gcc aag cgg agt gcg      48
Met Asn His Lys Ser Lys Lys Arg Ile Arg Glu Ala Lys Arg Ser Ala
1               5                   10                  15 cgg ccg gag ctc aag gac tcg ctg gat tgg acc cgg cac aac tac tac      96
Arg Pro Glu Leu Lys Asp Ser Leu Asp Trp Thr Arg His Asn Tyr Tyr
            20                  25                  30 gag agc ttc tcg ctg agc ccg gcg gcc gtg gcg gat aac gtg gaa agg     144
Glu Ser Phe Ser Leu Ser Pro Ala Ala Val Ala Asp Asn Val Glu Arg
        35                  40                  45 gca gat gct tta cag ctg tct gtg gaa gaa ttt gtg gag cgg tat gaa     192
Ala Asp Ala Leu Gln Leu Ser Val Glu Glu Phe Val Glu Arg Tyr Glu
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     | 50  |     |     |     |     | 55  |     |     |     |     |     | 60  |     |     |     |     |
| aga | cct | tac | aag | ccc | gtg | gtt | ttg | ttg | aat | gcg | caa | gag | ggc | tgg | tct | 240 |
| Arg | Pro | Tyr | Lys | Pro | Val | Val | Leu | Leu | Asn | Ala | Gln | Glu | Gly | Trp | Ser |     |
| 65  |     |     |     | 70  |     |     |     |     | 75  |     |     |     |     | 80  |     |     |
| gcg | cag | gag | aaa | tgg | act | ctg | gag | cgc | cta | aaa | agg | aaa | tat | cgg | aac | 288 |
| Ala | Gln | Glu | Lys | Trp | Thr | Leu | Glu | Arg | Leu | Lys | Arg | Lys | Tyr | Arg | Asn |     |
|     |     |     |     |     | 85  |     |     |     |     | 90  |     |     |     |     | 95  |     |
| cag | aag | ttc | aag | tgt | ggt | gag | gat | aac | gat | ggc | tac | tca | gtg | aag | atg | 336 |
| Gln | Lys | Phe | Lys | Cys | Gly | Glu | Asp | Asn | Asp | Gly | Tyr | Ser | Val | Lys | Met |     |
|     |     |     |     | 100 |     |     |     |     | 105 |     |     |     |     | 110 |     |     |
| aag | atg | aaa | tac | tac | atc | gag | tac | atg | gag | agc | act | cga | gat | gat | agt | 384 |
| Lys | Met | Lys | Tyr | Tyr | Ile | Glu | Tyr | Met | Glu | Ser | Thr | Arg | Asp | Asp | Ser |     |
|     |     |     | 115 |     |     |     |     | 120 |     |     |     |     | 125 |     |     |     |
| ccc | ctt | tac | atc | ttt | gac | agc | agc | tat | ggt | gaa | cac | cct | aaa | aga | agg | 432 |
| Pro | Leu | Tyr | Ile | Phe | Asp | Ser | Ser | Tyr | Gly | Glu | His | Pro | Lys | Arg | Arg |     |
|     | 130 |     |     |     |     | 135 |     |     |     |     | 140 |     |     |     |     |     |
| aaa | ctt | ttg | gaa | gac | tac | aag | gtg | cca | aag | ttt | ttc | act | gat | gac | ctt | 480 |
| Lys | Leu | Leu | Glu | Asp | Tyr | Lys | Val | Pro | Lys | Phe | Phe | Thr | Asp | Asp | Leu |     |
| 145 |     |     |     |     | 150 |     |     |     |     | 155 |     |     |     |     | 160 |     |
| ttc | cag | tat | gct | ggg | gag | aag | cgc | agg | ccc | cct | tac | agg | tgg | ttt | gtg | 528 |
| Phe | Gln | Tyr | Ala | Gly | Glu | Lys | Arg | Arg | Pro | Pro | Tyr | Arg | Trp | Phe | Val |     |
|     |     |     |     | 165 |     |     |     |     | 170 |     |     |     |     | 175 |     |     |
| atg | ggg | cca | cca | cgc | tcc | gga | act | ggg | att | cac | atc | gac | cct | ctg | gga | 576 |
| Met | Gly | Pro | Pro | Arg | Ser | Gly | Thr | Gly | Ile | His | Ile | Asp | Pro | Leu | Gly |     |
|     |     |     | 180 |     |     |     |     | 185 |     |     |     |     | 190 |     |     |     |
| acc | agt | gcc | tgg | aat | gcc | tta | gtt | cag | ggc | cac | aag | cgc | tgg | tgc | ctg | 624 |
| Thr | Ser | Ala | Trp | Asn | Ala | Leu | Val | Gln | Gly | His | Lys | Arg | Trp | Cys | Leu |     |
|     | 195 |     |     |     |     | 200 |     |     |     |     | 205 |     |     |     |     |     |
| ttt | cct | acc | agc | act | ccc | agg | gaa | ctc | atc | aaa | gtg | acc | cga | gac | gaa | 672 |
| Phe | Pro | Thr | Ser | Thr | Pro | Arg | Glu | Leu | Ile | Lys | Val | Thr | Arg | Asp | Glu |     |
| 210 |     |     |     |     | 215 |     |     |     |     | 220 |     |     |     |     |     |     |
| gga | ggg | aac | cag | caa | gac | gaa | gct | att | acc | tgg | ttt | aat | gtt | att | tat | 720 |
| Gly | Gly | Asn | Gln | Gln | Asp | Glu | Ala | Ile | Thr | Trp | Phe | Asn | Val | Ile | Tyr |     |
| 225 |     |     |     |     | 230 |     |     |     |     | 235 |     |     |     |     | 240 |     |
| ccc | cgg | aca | cag | ctt | cca | acc | tgg | cca | cct | gaa | ttc | aaa | ccc | ctg | gaa | 768 |
| Pro | Arg | Thr | Gln | Leu | Pro | Thr | Trp | Pro | Pro | Glu | Phe | Lys | Pro | Leu | Glu |     |
|     |     |     |     | 245 |     |     |     |     | 250 |     |     |     |     | 255 |     |     |
| atc | tta | caa | aaa | cca | gga | gag | act | gtc | ttt | gta | cca | gga | ggc | tgg | tgg | 816 |
| Ile | Leu | Gln | Lys | Pro | Gly | Glu | Thr | Val | Phe | Val | Pro | Gly | Gly | Trp | Trp |     |
|     |     |     | 260 |     |     |     |     | 265 |     |     |     |     | 270 |     |     |     |
| cat | gtt | gtc | ctc | aat | ctc | gac | act | act | atc | gcc | atc | acc | caa | aat | ttt | 864 |
| His | Val | Val | Leu | Asn | Leu | Asp | Thr | Thr | Ile | Ala | Ile | Thr | Gln | Asn | Phe |     |
|     | 275 |     |     |     |     | 280 |     |     |     |     | 285 |     |     |     |     |     |
| gcc | agc | agc | acc | aac | ttc | cct | gtg | gta | tgg | cac | aag | acg | gta | aga | ggg | 912 |
| Ala | Ser | Ser | Thr | Asn | Phe | Pro | Val | Val | Trp | His | Lys | Thr | Val | Arg | Gly |     |
| 290 |     |     |     |     | 295 |     |     |     |     | 300 |     |     |     |     |     |     |
| aga | cca | aag | tta | tca | agg | aaa | tgg | tat | agg | att | ttg | aag | caa | gag | cac | 960 |
| Arg | Pro | Lys | Leu | Ser | Arg | Lys | Trp | Tyr | Arg | Ile | Leu | Lys | Gln | Glu | His |     |
| 305 |     |     |     |     | 310 |     |     |     |     | 315 |     |     |     |     | 320 |     |
| ccc | gag | ttg | gca | gtc | ctc | gca | gac | tcg | gtt | gac | ctt | cag | gag | tcc | aca | 1008 |
| Pro | Glu | Leu | Ala | Val | Leu | Ala | Asp | Ser | Val | Asp | Leu | Gln | Glu | Ser | Thr |     |
|     |     |     |     | 325 |     |     |     |     | 330 |     |     |     |     | 335 |     |     |
| ggg | ata | gct | tcc | gac | agc | tcc | agc | gac | tct | tcc | agc | tcc | tcc | agc | tcc | 1056 |
| Gly | Ile | Ala | Ser | Asp | Ser | Ser | Ser | Asp | Ser | Ser | Ser | Ser | Ser | Ser | Ser |     |
|     |     |     | 340 |     |     |     |     | 345 |     |     |     |     | 350 |     |     |     |
| agt | tcg | tca | gac | tcc | gac | tca | gag | tgc | gag | tct | gga | tcc | gag | ggc | gat | 1104 |
| Ser | Ser | Ser | Asp | Ser | Asp | Ser | Glu | Cys | Glu | Ser | Gly | Ser | Glu | Gly | Asp |     |
|     |     | 355 |     |     |     |     | 360 |     |     |     |     | 365 |     |     |     |     |
| ggg | aca | gtg | cac | cgc | agg | aag | aag | agg | agg | acg | tgc | agc | atg | gtg | gga | 1152 |

```
Gly Thr Val His Arg Arg Lys Lys Arg Arg Thr Cys Ser Met Val Gly
    370                 375                 380 aac ggg gac acc acc tcc cag gac gac tgt gtc agc aaa gag cgc agc      1200
Asn Gly Asp Thr Thr Ser Gln Asp Asp Cys Val Ser Lys Glu Arg Ser
385                 390                 395                 400 tcc tcc agg att agg gac act tgt gga ggc cgg gct cac ccc tga          1245
Ser Ser Arg Ile Arg Asp Thr Cys Gly Gly Arg Ala His Pro
                405                 410

<210> SEQ ID NO 3
<211> LENGTH: 414
<212> TYPE: PRT
<213> ORGANISM: Homo sapiens

<400> SEQUENCE: 3

Met Asn His Lys Ser Lys Lys Arg Ile Arg Glu Ala Lys Arg Ser Ala
1               5                   10                  15

Arg Pro Glu Leu Lys Asp Ser Leu Asp Trp Thr Arg His Asn Tyr Tyr
                20                  25                  30

Glu Ser Phe Ser Leu Ser Pro Ala Ala Val Ala Asp Asn Val Glu Arg
            35                  40                  45

Ala Asp Ala Leu Gln Leu Ser Val Glu Glu Phe Val Glu Arg Tyr Glu
50                  55                  60

Arg Pro Tyr Lys Pro Val Val Leu Leu Asn Ala Gln Glu Gly Trp Ser
65                  70                  75                  80

Ala Gln Glu Lys Trp Thr Leu Glu Arg Leu Lys Arg Lys Tyr Arg Asn
                85                  90                  95

Gln Lys Phe Lys Cys Gly Glu Asp Asn Asp Gly Tyr Ser Val Lys Met
            100                 105                 110

Lys Met Lys Tyr Tyr Ile Glu Tyr Met Glu Ser Thr Arg Asp Asp Ser
        115                 120                 125

Pro Leu Tyr Ile Phe Asp Ser Ser Tyr Gly Glu His Pro Lys Arg Arg
130                 135                 140

Lys Leu Leu Glu Asp Tyr Lys Val Pro Lys Phe Phe Thr Asp Asp Leu
145                 150                 155                 160

Phe Gln Tyr Ala Gly Glu Lys Arg Arg Pro Tyr Arg Trp Phe Val
                165                 170                 175

Met Gly Pro Pro Arg Ser Gly Thr Gly Ile His Ile Asp Pro Leu Gly
            180                 185                 190

Thr Ser Ala Trp Asn Ala Leu Val Gln Gly His Lys Arg Trp Cys Leu
        195                 200                 205

Phe Pro Thr Ser Thr Pro Arg Glu Leu Ile Lys Val Thr Arg Asp Glu
210                 215                 220

Gly Gly Asn Gln Gln Asp Glu Ala Ile Thr Trp Phe Asn Val Ile Tyr
225                 230                 235                 240

Pro Arg Thr Gln Leu Pro Thr Trp Pro Pro Glu Phe Lys Pro Leu Glu
                245                 250                 255

Ile Leu Gln Lys Pro Gly Glu Thr Val Phe Val Pro Gly Gly Trp Trp
            260                 265                 270

His Val Val Leu Asn Leu Asp Thr Thr Ile Ala Ile Thr Gln Asn Phe
        275                 280                 285

Ala Ser Ser Thr Asn Phe Pro Val Val Trp His Lys Thr Val Arg Gly
290                 295                 300

Arg Pro Lys Leu Ser Arg Lys Trp Tyr Arg Ile Leu Lys Gln Glu His
305                 310                 315                 320
```

```
Pro Glu Leu Ala Val Leu Ala Asp Ser Val Asp Leu Gln Glu Ser Thr
            325                 330                 335
Gly Ile Ala Ser Asp Ser Ser Asp Ser Ser Ser Ser Ser Ser
            340                 345                 350
Ser Ser Ser Asp Ser Asp Ser Glu Cys Glu Ser Gly Ser Glu Gly Asp
            355                 360                 365
Gly Thr Val His Arg Arg Lys Lys Arg Arg Thr Cys Ser Met Val Gly
    370                 375                 380
Asn Gly Asp Thr Thr Ser Gln Asp Asp Cys Val Ser Lys Glu Arg Ser
385                 390                 395                 400
Ser Ser Arg Ile Arg Asp Thr Cys Gly Gly Arg Ala His Pro
                405                 410

<210> SEQ ID NO 4
<211> LENGTH: 1212
<212> TYPE: DNA
<213> ORGANISM: Mus musculus
<220> FEATURE:
<221> NAME/KEY: CDS
<222> LOCATION: (1)..(1212)

<400> SEQUENCE: 4
```

| | | | | | | | | | | | | | | | | |
|---|---|---|---|---|---|---|---|---|---|---|---|---|---|---|---|---|
| atg | aac | cac | aag | agc | aag | aag | cgc | atc | cgc | gag | gcc | aag | cga | agt | gcg | 48 |
| Met | Asn | His | Lys | Ser | Lys | Lys | Arg | Ile | Arg | Glu | Ala | Lys | Arg | Ser | Ala | |
| 1 | | | | 5 | | | | | 10 | | | | | 15 | | |
| cgg | ccg | gag | ctc | aag | gac | tcg | ctc | gac | tgg | acc | cgg | cac | aac | tac | tac | 96 |
| Arg | Pro | Glu | Leu | Lys | Asp | Ser | Leu | Asp | Trp | Thr | Arg | His | Asn | Tyr | Tyr | |
| | | | 20 | | | | | 25 | | | | | 30 | | | |
| gag | agc | tac | ccg | ctg | aac | ccc | gcg | gcc | gtg | tcg | gat | aac | gtg | gag | aga | 144 |
| Glu | Ser | Tyr | Pro | Leu | Asn | Pro | Ala | Ala | Val | Ser | Asp | Asn | Val | Glu | Arg | |
| | | 35 | | | | | 40 | | | | | 45 | | | | |
| gct | gat | gcc | tta | cag | ctg | tcg | gtg | aaa | gag | ttc | gtg | gag | cgc | tac | gag | 192 |
| Ala | Asp | Ala | Leu | Gln | Leu | Ser | Val | Lys | Glu | Phe | Val | Glu | Arg | Tyr | Glu | |
| | 50 | | | | | 55 | | | | | 60 | | | | | |
| agg | cct | tac | aag | ccc | gtg | gtt | ctg | ctc | aat | gca | caa | gag | ggc | tgg | tcc | 240 |
| Arg | Pro | Tyr | Lys | Pro | Val | Val | Leu | Leu | Asn | Ala | Gln | Glu | Gly | Trp | Ser | |
| 65 | | | | | 70 | | | | | 75 | | | | | 80 | |
| gca | cag | gag | aaa | tgg | act | ctg | gag | cgc | ctc | aaa | agg | aaa | tac | cgg | aac | 288 |
| Ala | Gln | Glu | Lys | Trp | Thr | Leu | Glu | Arg | Leu | Lys | Arg | Lys | Tyr | Arg | Asn | |
| | | | | 85 | | | | | 90 | | | | | 95 | | |
| cag | aag | ttc | aag | tgc | ggc | gag | gat | aat | gac | ggc | tac | tcg | gtg | aag | atg | 336 |
| Gln | Lys | Phe | Lys | Cys | Gly | Glu | Asp | Asn | Asp | Gly | Tyr | Ser | Val | Lys | Met | |
| | | | 100 | | | | | 105 | | | | | 110 | | | |
| aag | atg | aag | tac | tac | atc | gag | tac | atg | gag | agc | acc | cgc | gat | gac | agt | 384 |
| Lys | Met | Lys | Tyr | Tyr | Ile | Glu | Tyr | Met | Glu | Ser | Thr | Arg | Asp | Asp | Ser | |
| | | 115 | | | | | 120 | | | | | 125 | | | | |
| ccc | ctt | tac | atc | ttc | gat | agc | agc | tat | ggc | gaa | cac | ccc | aaa | aga | agg | 432 |
| Pro | Leu | Tyr | Ile | Phe | Asp | Ser | Ser | Tyr | Gly | Glu | His | Pro | Lys | Arg | Arg | |
| | 130 | | | | | 135 | | | | | 140 | | | | | |
| aaa | ctt | ttg | gaa | gac | tac | aag | gtg | ccc | aag | ttt | ttc | aca | gat | gat | ctt | 480 |
| Lys | Leu | Leu | Glu | Asp | Tyr | Lys | Val | Pro | Lys | Phe | Phe | Thr | Asp | Asp | Leu | |
| 145 | | | | | 150 | | | | | 155 | | | | | 160 | |
| ttc | caa | tac | gcg | ggg | gag | aaa | cgc | aga | ccc | cct | tac | agg | tgg | ttt | gtg | 528 |
| Phe | Gln | Tyr | Ala | Gly | Glu | Lys | Arg | Arg | Pro | Pro | Tyr | Arg | Trp | Phe | Val | |
| | | | | 165 | | | | | 170 | | | | | 175 | | |
| atg | ggg | cca | ccg | cgt | tct | gga | act | ggg | att | cac | atc | gac | cct | ctg | ggg | 576 |
| Met | Gly | Pro | Pro | Arg | Ser | Gly | Thr | Gly | Ile | His | Ile | Asp | Pro | Leu | Gly | |
| | | | 180 | | | | | 185 | | | | | 190 | | | |
| acc | agt | gcc | tgg | aat | gcc | tta | gtt | cag | ggt | cac | aag | cgg | tgg | tgc | ctc | 624 |
| Thr | Ser | Ala | Trp | Asn | Ala | Leu | Val | Gln | Gly | His | Lys | Arg | Trp | Cys | Leu | |

-continued

|  |  |  |  |  |  |  |  |  |  |  |  |  |  |  |  |
|---|---|---|---|---|---|---|---|---|---|---|---|---|---|---|---|
|  |  |  | 195 |  |  |  | 200 |  |  |  | 205 |  |  |  |  |
| ttc | cca | aca | aac | aca | ccc | aga | gaa | ctc | atc | aag | gtg | acc | cga | gaa | gaa | 672 |
| Phe | Pro | Thr | Asn | Thr | Pro | Arg | Glu | Leu | Ile | Lys | Val | Thr | Arg | Glu | Glu |  |
|  |  | 210 |  |  |  | 215 |  |  |  | 220 |  |  |  |  |  |  |
| gga | ggg | aac | caa | cag | gat | gaa | gca | att | acc | tgg | ttt | aat | gtc | atc | tat | 720 |
| Gly | Gly | Asn | Gln | Gln | Asp | Glu | Ala | Ile | Thr | Trp | Phe | Asn | Val | Ile | Tyr |  |
| 225 |  |  |  | 230 |  |  |  | 235 |  |  |  | 240 |  |  |  |  |
| ccc | cgg | aca | cag | ctt | cca | acc | tgg | cca | cct | gaa | ttc | aaa | ccc | ctg | gag | 768 |
| Pro | Arg | Thr | Gln | Leu | Pro | Thr | Trp | Pro | Pro | Glu | Phe | Lys | Pro | Leu | Glu |  |
|  |  |  |  | 245 |  |  |  | 250 |  |  |  | 255 |  |  |  |  |
| ata | tta | cag | aaa | cca | gga | gaa | act | gtc | ttt | gta | cca | ggg | ggc | tgg | tgg | 816 |
| Ile | Leu | Gln | Lys | Pro | Gly | Glu | Thr | Val | Phe | Val | Pro | Gly | Gly | Trp | Trp |  |
|  |  | 260 |  |  |  | 265 |  |  |  | 270 |  |  |  |  |  |  |
| cat | gtt | gtc | ctc | aac | ctt | gac | acc | acc | att | gcc | atc | acc | cag | aac | ttt | 864 |
| His | Val | Val | Leu | Asn | Leu | Asp | Thr | Thr | Ile | Ala | Ile | Thr | Gln | Asn | Phe |  |
|  |  | 275 |  |  |  | 280 |  |  |  | 285 |  |  |  |  |  |  |
| gcc | agc | agc | acc | aac | ttc | cct | gtt | gtg | tgg | cac | aag | acg | gta | aga | ggg | 912 |
| Ala | Ser | Ser | Thr | Asn | Phe | Pro | Val | Val | Trp | His | Lys | Thr | Val | Arg | Gly |  |
|  | 290 |  |  |  | 295 |  |  |  | 300 |  |  |  |  |  |  |  |
| aga | cca | aag | tta | tca | agg | aag | tgg | tat | agg | atc | ttg | aaa | cag | gag | cac | 960 |
| Arg | Pro | Lys | Leu | Ser | Arg | Lys | Trp | Tyr | Arg | Ile | Leu | Lys | Gln | Glu | His |  |
| 305 |  |  |  | 310 |  |  |  | 315 |  |  |  | 320 |  |  |  |  |
| cct | gag | ctg | gca | gtc | ctg | gcc | gac | gca | gtt | gac | ctc | cag | gag | tcc | aca | 1008 |
| Pro | Glu | Leu | Ala | Val | Leu | Ala | Asp | Ala | Val | Asp | Leu | Gln | Glu | Ser | Thr |  |
|  |  |  |  | 325 |  |  |  | 330 |  |  |  | 335 |  |  |  |  |
| ggc | att | gcc | tct | gac | agc | tcc | agc | gac | tct | tct | agc | tcc | tct | agt | tcc | 1056 |
| Gly | Ile | Ala | Ser | Asp | Ser | Ser | Ser | Asp | Ser | Ser | Ser | Ser | Ser | Ser | Ser |  |
|  |  |  | 340 |  |  |  | 345 |  |  |  | 350 |  |  |  |  |  |
| agc | tcg | tca | gac | tcg | gac | tca | gag | tgt | gaa | tct | ggg | tca | gaa | ggt | gat | 1104 |
| Ser | Ser | Ser | Asp | Ser | Asp | Ser | Glu | Cys | Glu | Ser | Gly | Ser | Glu | Gly | Asp |  |
|  |  | 355 |  |  |  | 360 |  |  |  | 365 |  |  |  |  |  |  |
| ggg | acg | aca | cac | cgc | agg | aag | aag | agg | aga | acc | tgc | agc | atg | gtg | gga | 1152 |
| Gly | Thr | Thr | His | Arg | Arg | Lys | Lys | Arg | Arg | Thr | Cys | Ser | Met | Val | Gly |  |
|  | 370 |  |  |  | 375 |  |  |  | 380 |  |  |  |  |  |  |  |
| aat | ggg | gac | act | acc | tcc | cag | gat | gac | tgt | gtg | agc | aaa | gag | cgc | agc | 1200 |
| Asn | Gly | Asp | Thr | Thr | Ser | Gln | Asp | Asp | Cys | Val | Ser | Lys | Glu | Arg | Ser |  |
| 385 |  |  |  | 390 |  |  |  | 395 |  |  |  | 400 |  |  |  |  |
| tcc | tcc | agg | tga |  |  |  |  |  |  |  |  |  |  |  |  | 1212 |
| Ser | Ser | Arg |  |  |  |  |  |  |  |  |  |  |  |  |  |  |

<210> SEQ ID NO 5
<211> LENGTH: 403
<212> TYPE: PRT
<213> ORGANISM: Mus musculus

<400> SEQUENCE: 5

Met Asn His Lys Ser Lys Lys Arg Ile Arg Glu Ala Lys Arg Ser Ala
1               5                   10                  15

Arg Pro Glu Leu Lys Asp Ser Leu Asp Trp Thr Arg His Asn Tyr Tyr
            20                  25                  30

Glu Ser Tyr Pro Leu Asn Pro Ala Ala Val Ser Asp Asn Val Glu Arg
        35                  40                  45

Ala Asp Ala Leu Gln Leu Ser Val Lys Glu Phe Val Glu Arg Tyr Glu
    50                  55                  60

Arg Pro Tyr Lys Pro Val Val Leu Leu Asn Ala Gln Glu Gly Trp Ser
65                  70                  75                  80

Ala Gln Glu Lys Trp Thr Leu Glu Arg Leu Lys Arg Lys Tyr Arg Asn
                85                  90                  95

```
Gln Lys Phe Lys Cys Gly Glu Asp Asn Asp Gly Tyr Ser Val Lys Met
        100                 105                 110
Lys Met Lys Tyr Tyr Ile Glu Tyr Met Glu Ser Thr Arg Asp Asp Ser
        115                 120                 125
Pro Leu Tyr Ile Phe Asp Ser Ser Tyr Gly Glu His Pro Lys Arg Arg
        130                 135                 140
Lys Leu Leu Glu Asp Tyr Lys Val Pro Lys Phe Phe Thr Asp Asp Leu
145                 150                 155                 160
Phe Gln Tyr Ala Gly Glu Lys Arg Arg Pro Pro Tyr Arg Trp Phe Val
                165                 170                 175
Met Gly Pro Pro Arg Ser Gly Thr Gly Ile His Ile Asp Pro Leu Gly
            180                 185                 190
Thr Ser Ala Trp Asn Ala Leu Val Gln Gly His Lys Arg Trp Cys Leu
        195                 200                 205
Phe Pro Thr Asn Thr Pro Arg Glu Leu Ile Lys Val Thr Arg Glu Glu
        210                 215                 220
Gly Gly Asn Gln Gln Asp Glu Ala Ile Thr Trp Phe Asn Val Ile Tyr
225                 230                 235                 240
Pro Arg Thr Gln Leu Pro Thr Trp Pro Pro Glu Phe Lys Pro Leu Glu
                245                 250                 255
Ile Leu Gln Lys Pro Gly Glu Thr Val Phe Val Pro Gly Gly Trp Trp
            260                 265                 270
His Val Val Leu Asn Leu Asp Thr Thr Ile Ala Ile Thr Gln Asn Phe
        275                 280                 285
Ala Ser Ser Thr Asn Phe Pro Val Val Trp His Lys Thr Val Arg Gly
        290                 295                 300
Arg Pro Lys Leu Ser Arg Lys Trp Tyr Arg Ile Leu Lys Gln Glu His
305                 310                 315                 320
Pro Glu Leu Ala Val Leu Ala Asp Ala Val Asp Leu Gln Glu Ser Thr
                325                 330                 335
Gly Ile Ala Ser Asp Ser Ser Asp Ser Ser Ser Ser Ser Ser
            340                 345                 350
Ser Ser Ser Asp Ser Asp Ser Glu Cys Glu Ser Gly Ser Glu Gly Asp
        355                 360                 365
Gly Thr Thr His Arg Arg Lys Lys Arg Arg Thr Cys Ser Met Val Gly
        370                 375                 380
Asn Gly Asp Thr Thr Ser Gln Asp Asp Cys Val Ser Lys Glu Arg Ser
385                 390                 395                 400
Ser Ser Arg

<210> SEQ ID NO 6
<211> LENGTH: 1050
<212> TYPE: DNA
<213> ORGANISM: Caenorhabditis elegans
<220> FEATURE:
<221> NAME/KEY: CDS
<222> LOCATION: (1)..(1050)

<400> SEQUENCE: 6 atg tca tta ggg cga gat aga tac tca tta ccg cgt act tat aaa cgg     48
Met Ser Leu Gly Arg Asp Arg Tyr Ser Leu Pro Arg Thr Tyr Lys Arg
1               5                   10                  15 gtt tca cat gcg aag gac aaa gcg aga ccg gag ctg aga aag ttc gga     96
Val Ser His Ala Lys Asp Lys Ala Arg Pro Glu Leu Arg Lys Phe Gly
                20                  25                  30 tgg gag act ctg gga tac tcg gaa agc ttt aat ctg cct cca ttt agg    144
```

```
Trp Glu Thr Leu Gly Tyr Ser Glu Ser Phe Asn Leu Pro Pro Phe Arg
         35                  40                  45 gat agt att caa aga gtt gat ggg aat aat ctt acc gtg gag gag ttc      192
Asp Ser Ile Gln Arg Val Asp Gly Asn Asn Leu Thr Val Glu Glu Phe
    50                  55                  60 cgc cga gat ttc gaa aga ccg aga atc cca gtt att atc act gga ttg      240
Arg Arg Asp Phe Glu Arg Pro Arg Ile Pro Val Ile Ile Thr Gly Leu
 65                  70                  75                  80 act gat aat tgg gca gct aaa gac aag tgg acg gtt gag aga cga aag      288
Thr Asp Asn Trp Ala Ala Lys Asp Lys Trp Thr Val Glu Arg Arg Lys
                 85                  90                  95 acg aaa aag tta tcg gaa gac tat tcg gtt cca aag ttc ttc gaa gac      336
Thr Lys Lys Leu Ser Glu Asp Tyr Ser Val Pro Lys Phe Phe Glu Asp
            100                 105                 110 gat ctc ttc cac tat gcg gat gat aag aag aga cct cca cat cga tgg      384
Asp Leu Phe His Tyr Ala Asp Asp Lys Lys Arg Pro Pro His Arg Trp
        115                 120                 125 ttt gtg atg gga cca gct cgt tct gga act gca att cac att gat cca      432
Phe Val Met Gly Pro Ala Arg Ser Gly Thr Ala Ile His Ile Asp Pro
    130                 135                 140 ctc ggg aca agt gca tgg aat tcg ttg ctt caa ggt cac aaa cga tgg      480
Leu Gly Thr Ser Ala Trp Asn Ser Leu Leu Gln Gly His Lys Arg Trp
145                 150                 155                 160 gtt ctg att cct ccg att gca cca cgt gat ctt gtg aaa ccg atg gct      528
Val Leu Ile Pro Pro Ile Ala Pro Arg Asp Leu Val Lys Pro Met Ala
                165                 170                 175 cat gag aag gga aaa cat ccg gat gaa gga atc acg tgg ttt cag acg      576
His Glu Lys Gly Lys His Pro Asp Glu Gly Ile Thr Trp Phe Gln Thr
            180                 185                 190 gtc tat aaa cga gtt cga agt ccc agt tgg ccg aag gaa tac gca ccg      624
Val Tyr Lys Arg Val Arg Ser Pro Ser Trp Pro Lys Glu Tyr Ala Pro
        195                 200                 205 att gaa tgt cgt caa gga ccg gga gag act atg ttt gta ccg tct gga      672
Ile Glu Cys Arg Gln Gly Pro Gly Glu Thr Met Phe Val Pro Ser Gly
    210                 215                 220 tgg tgg cat gtt gtt atc aat gag gaa tac aca att gca gtg act cac      720
Trp Trp His Val Val Ile Asn Glu Glu Tyr Thr Ile Ala Val Thr His
225                 230                 235                 240 aac tat tgc tct gtc gag aat ttg cat ctt gta tgg ccg aaa act gtg      768
Asn Tyr Cys Ser Val Glu Asn Leu His Leu Val Trp Pro Lys Thr Val
                245                 250                 255 aag gga agg ccc aag ttg agc aag cat tgg gtc aaa agg ctc aca gag      816
Lys Gly Arg Pro Lys Leu Ser Lys His Trp Val Lys Arg Leu Thr Glu
            260                 265                 270 caa cgt ccc gag ctt ctc gaa att atc aaa tcg gct tct gaa atc ccg      864
Gln Arg Pro Glu Leu Leu Glu Ile Ile Lys Ser Ala Ser Glu Ile Pro
        275                 280                 285 ctc tat gat atg aac gag tct tca agt gat tct tca agc tct tcc tca      912
Leu Tyr Asp Met Asn Glu Ser Ser Ser Asp Ser Ser Ser Ser Ser Ser
    290                 295                 300 tca tct gac gat tct tct gat gaa tct gat tgt gat gat agt ggg cga      960
Ser Ser Asp Asp Ser Ser Asp Glu Ser Asp Cys Asp Asp Ser Gly Arg
305                 310                 315                 320 tgt ggt gga cga aaa cgg aag aac gac gat cga tcg aat gag tgt ccg     1008
Cys Gly Gly Arg Lys Arg Lys Asn Asp Asp Arg Ser Asn Glu Cys Pro
                325                 330                 335 gag aaa atg agc act act tat ttt cag aac tcg cta gtt taa             1050
Glu Lys Met Ser Thr Thr Tyr Phe Gln Asn Ser Leu Val
            340                 345
```

```
<210> SEQ ID NO 7
<211> LENGTH: 349
<212> TYPE: PRT
<213> ORGANISM: Caenorhabditis elegans

<400> SEQUENCE: 7

Met Ser Leu Gly Arg Asp Arg Tyr Ser Leu Pro Arg Thr Tyr Lys Arg
1               5                   10                  15

Val Ser His Ala Lys Asp Lys Ala Arg Pro Glu Leu Arg Lys Phe Gly
            20                  25                  30

Trp Glu Thr Leu Gly Tyr Ser Glu Ser Phe Asn Leu Pro Pro Phe Arg
        35                  40                  45

Asp Ser Ile Gln Arg Val Asp Gly Asn Asn Leu Thr Val Glu Glu Phe
    50                  55                  60

Arg Arg Asp Phe Glu Arg Pro Arg Ile Pro Val Ile Thr Gly Leu
65                  70                  75                  80

Thr Asp Asn Trp Ala Ala Lys Asp Lys Trp Thr Val Glu Arg Arg Lys
                85                  90                  95

Thr Lys Lys Leu Ser Glu Asp Tyr Ser Val Pro Lys Phe Phe Glu Asp
            100                 105                 110

Asp Leu Phe His Tyr Ala Asp Asp Lys Lys Arg Pro Pro His Arg Trp
        115                 120                 125

Phe Val Met Gly Pro Ala Arg Ser Gly Thr Ala Ile His Ile Asp Pro
    130                 135                 140

Leu Gly Thr Ser Ala Trp Asn Ser Leu Leu Gln Gly His Lys Arg Trp
145                 150                 155                 160

Val Leu Ile Pro Pro Ile Ala Pro Arg Asp Leu Val Lys Pro Met Ala
                165                 170                 175

His Glu Lys Gly Lys His Pro Asp Glu Gly Ile Thr Trp Phe Gln Thr
            180                 185                 190

Val Tyr Lys Arg Val Arg Ser Pro Ser Trp Pro Lys Glu Tyr Ala Pro
        195                 200                 205

Ile Glu Cys Arg Gln Gly Pro Gly Glu Thr Met Phe Val Pro Ser Gly
    210                 215                 220

Trp Trp His Val Val Ile Asn Glu Glu Tyr Thr Ile Ala Val Thr His
225                 230                 235                 240

Asn Tyr Cys Ser Val Glu Asn Leu His Leu Val Trp Pro Lys Thr Val
                245                 250                 255

Lys Gly Arg Pro Lys Leu Ser Lys His Trp Val Lys Arg Leu Thr Glu
            260                 265                 270

Gln Arg Pro Glu Leu Leu Glu Ile Ile Lys Ser Ala Ser Glu Ile Pro
        275                 280                 285

Leu Tyr Asp Met Asn Glu Ser Ser Asp Ser Ser Ser Ser Ser
    290                 295                 300

Ser Ser Asp Asp Ser Ser Asp Glu Ser Asp Cys Asp Asp Ser Gly Arg
305                 310                 315                 320

Cys Gly Gly Arg Lys Arg Lys Asn Asp Asp Arg Ser Asn Glu Cys Pro
                325                 330                 335

Glu Lys Met Ser Thr Thr Tyr Phe Gln Asn Ser Leu Val
            340                 345

<210> SEQ ID NO 8
<211> LENGTH: 1227
<212> TYPE: DNA
<213> ORGANISM: Drosophila melanogaster
```

<220> FEATURE:
<221> NAME/KEY: CDS
<222> LOCATION: (1)..(1227)

<400> SEQUENCE: 8

| | | | | | | | | | | | | | | | | |
|---|---|---|---|---|---|---|---|---|---|---|---|---|---|---|---|---|
| atg | agc | gag | gaa | ttc | aag | ctg | ccc | aag | cgt | tcc | cgc | aag | cgc | aca | cgt | 48 |
| Met | Ser | Glu | Glu | Phe | Lys | Leu | Pro | Lys | Arg | Ser | Arg | Lys | Arg | Thr | Arg | |
| 1 | | | | 5 | | | | | 10 | | | | | 15 | | |
| gag | gtg | aag | cgc | aag | gct | cgt | ccg | gag | ctg | gac | ggc | gag | aat | gcc | tgg | 96 |
| Glu | Val | Lys | Arg | Lys | Ala | Arg | Pro | Glu | Leu | Asp | Gly | Glu | Asn | Ala | Trp | |
| | | | 20 | | | | | 25 | | | | | 30 | | | |
| tcg | gcc | atg | cgg | tac | tgt | gag | aag | ttc | gag | cca | ttt | tgg | gat | ttc | acc | 144 |
| Ser | Ala | Met | Arg | Tyr | Cys | Glu | Lys | Phe | Glu | Pro | Phe | Trp | Asp | Phe | Thr | |
| | | 35 | | | | | 40 | | | | | 45 | | | | |
| gat | aac | ctg | gag | cgg | atc | gag | gag | tcg | cag | gtg | ccg | gag | tcg | gag | ttc | 192 |
| Asp | Asn | Leu | Glu | Arg | Ile | Glu | Glu | Ser | Gln | Val | Pro | Glu | Ser | Glu | Phe | |
| | 50 | | | | | 55 | | | | | 60 | | | | | |
| atc | gaa | cgc | ttc | gag | cga | ccc | tac | aag | ccg | gtg | gtc | att | cgc | ggc | tgc | 240 |
| Ile | Glu | Arg | Phe | Glu | Arg | Pro | Tyr | Lys | Pro | Val | Val | Ile | Arg | Gly | Cys | |
| 65 | | | | | 70 | | | | | 75 | | | | | 80 | |
| acc | gat | ggc | tgg | ttg | gcg | ctg | gaa | aag | tgg | aca | cta | gcc | cgc | ctg | gcc | 288 |
| Thr | Asp | Gly | Trp | Leu | Ala | Leu | Glu | Lys | Trp | Thr | Leu | Ala | Arg | Leu | Ala | |
| | | | | 85 | | | | | 90 | | | | | 95 | | |
| aag | aag | tat | cgc | aac | cag | aag | ttc | aag | tgc | ggc | gag | gac | aac | gag | ggc | 336 |
| Lys | Lys | Tyr | Arg | Asn | Gln | Lys | Phe | Lys | Cys | Gly | Glu | Asp | Asn | Glu | Gly | |
| | | | 100 | | | | | 105 | | | | | 110 | | | |
| tat | agc | gtc | aag | atg | aag | atg | aag | tac | tac | gtg | gag | tac | atg | cag | agc | 384 |
| Tyr | Ser | Val | Lys | Met | Lys | Met | Lys | Tyr | Tyr | Val | Glu | Tyr | Met | Gln | Ser | |
| | | 115 | | | | | 120 | | | | | 125 | | | | |
| acg | cgc | gat | gac | agc | ccg | ctg | tac | atc | ttc | gac | agc | agc | ttc | ggc | gaa | 432 |
| Thr | Arg | Asp | Asp | Ser | Pro | Leu | Tyr | Ile | Phe | Asp | Ser | Ser | Phe | Gly | Glu | |
| | 130 | | | | | 135 | | | | | 140 | | | | | |
| cac | cat | cgt | cgg | cgc | aac | gtc | ctg | gat | gac | tat | gtg | gtg | ccc | aag | tat | 480 |
| His | His | Arg | Arg | Arg | Asn | Val | Leu | Asp | Asp | Tyr | Val | Val | Pro | Lys | Tyr | |
| 145 | | | | | 150 | | | | | 155 | | | | | 160 | |
| ttt | cgc | gac | gac | ctc | ttc | cag | tac | tgc | ggc | gag | aat | cgt | cgt | ccg | cct | 528 |
| Phe | Arg | Asp | Asp | Leu | Phe | Gln | Tyr | Cys | Gly | Glu | Asn | Arg | Arg | Pro | Pro | |
| | | | | 165 | | | | | 170 | | | | | 175 | | |
| tac | cgc | tgg | ttt | gtc | atg | gga | ccg | gct | cgc | tcc | ggc | acc | ggc | atc | cac | 576 |
| Tyr | Arg | Trp | Phe | Val | Met | Gly | Pro | Ala | Arg | Ser | Gly | Thr | Gly | Ile | His | |
| | | | 180 | | | | | 185 | | | | | 190 | | | |
| att | gat | cca | ctg | ggc | act | agt | gct | cgg | aac | acg | ctg | atc | cgc | ggc | cac | 624 |
| Ile | Asp | Pro | Leu | Gly | Thr | Ser | Ala | Arg | Asn | Thr | Leu | Ile | Arg | Gly | His | |
| | | 195 | | | | | 200 | | | | | 205 | | | | |
| aag | cgc | tgg | tgc | ctg | ttc | ccc | acc | caa | acg | ccc | aag | gag | ctg | ctc | aag | 672 |
| Lys | Arg | Trp | Cys | Leu | Phe | Pro | Thr | Gln | Thr | Pro | Lys | Glu | Leu | Leu | Lys | |
| | 210 | | | | | 215 | | | | | 220 | | | | | |
| gtc | acc | agt | gcc | atg | ggt | ggc | aag | cag | cga | gac | gag | gcc | atc | acc | tgg | 720 |
| Val | Thr | Ser | Ala | Met | Gly | Gly | Lys | Gln | Arg | Asp | Glu | Ala | Ile | Thr | Trp | |
| 225 | | | | | 230 | | | | | 235 | | | | | 240 | |
| ttc | agc | acc | ata | tat | ccg | cgc | acc | cag | ctg | cct | agt | tgg | ccg | gag | caa | 768 |
| Phe | Ser | Thr | Ile | Tyr | Pro | Arg | Thr | Gln | Leu | Pro | Ser | Trp | Pro | Glu | Gln | |
| | | | | 245 | | | | | 250 | | | | | 255 | | |
| tac | cgc | ccc | atc | gaa | gtg | ctg | cag | gga | gca | ggc | gag | act | gta | ttc | gtg | 816 |
| Tyr | Arg | Pro | Ile | Glu | Val | Leu | Gln | Gly | Ala | Gly | Glu | Thr | Val | Phe | Val | |
| | | | 260 | | | | | 265 | | | | | 270 | | | |
| ccc | ggc | ggc | tgg | tgg | cac | gtg | gtg | ctc | aac | atg | gac | gac | acc | att | gcc | 864 |
| Pro | Gly | Gly | Trp | Trp | His | Val | Val | Leu | Asn | Met | Asp | Asp | Thr | Ile | Ala | |
| | | 275 | | | | | 280 | | | | | 285 | | | | |
| atc | acc | cag | aac | ttc | agt | tca | cag | acg | aac | aac | ccc | tgc | gtc | tgg | cag | 912 |

```
Ile Thr Gln Asn Phe Ser Ser Gln Thr Asn Asn Pro Cys Val Trp Gln
        290                 295                 300 aag act gtt cgc ggc cgg cca aag ttg tca cgc aag tgg ctg cgc gtg         960
Lys Thr Val Arg Gly Arg Pro Lys Leu Ser Arg Lys Trp Leu Arg Val
305                 310                 315                 320 ctg cga gac cag cga ccg gag ctg gcc cag atc gcc gat agt att aac        1008
Leu Arg Asp Gln Arg Pro Glu Leu Ala Gln Ile Ala Asp Ser Ile Asn
                325                 330                 335 ctg aac gag agc acc ggc ttc gca tcg gac agc tcc agc aat tca agc        1056
Leu Asn Glu Ser Thr Gly Phe Ala Ser Asp Ser Ser Ser Asn Ser Ser
            340                 345                 350 tcc tcc tcg tcg agc agc tcc tcg tct tcg gag gag gag gag agc gac        1104
Ser Ser Ser Ser Ser Ser Ser Ser Ser Glu Glu Glu Glu Ser Asp
        355                 360                 365 gat ggc ggc gat tcc aac acg gac agc ggc cag gag agt ctg acg gcc        1152
Asp Gly Gly Asp Ser Asn Thr Asp Ser Gly Gln Glu Ser Leu Thr Ala
370                 375                 380 aag aag aaa aag aag cgg cgc atg gct ggc ggc ggc tcc ggg tcc ggc        1200
Lys Lys Lys Lys Lys Arg Arg Met Ala Gly Gly Gly Ser Gly Ser Gly
385                 390                 395                 400 tcc atg ggc gga tca tcg cgt tcc tga                                    1227
Ser Met Gly Gly Ser Ser Arg Ser
                405

<210> SEQ ID NO 9
<211> LENGTH: 408
<212> TYPE: PRT
<213> ORGANISM: Drosophila melanogaster

<400> SEQUENCE: 9

Met Ser Glu Glu Phe Lys Leu Pro Lys Arg Ser Lys Arg Thr Arg
1               5                   10                  15

Glu Val Lys Arg Lys Ala Arg Pro Glu Leu Asp Gly Glu Asn Ala Trp
            20                  25                  30

Ser Ala Met Arg Tyr Cys Glu Lys Phe Glu Pro Phe Trp Asp Phe Thr
        35                  40                  45

Asp Asn Leu Glu Arg Ile Glu Glu Ser Gln Val Pro Glu Ser Glu Phe
    50                  55                  60

Ile Glu Arg Phe Glu Arg Pro Tyr Lys Pro Val Ile Arg Gly Cys
65                  70                  75                  80

Thr Asp Gly Trp Leu Ala Leu Glu Lys Trp Thr Leu Ala Arg Leu Ala
                85                  90                  95

Lys Lys Tyr Arg Asn Gln Lys Phe Lys Cys Gly Glu Asp Asn Glu Gly
            100                 105                 110

Tyr Ser Val Lys Met Lys Met Lys Tyr Tyr Val Glu Tyr Met Gln Ser
        115                 120                 125

Thr Arg Asp Asp Ser Pro Leu Tyr Ile Phe Asp Ser Ser Phe Gly Glu
    130                 135                 140

His His Arg Arg Arg Asn Val Leu Asp Asp Tyr Val Val Pro Lys Tyr
145                 150                 155                 160

Phe Arg Asp Asp Leu Phe Gln Tyr Cys Gly Glu Asn Arg Arg Pro Pro
                165                 170                 175

Tyr Arg Trp Phe Val Met Gly Pro Ala Arg Ser Gly Thr Gly Ile His
            180                 185                 190

Ile Asp Pro Leu Gly Thr Ser Ala Arg Asn Thr Leu Ile Arg Gly His
        195                 200                 205

Lys Arg Trp Cys Leu Phe Pro Thr Gln Thr Pro Lys Glu Leu Leu Lys
```

-continued

```
                    210                 215                 220
Val Thr Ser Ala Met Gly Gly Lys Gln Arg Asp Glu Ala Ile Thr Trp
225                 230                 235                 240

Phe Ser Thr Ile Tyr Pro Arg Thr Gln Leu Pro Ser Trp Pro Glu Gln
                245                 250                 255

Tyr Arg Pro Ile Glu Val Leu Gln Gly Ala Gly Glu Thr Val Phe Val
                260                 265                 270

Pro Gly Gly Trp Trp His Val Val Leu Asn Met Asp Asp Thr Ile Ala
            275                 280                 285

Ile Thr Gln Asn Phe Ser Ser Gln Thr Asn Asn Pro Cys Val Trp Gln
        290                 295                 300

Lys Thr Val Arg Gly Arg Pro Lys Leu Ser Arg Lys Trp Leu Arg Val
305                 310                 315                 320

Leu Arg Asp Gln Arg Pro Glu Leu Ala Gln Ile Ala Asp Ser Ile Asn
                325                 330                 335

Leu Asn Glu Ser Thr Gly Phe Ala Ser Asp Ser Ser Ser Asn Ser Ser
                340                 345                 350

Ser Ser Ser Ser Ser Ser Ser Ser Glu Glu Glu Ser Asp
        355                 360                 365

Asp Gly Gly Asp Ser Asn Thr Asp Ser Gly Gln Glu Ser Leu Thr Ala
        370                 375                 380

Lys Lys Lys Lys Lys Arg Arg Met Ala Gly Gly Ser Gly Ser Gly
385                 390                 395                 400

Ser Met Gly Gly Ser Ser Arg Ser
                405

<210> SEQ ID NO 10
<211> LENGTH: 414
<212> TYPE: PRT
<213> ORGANISM: Artificial
<220> FEATURE:
<223> OTHER INFORMATION: NEED THIS INFO
<221> NAME/KEY: UNSURE
<222> LOCATION: (1)..(414)
<223> OTHER INFORMATION: X = any amino acid

<400> SEQUENCE: 10

Xaa Xaa Xaa Xaa Ser Xaa Lys Arg Xaa Arg Glu Ala Lys Arg Xaa Ala
1               5                   10                  15

Arg Pro Glu Leu Xaa Xaa Xaa Xaa Trp Xaa Xaa Xaa Xaa Tyr Xaa
                20                  25                  30

Glu Ser Phe Xaa Leu Xaa Xaa Xaa Xaa Xaa Asp Asn Xaa Xaa Arg
            35                  40                  45

Xaa Asp Xaa Xaa Xaa Leu Xaa Val Xaa Glu Phe Xaa Glu Arg Xaa Glu
    50                  55                  60

Arg Pro Tyr Lys Pro Val Val Xaa Xaa Xaa Xaa Xaa Xaa Trp Xaa
65                  70                  75                  80

Ala Xaa Glu Lys Trp Thr Leu Glu Arg Leu Lys Xaa Lys Tyr Arg Asn
        85                  90                  95

Gln Lys Phe Lys Cys Gly Glu Asp Asn Xaa Gly Tyr Ser Val Lys Met
            100                 105                 110

Lys Met Lys Tyr Tyr Xaa Glu Tyr Met Xaa Ser Thr Arg Asp Asp Ser
        115                 120                 125

Pro Leu Tyr Ile Phe Asp Ser Ser Xaa Gly Glu His Xaa Xaa Arg Arg
    130                 135                 140

Lys Leu Leu Glu Asp Tyr Xaa Val Pro Lys Phe Phe Xaa Asp Asp Leu
```

```
                145                 150                 155                 160

Phe Gln Tyr Ala Gly Glu Lys Arg Arg Pro Pro Tyr Arg Trp Phe Val
                        165                 170                 175

Met Gly Pro Xaa Arg Ser Gly Thr Gly Ile His Ile Asp Pro Leu Gly
                        180                 185                 190

Thr Ser Ala Trp Asn Xaa Leu Xaa Gln Gly His Lys Arg Trp Cys Leu
                        195                 200                 205

Phe Pro Thr Xaa Thr Pro Arg Glu Leu Xaa Lys Val Thr Xaa Xaa Glu
                        210                 215                 220

Gly Gly Xaa Gln Xaa Asp Glu Ala Ile Thr Trp Phe Xaa Xaa Ile Tyr
        225                 230                 235                 240

Pro Arg Thr Gln Leu Pro Xaa Trp Pro Xaa Glu Xaa Xaa Pro Xaa Glu
                        245                 250                 255

Xaa Leu Gln Xaa Pro Gly Glu Thr Val Phe Val Pro Gly Gly Trp Trp
                        260                 265                 270

His Val Val Leu Asn Xaa Asp Xaa Thr Ile Ala Ile Thr Gln Asn Phe
                        275                 280                 285

Xaa Ser Xaa Thr Asn Phe Pro Xaa Val Trp His Lys Thr Val Arg Gly
                        290                 295                 300

Arg Pro Lys Leu Ser Arg Lys Trp Xaa Arg Xaa Leu Xaa Xaa Xaa Xaa
        305                 310                 315                 320

Pro Glu Leu Ala Xaa Xaa Ala Asp Ser Xaa Xaa Leu Xaa Glu Ser Thr
                        325                 330                 335

Gly Xaa Ala Ser Asp Ser Ser Xaa Ser Ser Ser Ser Ser Ser
                        340                 345                 350

Ser Ser Ser Xaa Ser Asp Xaa Ser Glu Cys Xaa Xaa Gly Xaa Xaa Gly
                        355                 360                 365

Xaa Gly Xaa Xaa Xaa Xaa Xaa Xaa Xaa Xaa Lys Lys Arg Xaa Xaa
                370                 375                 380

Xaa Xaa Met Xaa Gly Xaa Gly Xaa Xaa Xaa Xaa Xaa Xaa Xaa Xaa Xaa
        385                 390                 395                 400

Xaa Ser Xaa Xaa Xaa Xaa Xaa Xaa Xaa Xaa Xaa Xaa
                        405                 410

<210> SEQ ID NO 11
<211> LENGTH: 12
<212> TYPE: PRT
<213> ORGANISM: Artificial
<220> FEATURE:
<223> OTHER INFORMATION: phosphatidylserine binding site
<221> NAME/KEY: unsure
<222> LOCATION: (1)..(12)
<223> OTHER INFORMATION: X = any amino acid

<400> SEQUENCE: 11

Phe Xaa Phe Xaa Leu Lys Xaa Xaa Xaa Lys Xaa Arg
1               5                   10
```

PHOSPHATIDYL SERINE RECEPTORS AND USES THEREOF

CROSS-REFERENCE TO RELATED APPLICATIONS

This application claims the benefit of priority under 35 U.S.C. §119(c) to U.S. Provisional Application Ser. No. 60/188,930, filed Mar. 8, 2000, and entitled "Product and Method for Regulation of Inflammation." The entire disclosure of U.S. Provisional Application Ser. No. 60/188,930 is incorporated herein by reference.

GOVERNMENT RIGHTS

This invention was made in part using government support under NIH Grant GM 60449 and NIH Grant GM 48211, all awarded by the National Institutes of Health. The government has certain rights to this invention.

FIELD OF THE INVENTION

The present invention generally relates to a novel phosphatidylserine (PS) receptor, to homologues thereof, to nucleic acids encoding such a receptor and homologues thereof, to agonist and antagonist compounds that specifically associate with and affect the activation state of such a receptor, including antibodies, antibody fragments and binding partners that selectively bind to such a receptor, and to methods of making and using such a receptor, homologues thereof, and agonist and antagonist compounds of such a receptor.

BACKGROUND OF THE INVENTION

The culmination of apoptosis in vivo is phagocytosis of cellular corpses. Of the numerous cells reported to recognize and remove apoptotic bodies, the macrophage is the most prominent. Apoptotic cells express cell surface changes which allow recognition and removal by macrophages. Removal occurs before lysis, which prevents the release of potentially toxic and immunogenic intracellular contents from the apoptotic cells into the surrounding tissue. Thus, in tissues such as the thymus in which apoptosis is ongoing, normal structure and function are maintained and inflammation is avoided. The removal of apoptotic cells also appears to be critical in the resolution of inflammation. Phagocytosis of apoptotic cells in inflammatory sites has been documented in vivo in experimental as well as clinical disease states, and disorders of apoptosis have been suggested to contribute to the persistence of chronic inflammatory conditions in the lung, kidney and other organs (Grigg et al., *Lancet.* 338:720–722, 1991; Cox et al., *Am. J. Respir. Cell. Mol. Biol.* 12:232–237, 1995; Haslett et al., *Phil. Trans. R. Soc. Lond. B.* 345:327–333, 1994).

During apoptosis, plasma membrane phospholipid asymmetry is lost, exposing phosphatidylserine (PS) externally (Fadok et al., *J Immunol* 148:2207–2216 (1992); Martin et al., *J Exp Med* 182:1545–1556 (1995); Verhoven et al., *J Exp Med* 182:1597–1601 (1995); van den Eijnde et al., *Apoptosis* 3:9–16 (1998)). Phagocytosis of apoptotic cells can be inhibited stereospecifically by PS and its structural analogues, but not by other anionic phospholipids, suggesting that PS is specifically recognized (Fadok et al., ibid.; Fadok et al., *J Immunol* 149:4029–4035 (1992); Fadok et al., *J Immunol* 151:4274–4285 (1993); Fadok et al., *J Immunol* 161:6250–6257 (1998); Pradhan et al., *Mol Biol Cell* 8:767–778 (1997); Bennett et al., *Circ Res* 77:1136–1142 (1995); Shiratsuchi et al., *J Biol Chem* 272:2354–2358 (1997)). However, prior to the present invention, the molecule responsible for PS recognition had not been positively identified.

Several potential candidates for PS recognition on apoptotic cells have been put forth, including CD36, CD68, CD14, and LOX-1 (Savill et al., *J Clin Invest* 90:1513–1522 (1992); Sambrano et al., *Proc Natl Acad Sci U S A* 92:1396–1400 (1995); Devitt et al., *Nature* 392:505–509 (1998); Oka et al., *Proc Natl Acad Sci U S A* 95:9535–9540 (1998)). In addition, β2GP1 may enhance uptake by bridging PS on the apoptotic cell to receptors on macrophages (Balasubramanian et al., *J Biol Chem* 272:31113–31117 (1997)). However, several observations suggest that receptors other than these scavenger/pattern recognition molecules must exist. These molecules do not appear to discriminate between PS and other anionic phospholipids including phosphatidylinositol (PI) (Oka et al., *Proc Natl Acad Sci U S A* 95:9535–9540 (1998); Rigotti et al., *J Biol Chem* 270:16221–16224 (1995); Wang et al., *J Biol Chem* 273:24309–24313 (1998); Ryeom et al., *J Cell Sci* 109:387–395 (1996); Shiratsuchi et al., *J Biol Chem* 274:5901–5908 (1999)), whereas uptake of apoptotic cells by PS-recognizing macrophages was not blocked by phosphatidylinositol (PI) or other anionic phospholipids (Fadok et al., *J Immunol* 148:2207–2216 (1992); Fadok et al., *J Immunol* 161:6250–6257 (1998)).

The removal of apoptotic cells is critical to normal tissue structure and function. In addition, one of the critical functions of the apoptotic cell when phagocytosed is to actively suppress macrophage proinflammatory functions. The nature and duration of the inflammatory response is determined to a large extent by competition between proinflammatory and anti-inflammatory uptake mechanisms. Disorders in either uptake or response to apoptotic cells by macrophages could contribute to chronic inflammation. Moreover, without being bound by theory, the present inventors believe that some pathogenic microorganisms and viruses may use the phosphatidylserine recognition pathway to gain entrance to a host cell. Also without being bound by theory, phosphatidylserine recognition may play a role in the ability of a tumor cell to avoid an immune response. Therefore, the ability to control cellular interactions which are mediated by phosphatidylserine recognition has multiple therapeutic benefits. Thus, there is a need in the art to identify and characterize the phosphatidylserine receptor.

SUMMARY OF THE INVENTION

The present invention generally relates to isolated phosphatidylserine receptor proteins, nucleic acid molecules, homologues thereof, agonist and antagonist compounds that specifically associate with and affect the activation state of such a receptor, and methods of making and using such a receptor, homologues thereof, and agonist and antagonist compounds of such a receptor.

One embodiment of the present invention relates to an isolated phosphatidylserine receptor protein selected from the group of: (a) a protein consisting essentially an amino acid sequence selected from the group consisting of: (i) an amino acid sequence spanning from between about positions 252 and 289 of SEQ ID NO:3 to about position 414 of SEQ ID NO:3; (ii) an amino acid sequence spanning from between about positions 252 and 289 of SEQ ID NO:5 to about position 403 of SEQ ID NO:5; (iii) an amino acid sequence spanning from between about positions 206 and 243 of SEQ ID NO:7 to about position 349 of SEQ ID NO:7; (iv) an amino acid sequence spanning from between about positions 257 and 294 of SEQ ID NO:9 to about position 408 of SEQ ID NO:9; and, (b) a homologue of the protein of (a), wherein the homologue consists essentially of an amino acid sequence that is at least about 70% identical, and more preferably at least about 80% identical, and more preferably at least about 90% identical, to the amino acid sequence of (a). The isolated phosphatidylserine receptor protein has a phosphatidylserine receptor biological activity. Preferably, such a protein consists essentially of an amino acid sequence selected from the group consisting of: (a) an amino acid sequence spanning from between about positions 289 of SEQ ID NO:3 to position 414 of SEQ ID NO:3; (b) an amino acid sequence spanning from between about positions 289 of SEQ ID NO:5 to position 403 of SEQ ID NO:5; (c) an amino acid sequence spanning from between about positions 243 of SEQ ID NO:7 to position 349 of SEQ ID NO:7; and (d) an amino acid sequence spanning from between about positions 294 of SEQ ID NO:9 to position 408 of SEQ ID NO:9. Particularly preferred phosphatidylserine receptor proteins in this embodiment include a protein that consists essentially of an amino acid sequence spanning from between about positions 252 and 289 of SEQ ID NO:3 to about position 414 of SEQ ID NO:3; and a protein that consists essentially of an amino acid sequence spanning from between about positions 252 and 289 of SEQ ID NO:5 to about position 403 of SEQ ID NO:3.

Another embodiment of the present invention relates to an isolated phosphatidylserine receptor protein selected from the group consisting of: (a) a protein comprising an amino acid sequence selected from the group consisting of SEQ ID NO:5, SEQ ID NO:7, and SEQ ID NO:9; and (b) a homologue of the protein of (a), wherein the homologue comprises an amino acid sequence that is at least 316 amino acid residues in length and that is at least about 70% identical, and more preferably at least about 80% identical, and more preferably at least about 90% identical, to the amino acid sequence of (a), wherein the homologue is not SEQ ID NO:3. The isolated phosphatidylserine receptor protein has a phosphatidylserine receptor biological activity. In a preferred embodiment, the protein is selected from the group consisting of: SEQ ID NO:5 and a homologue of SEQ ID NO:5, wherein the homologue comprises an amino acid sequence that is at least 316 amino acid residues in length and that is at least about 70% identical to SEQ ID NO:5. In a particularly preferred embodiment, the protein comprises an amino acid sequence selected from the group consisting of SEQ ID NO:5 and a fragment of at least about 316 amino acids of SEQ ID NO:5. In one aspect, the protein comprises an amino acid sequence selected from the group consisting of SEQ ID NO:5, SEQ ID NO:7, or SEQ ID NO:9. In one embodiment, the homologue comprises at least about 25 contiguous amino acid residues, and more preferably at least about 100 contiguous amino acid residues, of the amino acid sequence of (a). In a particularly preferred embodiment, the receptor protein is a soluble phosphatidylserine receptor.

Another embodiment of the present invention relates to an isolated phosphatidylserine receptor homologue, wherein the homologue comprises an amino acid sequence that is: (a) at least 316 amino acids in length; (b) at least about 70% identical to an amino acid sequence selected from the group consisting of SEQ ID NO:3, SEQ ID NO:5, SEQ ID NO:7, and SEQ ID NO:9; and, (c) less than 100% identical to the amino acid sequence of (a). In this embodiment, the homologue is not SEQ ID NO:3, and the homologue has a phosphatidylserine receptor biological activity. Preferably, the amino acid sequence of the homologue differs from the amino acid sequence of (a) by at least one modification selected from the group consisting of an amino acid deletion, an amino acid insertion, and an amino acid substitution. In another aspect of this embodiment, the homologue is less than about 95% identical to the amino acid sequence of (a). In another aspect of this embodiment, the homologue is at least about 80% identical, and more preferably at least about 90% identical, to an amino acid sequence selected from the group consisting of SEQ ID NO:3, SEQ ID NO:5, SEQ ID NO:7, and SEQ ID NO:9.

Yet another embodiment of the present invention relates to an isolated phosphatidylserine receptor protein comprising an amino acid sequence that aligns with 100% identity at least 50% of the non-Xaa residues of SEQ ID NO:10, wherein the protein is not SEQ ID NO:3, SEQ ID NO:5, SEQ ID NO:7, or SEQ ID NO:9.

Also included in the present invention are fusion proteins that include any of the above-described phosphatidylserine receptor proteins, including homologues thereof, that are operatively linked to a heterologous protein sequence.

Another embodiment of the present invention relates to an isolated antibody, antigen binding fragment of such an antibody, or a binding partner, that selectively binds to any of the above-described phosphatidylserine receptor proteins, including homologues thereof. In a preferred embodiment, the antibody, antigen binding fragment, or binding partner, selectively binds to a protein consisting essentially of a fragment of SEQ ID NO:3 spanning from between about positions 252 and 289 of SEQ ID NO:3 and about position 414 of SEQ ID NO:3. In another preferred embodiment, the antibody, antigen binding fragment, or binding partner, selectively binds to a protein consisting essentially of a fragment of SEQ ID NO:5 spanning from between about positions 252 and 289 of SEQ ID NO:5 and about position 403 of SEQ ID NO:5.

Yet another embodiment of the present invention relates to a composition comprising at least about 1 $\mu$g of an isolated phosphatidylserine receptor protein of the present invention. The protein is selected from the group consisting of: (a) a protein comprising an amino acid sequence selected from the group consisting of SEQ ID NO:3, SEQ ID NO:5, SEQ ID NO:7, and SEQ ID NO:9; (b) a homologue of the protein of (a), wherein the homologue comprises an amino acid sequence that is at least 316 amino acid residues in length and that is at least about 70% identical, and more preferably at least about 80% identical, and more preferably at least about 90% identical, to the amino acid sequence of (a); (c) a fragment of the protein of (a) consisting essentially an amino acid sequence selected from the group consisting of: (i) an amino acid sequence spanning from between about positions 252 and 289 of SEQ ID NO:3 to about position 414 of SEQ ID NO:3; (ii) an amino acid sequence spanning from between about positions 252 and 289 of SEQ ID NO:5 to about position 403 of SEQ ID NO:5; (iii) an amino acid sequence spanning from between about positions 206 and 243 of SEQ ID NO:7 to about position 349 of SEQ ID NO:7; (iv) an amino acid sequence spanning from between about positions 257 and 294 of SEQ ID NO:9 to about position 408 of SEQ ID NO:9 spanning from between about positions 252 and 289 of SEQ ID NO:3 and about position 414 of SEQ ID NO:3; and (d) a homologue of the protein of (c), wherein the wherein the homologue consists essentially of an amino acid sequence that is at least about 70% identical, and more preferably at least about 80% identical, and more preferably at least about 90% identical, to the amino acid sequence of (c). The isolated phosphatidylserine receptor protein has a phosphatidylserine receptor biological activity. In a preferred aspect of this embodiment, the protein consists essentially of an amino acid sequence selected from the group consisting of a fragment of at least about 316 amino acids of SEQ ID NO:3, and a fragment of SEQ ID NO:3 spanning from between positions 252 and 289 of SEQ ID NO:3 and position 414 of SEQ ID NO:3, wherein the protein has a phosphatidylserine biological activity. In one aspect, the homologue of (b) comprises at least about 25 contiguous amino acid residues of SEQ ID NO:3. In another aspect, the homologue of (b) comprises at least about 100 contiguous amino acid residues of SEQ ID NO:3. In a preferred embodiment, the protein comprises SEQ ID NO:3.

Yet another embodiment of the present invention relates to a composition comprising an isolated phosphatidylserine receptor protein selected from the group consisting of: (a) a protein comprising an amino acid sequence selected from the group consisting of SEQ ID NO:3, SEQ ID NO:5, SEQ ID NO:7, and SEQ ID NO:9; (b) a homologue of the protein of (a), wherein the homologue comprises an amino acid sequence that is at least 316 amino acid residues in length and that is at least about 70% identical to the amino acid sequence of (a); (c) a fragment of the protein of (a) consisting essentially an amino acid sequence selected from the group consisting of: (i) an amino acid sequence spanning from between about positions 252 and 289 of SEQ ID NO:3 to about position 414 of SEQ ID NO:3; (ii) an amino acid sequence spanning from between about positions 252 and 289 of SEQ ID NO:5 to about position 403 of SEQ ID NO:5; (iii) an amino acid sequence spanning from between about positions 206 and 243 of SEQ ID NO:7 to about position 349 of SEQ ID NO:7; (iv) an amino acid sequence spanning from between about positions 257 and 294 of SEQ ID NO:9 to about position 408 of SEQ ID NO:9 spanning from between about positions 252 and 289 of SEQ ID NO:3 and about position 414 of SEQ ID NO:3; and (d) a homologue of the protein of (c), wherein the wherein the homologue consists essentially of an amino acid sequence that is at least about 70% identical to the amino acid sequence of (c). The isolated, substantially purified phosphatidylserine receptor protein has a phosphatidylserine receptor biological activity. In this composition, at least about 80% weight/weight of total protein in the composition is the isolated phosphatidylserine receptor protein. Preferably, the phosphatidylserine receptor protein comprises an amino acid sequence selected from the group consisting of: SEQ ID NO:3, SEQ ID NO:5, SEQ ID NO:7, and SEQ ID NO:9.

Another embodiment of the present invention relates to an isolated cDNA or RNA molecule selected from the group consisting of: (a) a nucleic acid sequence consisting essentially of nucleotides encoding an amino acid sequence selected from the group consisting of SEQ ID NO:3, SEQ ID NO:5, SEQ ID NO:7, and SEQ ID NO:9; (b) a nucleic acid sequence encoding a homologue of the protein of (a), wherein the homologue comprises an amino acid sequence that is between 316 and 414 amino acid residues in length and that is at least about 70% identical to the amino acid sequence of (a); (c) a nucleic acid sequence encoding a protein consisting essentially of a fragment of the amino acid sequence of (a) selected from the group consisting of: (i) a fragment spanning from between about positions 252 and 289 of SEQ ID NO:3 to about position 414 of SEQ ID NO:3; (ii) a fragment spanning from between about positions 252 and 289 of SEQ ID NO:5 to about position 403 of SEQ ID NO:5; (iii) a fragment spanning from between about positions 206 and 243 of SEQ ID NO:7 to about position 349 of SEQ ID NO:7; and (iv) a fragment spanning from between about positions 257 and 294 of SEQ ID NO:9 to about position 408 of SEQ ID NO: 9; (d) a nucleic acid sequence encoding a homologue of the protein of (c), wherein the wherein the homologue consists essentially of an amino acid sequence that is at least about 70% identical to the amino acid sequence of (c); and (e) a nucleic acid sequence that is fully complementary to the nucleic acid sequence of (a), (b), (c) or (d). In this embodiment, the nucleic acid sequence is preferably selected from the group consisting of SEQ ID NO:2, SEQ ID NO:4, SEQ ID NO:6 and SEQ ID NO:8. In a particularly preferred embodiment, the nucleic acid sequence is SEQ ID NO:2. In another aspect, the nucleic acid sequence consists essentially of from between nucleotide 756 and nucleotide 867 of SEQ ID NO:2 to nucleotide 1242 of SEQ ID NO:2.

Yet another embodiment of the present invention relates to an isolated cDNA or RNA molecule selected from the group consisting of: (a) a nucleic acid sequence encoding a protein comprising an amino acid sequence selected from the group consisting of SEQ ID NO:5, SEQ ID NO:7, and SEQ ID NO:9; (b) a nucleic acid sequence encoding a homologue of the protein of (a), wherein the homologue comprises an amino acid sequence that is at least 316 amino acid residues in length and that is at least about 70% identical to the amino acid sequence of (a), wherein the homologue is not SEQ ID NO:3; (c) a nucleic acid sequence encoding a protein consisting essentially of a fragment of the amino acid sequence of (a) selected from the group consisting of: (i) a fragment spanning from between about positions 252 and 289 of SEQ ID NO:5 to position 403 of SEQ ID NO:5; (ii) a fragment spanning from between about positions 206 and 243 of SEQ ID NO:7 to position 349 of SEQ ID NO:7; and, (iii) a fragment spanning from between about positions 257 and 294 of SEQ ID NO:9 to position 408 of SEQ ID NO:9; (d) a nucleic acid sequence encoding a homologue of the protein of (c), wherein the wherein the homologue consists essentially of an amino acid sequence that is at least about 70% identical to the amino acid sequence of (c); and (e) a nucleic acid sequence that is fully complementary to the nucleic acid sequence of (a), (b), (c) or (d). In one aspect, the nucleic acid sequence is selected from the group consisting of SEQ ID NO:4, SEQ ID NO:6 and SEQ ID NO: 8. In a preferred embodiment, the nucleic acid sequence comprises SEQ ID NO:4. In another embodiment, the nucleic acid sequence consists essentially of from between nucleotide 756 and nucleotide 867 of SEQ ID NO:4 to nucleotide 1209 of SEQ ID NO:4.

Also included in the present invention are recombinant nucleic acid molecules consisting of any of the above-described isolated cDNA or RNA molecules and a nucleic acid sequence that is heterologous to the isolated cDNA or RNA molecule. In one aspect, the heterologous nucleic acid sequence is an expression vector. Another embodiment of the present invention relates to a recombinant cell that expresses any of the recombinant nucleic acid molecules described herein.

Yet another embodiment of the present invention relates to a method to identify a regulator of a phosphatidylserine receptor. Such a method includes a first step of: (a) contacting a phosphatidylserine receptor protein with a putative regulatory compound, wherein the phosphatidylserine receptor protein is selected from the group consisting of: (i) a protein comprising an amino acid sequence selected from the group consisting of SEQ ID NO:3, SEQ ID NO:5, SEQ ID NO:7, and SEQ ID NO:9; (ii) a homologue of the protein of (a), wherein the homologue comprises an amino acid sequence that is at least 316 amino acid residues in length and that is at least about 70% identical to the amino acid sequence of (a); (iii) a protein consisting essentially of a fragment of the amino acid sequence of (a) selected from the group consisting of: (1) a fragment spanning from between about positions 252 and 289 of SEQ ID NO:3 to position 414 of SEQ ID NO:3; (2) a fragment spanning from between about positions 252 and 289 of SEQ ID NO:5 to position 403 of SEQ ID NO:5; (3) a fragment spanning from between about positions 206 and 243 of SEQ ID NO:7 to position 349 of SEQ ID NO:7; and, (4) a fragment spanning from between about positions 257 and 294 of SEQ ID NO:9 to position 408 of SEQ ID NO:9; and, (iv) a homologue of the protein of (iii), wherein the homologue comprises an amino acid sequence that is at least about 70% identical to the amino acid sequence of (iii). The phosphatidylserine receptor protein has a phosphatidylserine receptor biological activity. Such a method further includes the steps of: (b) detecting whether the putative regulatory compound binds to the receptor; and, (c) detecting whether the putative regulatory compound increases or decreases activity of the receptor as compared to prior to contact with the compound. Compounds that bind to the receptor and increase or decrease activity of the receptor, as compared to a receptor in the absence of the compound, indicates that the putative regulatory compound is a regulator of the phosphatidylserine receptor.

In this embodiment, the step of detecting whether the putative regulatory compound increases or decreases activation of the receptor can include, but is not limited to, the steps of contacting the receptor with a stimulator of the receptor and detecting whether activation of the receptor is increased or decreased in the presence of the putative regulatory compound as compared to in the absence of the putative regulatory compound. In one aspect, the method further comprises a step of detecting whether the putative regulatory compound regulates a biological activity of a cell that expresses the receptor, the biological activity being selected from the group consisting of transforming growth factor β (TGFβ) production, prostaglandin E2 (PGE2) production, tumor necrosis factor α (TNFα) production, chemokine production, granulocyte-macrophage colony stimulating factor (GM-CSF) production, interleukin-1 (IL-1) production, phosphorylation of the receptor, and phagocytosis of apoptotic cells.

Another embodiment of the present invention relates to a method to stimulate or increase the activity of a phosphatidylserine receptor. Such a method includes the step of contacting a phosphatidylserine receptor with an agonist of the phosphatidylserine receptor, wherein the agonist increases the activity of the phosphatidylserine receptor, and wherein the receptor comprises an amino acid sequence selected from the group consisting of: SEQ ID NO:3, SEQ ID NO:5, SEQ ID NO:7, and SEQ ID NO:9. Preferably, the agonist is selected from the group consisting of: an antibody that selectively binds to and activates the phosphatidylserine receptor, an antigen binding fragment that selectively binds to and activates the phosphatidylserine receptor, a binding partner that selectively binds to and activates the phosphatidylserine receptor, phosphatidylserine, and a product of drug design that increases the activity of the receptor as compared to in the absence of the product. In one aspect, the agonist is an antibody that selectively binds to and activates the receptor. In another aspect, the agonist increases production of a factor selected from the group consisting of transforming growth factor β (TGFβ) and prostaglandin E2 (PGE2) by cells in the subject. In another aspect, the agonist decreases production of a factor selected from the group consisting of tumor necrosis factor α (TNFα), a chemokine, granulocyte-macrophage colony stimulating factor (GM-CSF), and interleukin-1 (IL-1) by in the subject. Preferably, the phosphatidylserine receptor is expressed by a cell selected from the group consisting of a macrophage, a fibroblast, a dendritic cell, a tumor cell, an epithelial cell and an endothelial cell. In one aspect, the agonist reduces inflammation in a patient.

Another embodiment of the present invention relates to a method to reduce the production of inflammatory cytokines by cells in a subject. This method includes the step of contacting the cells that express a phosphatidylserine receptor with an agonist of a phosphatidylserine receptor, wherein the agonist increases the activity of a phosphatidylserine receptor, and wherein the receptor comprises an amino acid sequence selected from the group consisting of: SEQ ID NO:3, SEQ ID NO:5, SEQ ID NO:7, and SEQ ID NO:9.

Yet another embodiment of the present invention relates to a method to promote survival of a transplanted cell or graft, comprising administering to a transplant recipient an agonist of a phosphatidylserine receptor, wherein the agonist increases the activity of a phosphatidylserine receptor, and wherein the receptor comprises an amino acid sequence selected from the group consisting of SEQ ID NO:3, SEQ ID NO:5, SEQ ID NO:7, and SEQ ID NO:9.

Another embodiment of the present invention relates to a method to treat an autoimmune disease, comprising administering to a subject that has an autoimmune disease an agonist of a phosphatidylserine receptor, wherein the agonist increases the activity of a phosphatidylserine receptor, and wherein the receptor comprises an amino acid sequence selected from the group consisting of SEQ ID NO:3, SEQ ID NO:5, SEQ ID NO:7, and SEQ ID NO:9.

Yet another embodiment of the present invention relates to a method to reduce the activity of a phosphatidylserine receptor, comprising contacting a phosphatidylserine receptor with an antagonist of the phosphatidylserine receptor, wherein the antagonist decreases the activity of the phosphatidylserine receptor, and wherein the receptor comprises an amino acid sequence selected from the group consisting of: SEQ ID NO:3, SEQ ID NO:5, SEQ ID NO:7, and SEQ ID NO:9. Preferably, the antagonist is selected from the group consisting of an antibody that reduces the activity of the receptor, an antigen binding fragment that reduces the activity of the receptor, a binding partner that reduces the activity of the receptor, a product of drug design that reduces the biological activity of the receptor, an anti-sense nucleic acid molecule that binds to a nucleic acid molecule encoding the receptor, a ribozyme that is specific for PS receptor RNA, and a soluble phosphatidylserine receptor. In a preferred embodiment, the antagonist is an antibody that selectively binds to the receptor and reduces the activity of the receptor. In one embodiment, the antagonist is a soluble phosphatidylserine receptor comprising an amino acid sequence selected from the group consisting of: (a) an amino acid sequence spanning from between about positions 252 and 289 of SEQ ID NO:3 to position 414 of SEQ ID NO:3; (b) an amino acid sequence spanning from between about positions 252 and 289 of SEQ ID NO:5 to position 403 of SEQ ID NO:5; (c) an amino acid sequence spanning from between about positions 206 and 243 of SEQ ID NO:7 to position 349 of SEQ ID NO:7; (d) an amino acid sequence spanning from between about positions 257 and 294 of SEQ ID NO:9 to position 408 of SEQ ID NO:9; and, (e) an amino acid sequence that is a homologue of the amino acid sequence of (a), (b), (c), or (d), wherein the wherein the homologue amino acid sequence consists essentially of an amino acid sequence that is at least about 70% identical to the amino acid sequence of (a), (b), (c), or (d). The homologue has a phosphatidylserine receptor biological activity.

Another embodiment of the present invention is a method to reduce the association of an apoptotic tumor cell with a phosphatidylserine receptor expressed on the surface of bystander tumor cells, macrophages or dendritic cells, comprising contacting tumor cells of a patient with an antagonist of a phosphatidylserine receptor, wherein the antagonist decreases the activity of the phosphatidylserine receptor, and wherein the phosphatidylserine receptor comprises an amino acid sequence selected from the group consisting of: SEQ ID NO:3, SEQ ID NO:5, SEQ ID NO:7, and SEQ ID NO:9.

Yet another embodiment of the present invention is a method to inhibit the infection of a host cell by a parasite, comprising contacting the host cell with an antagonist of a phosphatidylserine receptor, wherein the antagonist decreases the activity of the phosphatidylserine receptor, and wherein the phosphatidylserine receptor comprises an amino acid sequence selected from the group consisting of: SEQ ID NO:3, SEQ ID NO:5, SEQ ID NO:7, and SEQ ID NO:9. Preferably, the parasite is selected from the group consisting of Trypanosomes and Leishmania.

Another embodiment of the present invention relates to a method to inhibit viral infection of host cells, comprising contacting the host cell with an antagonist of a phosphatidylserine receptor, wherein the antagonist decreases the activity of the phosphatidylserine receptor, and wherein the phosphatidylserine receptor comprises an amino acid sequence selected from the group consisting of: SEQ ID NO:3, SEQ ID NO:5, SEQ ID NO:7, and SEQ ID NO:9. Preferably, the viral infection is by a Herpes virus, and even more preferably, by a cytomegalovirus.

BRIEF DESCRIPTION OF THE DRAWINGS OF THE INVENTION

FIGS. 2A–2E are bar graphs illustrating that mAb 217 inhibits the uptake of apoptotic Jurkat T cells by several phagocytes.

DETAILED DESCRIPTION OF THE INVENTION

Figure 1:
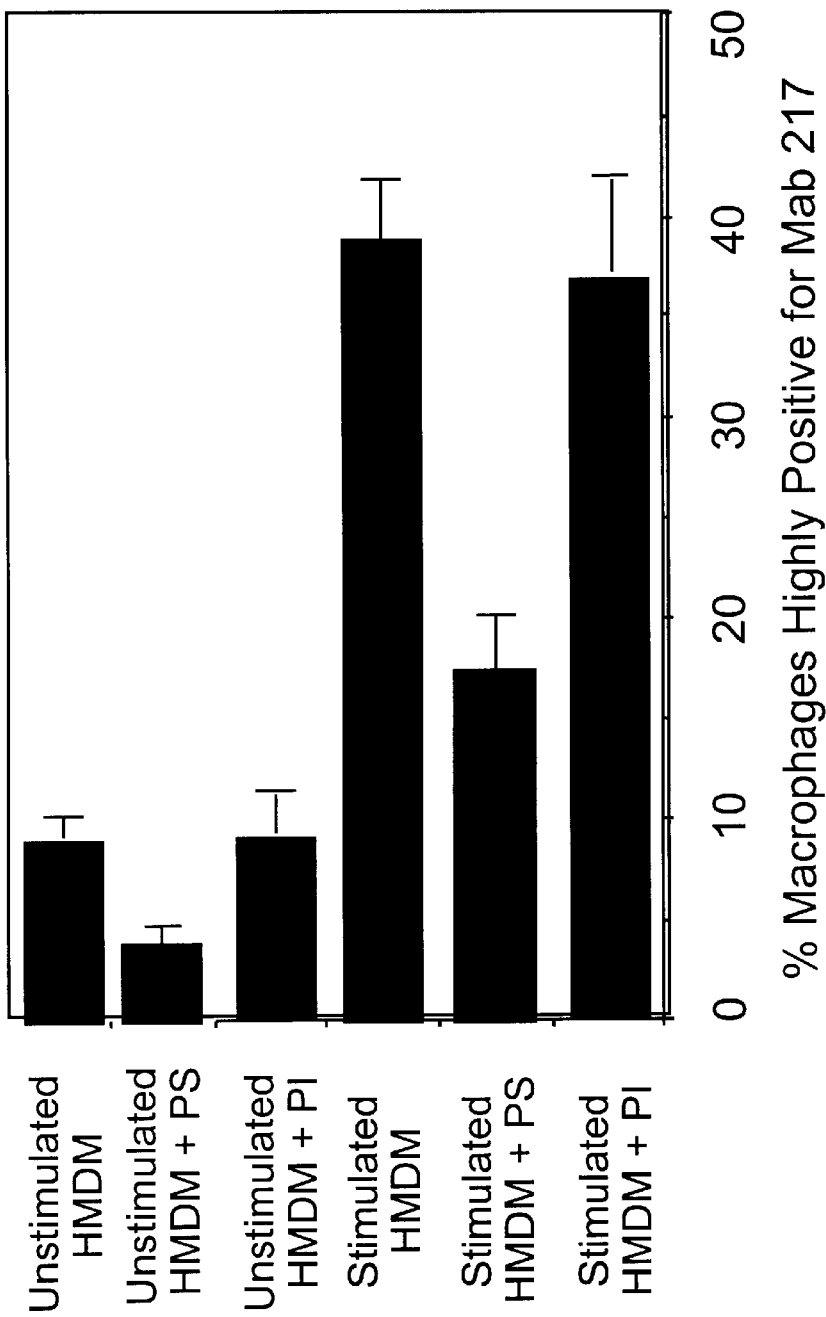
FIG. 1 is a bar graph illustrating that liposomes containing phosphatidylserine (PS) but not phosphatidylinositol (PI) inhibit the binding of mAb 217 to stimulated macrophages.

The present inventors have identified and cloned by phage display a gene encoding a novel protein which recognizes phosphatidylserine (PS) on apoptotic cells. It is demonstrated herein that this gene, when transfected into B and T lymphocytes, enables them to recognize and engulf apoptotic cells in a PS-specific manner. Flow cytometric analysis using a new monoclonal antibody indicated that the protein was expressed on the surface of macrophages, fibroblasts, epithelial cells, dendritic cells, endothelial cells, and melanoma cells. This antibody, like PS liposomes, inhibited the phagocytosis of apoptotic cells and, in macrophages, induced an anti-inflammatory state. The present inventors have also discovered that the PS receptor of the present invention is highly homologous to genes of unknown function in Caenorhabditis elegans and Drosophila melanogaster, indicating for the first time a function for the products of those genes, and importantly, that PS recognition on apoptotic cells during their removal by phagocytes is highly conserved throughout phylogeny. Taken together, the present inventors demonstrate herein that the PS receptor is present and active in vivo. When this receptor is stimulated, macrophages, fibroblasts, epithelial cells, dendritic cells, endothelial cells and melanoma cells, rapidly release TGFβ, among other factors, which results in down regulation of inflammatory cytokine production.

One embodiment of the present invention relates to an isolated phosphatidylserine receptor protein. Such a protein is characterized as having phosphatidylserine receptor biological activity (described below). According to the present invention, such a protein is selected from the group of:

(a) a protein comprising, consisting essentially of, or consisting of, an amino acid sequence selected from the group consisting of SEQ ID NO:3, SEQ ID NO:5, SEQ ID NO:7, SEQ ID NO:9 and SEQ ID NO:10;

(b) a homologue of the protein of (a), wherein the homologue comprises, consists essentially of, or consists of, an amino acid sequence that is at least about 316 amino acids in length, and preferably between 316 and 414 amino acid residues in length, and that is at least about 70% identical to the amino acid sequence of (a);

(c) a protein comprising, consisting essentially of, or consisting of, a fragment of the amino acid sequence of (a) selected from the group consisting of: (i) a fragment spanning from between about positions 252 and 289 of SEQ ID NO:3 to position 414 of SEQ ID NO:3; (ii) a fragment spanning from between about positions 252 and 289 of SEQ ID NO:5 to position 403 of SEQ ID NO:5; (iii) a fragment spanning from between about positions 206 and 243 of SEQ ID NO:7 to position 349 of SEQ ID NO:7; (iv) a fragment spanning from between about positions 257 and 294 of SEQ ID NO:9 to position 408 of SEQ ID NO:9; and (v) a fragment spanning from between about positions 252 and 289 of SEQ ID NO:10 to position 414 of SEQ ID NO:10; and, (d) a homologue of the protein of (c), wherein the wherein the homologue comprises, consists essentially of, or consists of, an amino acid sequence that is from about 106 to about 166 amino acids in length, and that is at least about 70% identical to the amino acid sequence of (c).

According to the present invention, a phosphatidylserine (PS) receptor, is a protein that has PS receptor biological activity, including full-length PS receptor proteins, soluble PS receptor proteins, other biologically active fragments of PS receptor proteins, fusion proteins, or any homologue of a naturally occurring PS receptor, as described in detail below. A homologue of an PS receptor includes proteins which differ from a naturally occurring PS receptor in that at least one or a few, but not limited to one or a few, amino acids have been deleted (e.g., a truncated version of the protein, such as a peptide or fragment), inserted, inverted, substituted and/or derivatized (e.g., by glycosylation, phosphorylation, acetylation, myristoylation, prenylation, palpitation, amidation and/or addition of glycosylphosphatidyl inositol). Preferred homologues of a naturally occurring PS receptor are described in detail below.

An isolated PS receptor protein, according to the present invention, is a protein that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated PS receptor protein of the present invention is produced recombinantly. Reference to a PS receptor from a specific organism, such as a "human PS receptor", by way of example, refers to a PS receptor (including a homologue of a naturally occurring PS receptor) from a human or a PS receptor that has been otherwise produced from the knowledge of the structure (e.g., sequence) of a naturally occurring PS receptor from a human. In other words, a human PS receptor includes any PS receptor that has the structure and function of a naturally occurring PS receptor from a human or that has a structure and function that is sufficiently similar to a human PS receptor such that the PS receptor is a biologically active (i.e., has biological activity) homologue of a naturally occurring PS receptor from a human. As such, a human PS receptor can include purified, partially purified, recombinant, mutated/modified and synthetic proteins.

In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). For example, a biological activity of a PS receptor includes PS receptor biological activity. Modifications of a protein, such as in a homologue or mimetic (discussed below), may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action of a protein. Similarly, modifications which result in an increase in protein expression or an increase in the activity of the protein, can be referred to as amplification, overproduction, activation, enhancement, up-regulation or increased action of a protein.

As used herein, a protein that has "PS receptor biological activity" or that is referred to as a "PS receptor" refers to a protein that has an activity that can include any one, and preferably more than one, of the following characteristics: (a) binds to phosphatidylserine; (b) responds to contact with phosphatidylserine and/or an agonist (i.e., stimulation) by inducing transforming growth factor β (TGFβ) production and/or prostaglandin E2 (PGE2) production by a cell expressing such a receptor; (c) enables a cell expressing such receptor to recognize apoptotic cells in a phosphatidylserine-specific manner; (d) enables a cell expressing such receptor to engulf apoptotic cells in a phosphatidylserine-specific manner; (e) responds to contact with phosphatidylserine and/or an agonist by down regulating production of inflammatory cytokines (e.g., tumor necrosis factor α (TNFα), chemokine production, granulocyte-macrophage colony stimulating factor (GM-CSF) production, interleukin-1 (IL-1)) by a cell expressing such a receptor; and, (f) binds to and/or enables engulfment of phosphatidylserine-expressing particles which include, but are not limited to, lipid-symmetric red blood cells, PS-containing liposomes, parasites, viruses and other microbes. In one embodiment, PS receptor activity can include inhibition of antigen presentation by a dendritic cell expressing the PS receptor, when the PS receptor is stimulated. PS receptor biological activity can be evaluated by one of skill in the art by any suitable in vitro or in vivo assay. Such assays are described for example, in the Examples section. For example, a human PS receptor of the present invention can be identified by its ability to be selectively bound by a PS receptor-specific antibody of the present invention, such as mAb 217 and nAb 284 described in Example 1. Alternatively, a PS receptor of the present invention can be identified by its ability to bind phosphatidylserine, such as in any standard binding assay. A PS receptor of the present invention can also be identified by its ability to bind and phagocytose apoptotic cells in a phosphatidylserine-specific manner. Such assays are described, for example, in Example 1 and in Fadok et al., *J Immunol* 148:2207–2216 (1992); Fadok et al., *J Immunol* 149:4029–4035 (1992); Fadok et al., *J Immunol* 151:4274–4285 (1993); Fadok et al., *J Immunol* 161:6250–6257 (1998). Each of these publications is incorporated herein in its entirety by reference. Additionally, now that the primary structure of two mammalian PS receptors and two homologues of mammalian PS receptors from invertebrate species have been identified by the present inventors, a PS receptor can be identified by its structural similarity to one of the PS receptors or homologues thereof described herein.

In one embodiment of the present invention, a PS receptor has an amino acid sequence that comprises, consists essentially of, or consists of one of the following amino acid sequences: SEQ ID NO:3, SEQ ID NO:5, SEQ ID NO:7, SEQ ID NO:9 and SEQ ID NO:10. SEQ ID NO:3 represents a human PS receptor of the present invention (encoded by nucleic acid sequence SEQ ID NO:2); SEQ ID NO:5 represents a mouse PS receptor of the present invention (encoded by nucleic acid sequence SEQ ID NO:4); SEQ ID NO:7 represents a PS receptor homologue from *C. elegans* (encoded by nucleic acid sequence SEQ ID NO:6); SEQ ID NO:9 represents a PS receptor homologue from *Drosophila* (encoded by nucleic acid sequence SEQ ID NO:8); and SEQ ID NO:10 represents a consensus sequence for a PS receptor that was determined by the present inventors by aligning and comparing the sequences, SEQ ID NO:3, SEQ ID NO:5, SEQ ID NO:7 and SEQ ID NO:9 (See FIG. 3).

A preferred embodiment of the present invention relates to a composition comprising at least about 500 ng, and preferably at least about 1 μg, and more preferably at least about 5 μg, and more preferably at least about 10 μg, and more preferably at least about 25 μg, and more preferably at least about 50 μg, and more preferably at least about 75 μg, and more preferably at least about 100 μg, and more preferably at least about 250 μg, and more preferably at least about 500 μg, and more preferably at least about 750 μg, and more preferably at least about 1 mg, and more preferably at least about 5 mg, of an isolated phosphatidylserine receptor protein comprising any of the PS receptor proteins or homologues thereof discussed herein. In a particularly preferred embodiment, such a composition comprises at least about 1 μg of a PS receptor protein comprising: (a) SEQ ID NO:3; (b) a homologue of SEQ ID NO:3, wherein the homologue comprises an amino acid sequence that is at least about 316 amino acid residues in length and that is at least about 70% identical to SEQ ID NO:3; (c) a fragment of SEQ ID NO:3 spanning from between positions 252 and 289 of SEQ ID NO:3 and position 414 of SEQ ID NO:3; and (d) a homologue of the protein of (c), wherein the wherein the homologue consists essentially of an amino acid sequence that is from about 106 to 166 amino acids in length and that is at least about 70% identical to the amino acid sequence of (c). Each of such proteins has phosphatidylserine receptor biological activity. A composition of the present invention can include any carrier with which the protein is associated by virtue of the protein preparation method, a protein purification method, or a preparation of the protein for use in an in vitro, ex vivo, or in vivo method according to the present invention. For example, such a carrier can include any suitable excipient, buffer and/or delivery vehicle, such as a pharmaceutically acceptable carrier (discussed below), which is suitable for combining with the PS receptor of the present invention so that the protein can be used in vitro, ex vivo or in vivo according to the present invention. For example, a PS receptor protein of the present invention (including homologues) can be used in methods that include, but are not limited to, in vitro assays described herein, including drug design methods, as well as in in vivo therapeutic methods and antibody production methods, all described elsewhere herein.

The present invention also includes homologues of any of SEQ ID NO:3, SEQ ID NO:5, SEQ ID NO:7, SEQ ID NO:9 and SEQ ID NO:10, wherein the homologue has phosphatidylserine receptor biological activity, as described previously herein. As discussed above, a homologue of a PS receptor can include proteins which differ from a naturally occurring PS receptor in that at least one or a few, but not limited to one or a few, amino acids have been deleted (e.g., a truncated version of the protein, such as a peptide or fragment), inserted, inverted, substituted and/or derivatized. In one aspect, a homologue of the PS receptor has an amino acid sequence that is at least about 316 amino acids in length, and preferably between 316 and 414 amino acids in length, and which is at least about 70% identical to any of SEQ ID NO:3, SEQ ID NO:5, SEQ ID NO:7, SEQ ID NO:9 or SEQ ID NO: 10, over a length of SEQ ID NO:3, SEQ ID NO:5, SEQ ID NO:7, SEQ ID NO:9 or SEQ ID NO:10 that is at least the same as the length of the homologue (i.e., over at least 316 amino acids, and more preferably over at least about 325 amino acids, and more preferably over at least about 350 amino acids, and more preferably over at least about 375 amino acids, and more preferably over at least about 400 amino acids, and even more preferably, over the full length of the naturally occurring PS receptor amino acid sequences). More preferably, a PS receptor homologue of the present invention has an amino acid sequence that is at least about 316 amino acids in length, and preferably between 316 and 414 amino acids in length, and is at least about 75% identical, and more preferably at least about 80% identical, and even more preferably at least about 85% identical, and even more preferably at least about 90% identical and even more preferably at least about 95% identical, and even more preferably at least about 96% identical, and even more preferably at least about 97% identical, and even more preferably at least about 98% identical, and even more preferably at least about 99% identical to any of SEQ ID NO:3, SEQ ID NO:5, SEQ ID NO:7, SEQ ID NO:9 or SEQ ID NO: 10, over a length of SEQ ID NO:3, SEQ ID NO:5, SEQ ID NO:7, SEQ ID NO:9 or SEQ ID NO:10 that is at least the same as the length of the homologue, as described above.

In another aspect, a PS receptor of the present invention can include a protein comprising, consisting essentially of, or consisting of the amino acid sequence of one of the following fragments of a naturally occurring PS receptor sequence as described herein: (i) a fragment spanning from between about positions 252 and 289 of SEQ ID NO:3 to about position 414 of SEQ ID NO:3 (i.e., one end of the fragment is at one of the positions from 252–289, and the other end of the fragment is at position 414); (ii) a fragment spanning from between about positions 252 and 289 of SEQ ID NO:5 to about position 403 of SEQ ID NO:5; (iii) a fragment spanning from between about positions 206 and 243 of SEQ ID NO:7 to about position 349 of SEQ ID NO:7; (iv) a fragment spanning from between about positions 257 and 294 of SEQ ID NO:9 to about position 408 of SEQ ID NO:9; and (v) a fragment spanning from between about positions 252 and 289 of SEQ ID NO:10 to about position 414 of SEQ ID NO:10. Such PS receptor proteins have PS receptor biological activity in that they are structurally homologous to the full-length proteins over the length of the fragment, and they bind to phosphatidylserine. These fragments represent a soluble PS receptor of the present invention. Preferably, these fragments are from about 106 amino acids in length to about 166 amino acids in length, although intermediate length fragments, as well as fragments that are shorter than 106 amino acids or longer than 166 amino acids, but which retain phosphatidylserine receptor activity of a soluble PS receptor are also encompassed by the present invention. One of skill in the art will recognize that various sizes of soluble PS receptors can be produced that fall around the range of about 106 to about 166 amino acids. According to the present invention, a soluble PS receptor is a fragment of a PS receptor protein of the present invention (including a fragment of a PS receptor homologue), wherein, under normal physiological conditions (e.g., in a solution or buffer at physiological pH), at least about 30%, and more preferably at least about 40%, and more preferably at least about 50%, and more preferably at least about 60%, and more preferably at least about 70%, and more preferably at least about 80%, and more preferably at least about 90%, and even more preferably at least about 95%, of the PS receptor fragment is soluble (in solution).

The present invention also includes homologues of any of the above-identified soluble PS receptor proteins of the present invention, wherein the homologue has PS receptor biological activity as described above for the soluble PS receptors. In one aspect, a homologue of the soluble PS receptor has an amino acid sequence that is at least about 106 to about 166 amino acids in length (the sequence may be longer provided that the PS receptor homologue remains soluble and does not add significant membrane structure of the naturally occurring PS receptor full-length protein), and which is at least about 70% identical to any of the soluble PS receptor fragments of SEQ ID NO:3, SEQ ID NO:5, SEQ ID NO:7, SEQ ID NO:9 or SEQ ID NO:10 described above, over a length of such fragments of SEQ ID NO:3, SEQ ID NO:5, SEQ ID NO:7, SEQ ID NO:9 or SEQ ID NO: 10 that is at least the same as the length of the homologue (i.e., over at least 106 amino acids, and more preferably over at least about 110 amino acids, and more preferably over at least about 115 amino acids, and more preferably over at least about 120 amino acids, and more preferably over at least about 125 amino acids, and more preferably over at least about 130 amino acids, and more preferably over at least about 135 amino acids, and more preferably over at least about 140 amino acids, and more preferably over at least about 145 amino acids, and more preferably over at least about 150 amino acids, and more preferably over at least about 155 amino acids, and more preferably over at least about 160 amino acids, and more preferably over at least about 166 amino acids, of the soluble PS receptor amino acid sequences). More preferably, a PS receptor homologue of the present invention has an amino acid sequence that is at least about 106 to about 166 amino acids in length, and is at least about 75% identical, and more preferably at least about 80% identical, and even more preferably at least about 85% identical, and even more preferably at least about 90% identical and even more preferably at least about 95% identical, and even more preferably at least about 96% identical, and even more preferably at least about 97% identical, and even more preferably at least about 98% identical, and even more preferably at least about 99% identical to any of the soluble PS receptor fragments of SEQ ID NO:3, SEQ ID NO:5, SEQ ID NO:7, SEQ ID NO:9 or SEQ ID NO:10 described above, over a length of such fragments of SEQ ID NO:3, SEQ ID NO:5, SEQ ID NO:7, SEQ ID NO:9 or SEQ ID NO:10 that is at least the same as the length of the homologue, as described above. In one aspect, soluble PS receptors and homologues thereof can be smaller than 106 amino acids (e.g., 95, 90, 85, 80, 75, 70, 65, 60, 55, 50 amino acids in length), wherein the proteins retain soluble PS receptor biological activity as described above.

One embodiment of the present invention relates to an isolated phosphatidylserine receptor homologue, wherein the homologue comprises an amino acid sequence that is: (a) at least about 70% identical to an amino acid sequence selected from the group consisting of SEQ ID NO:3, SEQ ID NO:5, SEQ ID NO:7, SEQ ID NO:9 and SEQ ID NO: 10; and, (b) less than 100% identical to the amino acid sequence of (a). The isolated phosphatidylserine receptor homologue has phosphatidylserine receptor biological activity. Preferably, the homologue is less than about 95% identical to the amino acid sequence of (a). In one embodiment, the homologue is at least about 80% identical and more preferably, at least about 90% identical, to an amino acid sequence selected from the group consisting of SEQ ID NO:3, SEQ ID NO:5, SEQ ID NO:7, SEQ ID NO:9 and SEQ ID NO:10.

As used herein, unless otherwise specified, reference to a percent (%) identity refers to an evaluation of homology which is performed using a BLAST homology search. BLAST homology searches can be performed using the BLAST database and software, which offers search programs including: (1) a BLAST 2.0 Basic BLAST homology search available through the National Center for Biotechnology Information (division of the National Library of Medicine and the National Institutes of Health), using blastp for amino acid searches and blastn for nucleic acid searches with standard default parameters, wherein the query sequence is filtered for low complexity regions by default (described in Altschul, S. F., Madden, T. L., Schäaffer, A. A., Zhang, J., Zhang, Z., Miller, W. & Lipman, D. J. (1997) "Gapped BLAST and PSI-BLAST: a new generation of protein database search programs." Nucleic Acids Res. 25:33 89–3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches.

Two specific sequences can be aligned to one another using BLAST 2 sequence as described in Tatusova and Madden, (1999), "Blast 2 sequences—a new tool for comparing protein and nucleotide sequences", *FEMS Microbiol Lett.* 174:247–250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows. For blastn, using 0 BLOSUM62 matrix:

Reward for match=1

Penalty for mismatch=−2

Open gap (5) and extension gap (2) penalties gap x_dropoff (50) expect (10) word size (11) filter (on)

For blastp, using 0 BLOSUM62 matrix:

Open gap (11) and extension gap (1) penalties gap x_dropoff (50) expect (10) word size (3) filter (on).

In addition, PSI-BLAST provides an automated, easy-to-use version of a "profile" search, which is a sensitive way to look for sequence homologues. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs, although for the direct comparison of two sequences, BLAST 2 is preferred.

A homologue of a naturally occurring phosphatidylserine receptor of the present invention, such as SEQ ID NO:3, SEQ ID NO:5, SEQ ID NO:7, SEQ ID NO:9, can differ from such naturally occurring sequence by as few as one amino acid deletions, insertions or substitutions. In one embodiment, the homologue differs from SEQ ID NO:3, SEQ ID NO: 5, SEQ ID NO:7, or SEQ ID NO:9, by any whole number between 1 and 125 amino acid deletions, insertions or substitutions, and most preferably, by 1, 2, 3, 4, 5, 6, 7, 8, 9, 10, 15, 20, 30, 40, 50, 60, 70, 80, 90, 100, 110, or 120 amino acid deletions, insertions or substitutions, wherein the homologue has phosphatidylserine receptor biological activity.

In one embodiment, the isolated phosphatidylserine receptor of the present invention comprises an amino acid sequence having the consensus sequence represented by SEQ ID NO:10. In another embodiment, the isolated phosphatidylserine receptor comprises an amino acid sequence that aligns with the consensus sequence represented by SEQ ID NO:10 using an alignment program, wherein amino acid residues in said amino acid sequence align with 100% identity with at least about 50%, and preferably at least about 60%, and more preferably at least about 70%, and more preferably at least about 75%, and more preferably at least about 80%, and more preferably at least about 85%, and more preferably at least about 90%, and more preferably at least about 95%, and even more preferably at least about 100%, of the identified consensus residues (i.e., the non-Xaa residues) in SEQ ID NO:10. Sequences can be aligned using the BLAST 2 or PSI-BLAST programs discussed above. Alternatively, sequences can be aligned using the CLUSTAL program. A CLUSTAL alignment program (e.g., CLUSTAL, CLUSTAL V, CLUSTAL W), also available as a module within the at least DNASTAR program, can be used with the following parameters, also referred to herein as the CLUSTAL standard default parameters:

Multiple Alignment Parameters (i.e. for more than 2 sequences):
(1) Gap penalty=10;
(2) Gap length penalty=10;
Pairwise Alignment Parameters (i.e. for two sequences):
(1) Ktuple=1;
(2) Gap penalty=3;
(3) Window=5;
(4) Diagonals saved=5.

A homologue of a PS receptor can also include proteins of at least about 316 amino acids in length, and preferably between 316 amino acids and 414 amino acids in length, wherein the homologue has PS receptor biological activity, and has an amino acid sequence comprising at least 25 contiguous amino acid residues of any of SEQ ID NO:3, SEQ ID NO:5, SEQ ID NO:7, SEQ ID NO:9 or SEQ ID NO:10 (i.e., 25 contiguous amino acid residues having 100% identity with 25 contiguous amino acids of any of SEQ ID NO:3, SEQ ID NO:5, SEQ ID NO:7, SEQ ID NO:9 or SEQ ID NO:10). In a preferred embodiment, a homologue of a PS receptor of the present invention includes proteins of at least about 316 amino acids in length, and preferably between 316 amino acids and 414 amino acids in length, having amino acid sequences comprising at least 50, and more preferably at least 75, and more preferably at least 100, and more preferably at least 115, and more preferably at least 130, and more preferably at least 150, and more preferably at least 200, and more preferably, at least 250, and more preferably, at least 300, and more preferably, at least 350, and more preferably, at least 400, contiguous amino acid residues of any of SEQ ID NO:3, SEQ ID NO:5, SEQ ID NO:7, SEQ ID NO:9 or SEQ ID NO:10. In one aspect, such structural characteristics can further define the PS receptor homologues described above (i.e., the homologues defined on the basis of percent identity to naturally occurring PS receptors).

A homologue of a soluble PS receptor as described above can also include proteins of at least about 106 to about 166 amino acids in length having biological activity of a soluble PS receptor, and having an amino acid sequence comprising at least 25 contiguous amino acid residues of any of the soluble PS receptor fragments of SEQ ID NO:3, SEQ ID NO:5, SEQ ID NO:7, SEQ ID NO:9 or SEQ ID NO:10 described above. Preferably, a homologue of a soluble PS receptor as described above can also include proteins of at least 106 to about 166 amino acids in length having biological activity of a soluble PS receptor, and having an amino acid sequence comprising at least 50, and more preferably at least 75, and more preferably at least 100, and more preferably at least 125, and more preferably at least 150, contiguous amino acid residues of any of the soluble PS receptor fragments of SEQ ID NO:3, SEQ ID NO:5, SEQ ID NO:7, SEQ ID NO:9 or SEQ ID NO:10 described above.

According to the present invention, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" with a second sequence means that the first sequence exactly matches the second sequence with no gaps between nucleotides or amino acids.

In another embodiment, an isolated PS receptor of the present invention, including an isolated PS receptor homologue, includes a protein having an amino acid sequence that is sufficiently similar to a naturally occurring PS receptor amino acid sequence that a nucleic acid sequence encoding the homologue is capable of hybridizing under moderate, high, or very high stringency conditions (described below) to (i.e., with) a nucleic acid molecule encoding the naturally occurring PS receptor (i.e., to the complement of the nucleic acid strand encoding the naturally occurring PS receptor amino acid sequence). Preferably, a PS receptor (including a homologue) is encoded by a nucleic acid sequence that hybridizes under moderate, high or very high stringency conditions to the complement of a nucleic acid sequence that encodes a protein comprising an amino acid sequence represented by SEQ ID NO:3, SEQ ID NO:5, SEQ ID NO:7, SEQ ID NO:9 or SEQ ID NO:10, wherein the PS receptor-encoding nucleic acid sequence is between 948 and 1242 nucleotides in length. Even more preferably, a PS receptor protein of the present invention is encoded by a nucleic acid sequence that hybridizes under moderate, high or very high stringency conditions to the complement of SEQ ID NO:2, SEQ ID NO:4, SEQ ID NO:6, or SEQ ID NO:8, wherein the PS receptor-encoding nucleic acid sequence is between 948 and 1242 nucleotides in length. In one aspect, a PS receptor is encoded by a nucleic acid sequence that hybridizes under moderate, high or very high stringency conditions to the complement of a nucleic acid sequence that encodes a protein comprising an amino acid sequence represented by the soluble PS receptor fragments of SEQ ID NO:3, SEQ ID NO:5, SEQ ID NO:7, SEQ ID NO:9 or SEQ ID NO:10, described above, wherein the PS receptor-encoding nucleic acid sequence is between 948 and 1242 nucleotides in length. In yet another aspect, a PS receptor protein of the present invention is encoded by a nucleic acid sequence that hybridizes under moderate, high or very high stringency conditions to the complement of nucleotides from between 756 and 867 to 1242 of SEQ ID NO:2, nucleotides from between 756 and 867 to 1209 of SEQ ID NO:4, nucleotides from between 618 and 729 to 1047 of SEQ ID NO:6, or nucleotides from between 771 and 882 to 1224 of SEQ ID NO:8, wherein the PS receptor-encoding nucleic acid sequence is between about 106 and about 166 nucleotides in length. Such hybridization conditions are described in detail below. A nucleic acid sequence complement of nucleic acid sequence encoding a PS receptor of the present invention refers to the nucleic acid sequence of the nucleic acid strand that is complementary to the strand which encodes the PS receptor. It will be appreciated that a double stranded DNA which encodes a given amino acid sequence comprises a single strand DNA and its complementary strand having a sequence that is a complement to the single strand DNA. As such, nucleic acid molecules of the present invention can be either double-stranded or single-stranded, and include those nucleic acid molecules that form stable hybrids under stringent hybridization conditions with a nucleic acid sequence that encodes the amino acid sequence SEQ ID NO:3, SEQ ID NO:5, SEQ ID NO:7, SEQ ID NO:9 or SEQ ID NO:10, and/or with the complement of the nucleic acid sequence that encodes any of such amino acid sequences. Methods to deduce a complementary sequence are known to those skilled in the art. It should be noted that since amino acid sequencing and nucleic acid sequencing technologies are not entirely error-free, the sequences presented herein, at best, represent apparent sequences of a PS receptor of the present invention.

In one embodiment, PS receptor homologues can be the result of natural allelic variation or natural mutation. In one embodiment, PS receptor homologues can be proteins that are structurally and/or functionally highly homologous to the mammalian PS receptor proteins described herein (i.e., from human and mouse), but that are naturally occurring proteins from different organisms, such as the C. elegans and Drosophila PS receptor homologues identified by the present inventors. PS receptor homologues of the present invention can also be produced using techniques known in the art including, but not limited to, direct modifications to the protein or modifications to the gene encoding the protein using, for example, classic or recombinant DNA techniques to effect random or targeted mutagenesis. A naturally occurring allelic variant of a nucleic acid encoding a PS receptor is a gene that occurs at essentially the same locus (or loci) in the genome as the gene which encodes a PS receptor amino acid sequence described herein, but which, due to natural variations caused by, for example, mutation or recombination, has a similar but not identical sequence. Natural allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

PS receptor proteins of the present invention also include expression products of gene fusions (for example, used to overexpress soluble, active forms of the recombinant protein), of mutagenized genes (such as genes having codon modifications to enhance gene transcription and translation), and of truncated genes (such as genes having membrane binding domains removed to generate soluble forms of the membrane protein, or genes having signal sequences removed which are poorly tolerated in a particular recombinant host).

The minimum size of a PS receptor protein and/or homologue of the present invention is a size sufficient to have PS receptor biological activity (e.g., bind to phosphatidylserine). Preferably, a protein of the present invention is at least about 50 amino acids in length, and more preferably at least about 60, and more preferably at least about 70, and more preferably at least about 80, and more preferably at least about 90, and more preferably at least about 100, and more preferably at least about 106 amino acids long, and more preferably at least about 110, and more preferably at least 120, and more preferably at least about 130, and more preferably at least about 140, and more preferably at least about 150, and more preferably at least about 175, and more preferably at least about 200, and more preferably at least about 225, and more preferably at least about 250, and more preferably at least about 275, and more preferably at least about 300, and more preferably at least about 325, and more preferably at least about 350, and more preferably at least about 375, and more preferably at least about 400 amino acids long. There is no limit, other than a practical limit, on the maximum size of such a protein in that the protein can include a portion of a PS receptor protein or a full-length PS receptor, plus additional sequence (e.g., a fusion protein sequence or a heterologous sequence), if desired.

The present invention also includes a fusion protein that includes a PS receptor-containing domain (i.e., an amino acid sequence for a PS receptor according to the present invention, including a PS receptor fragment or other homologue) attached to one or more fusion segments. Suitable fusion segments for use with the present invention include, but are not limited to, segments that can: enhance a protein's stability; provide other desirable biological activity; and/or assist with the purification of an PS receptor (e.g., by affinity chromatography). A suitable fusion segment can be a domain of any size that has the desired function (e.g., imparts increased stability, solubility, action or biological activity; and/or simplifies purification of a protein). Fusion segments can be joined to amino and/or carboxyl termini of the PS receptor-containing domain of the protein and can be susceptible to cleavage in order to enable straight-forward recovery of a PS receptor. Fusion proteins are preferably produced by culturing a recombinant cell transfected with a fusion nucleic acid molecule that encodes a protein including the fusion segment attached to either the carboxyl and/or amino terminal end of a PS receptor-containing domain.

The present invention also includes a mimetic of a PS receptor. As used herein, the term "mimetic" is used to refer to any peptide or non-peptide compound that is able to mimic the biological action of a naturally occurring peptide, often because the mimetic has a basic structure that mimics the basic structure of the naturally occurring peptide and/or has the salient biological properties of the naturally occurring peptide. Minetics can include, but are not limited to: peptides that have substantial modifications from the prototype such as no side chain similarity with the naturally occurring peptide (such modifications, for example, may decrease its susceptibility to degradation); anti-idiotypic and/or catalytic antibodies, or fragments thereof; non-proteinaceous portions of an isolated protein (e.g., carbohydrate structures); or synthetic or natural organic molecules, including nucleic acids and drugs identified through combinatorial chemistry, for example. Such mimetics can be designed, selected and/or otherwise identified using a variety of methods known in the art, such methods being described below with regard to agonists and antagonists of PS receptors of the present invention.

In one embodiment of the present invention, any of the above-described PS receptor proteins, including the PS receptor homologues, can be produced with from at least one, and up to about 20, additional heterologous amino acids flanking each of the C- and/or N-terminal end of the PS receptor protein. Such a protein can be referred to as "consisting essentially of" a given PS receptor amino acid sequence. According to the present invention, the heterologous amino acids are a sequence of amino acids that are not naturally found (i.e., not found in nature, in vivo) flanking the PS receptor sequence or which would not be encoded by the nucleotides that flank the naturally occurring PS receptor nucleic acid sequence as it occurs in the gene, if such nucleotides in the naturally occurring sequence were translated using standard codon usage for the organism from which the PS receptor is derived. Similarly, the phrase "consisting essentially of", when used with reference to a nucleic acid sequence herein, refers to a nucleic acid sequence encoding a PS receptor (including fragments/homologues) that can be flanked by from at least one, and up to as many as about 60, additional heterologous nucleotides at each of the 5' and/or the 3' end of the nucleic acid sequence encoding the PS receptor. The nucleotides are not naturally found (i.e., not found in nature, in vivo) flanking the PS receptor coding sequence as it occurs in the natural gene.

Further embodiments of the present invention include nucleic acid molecules that encode a PS receptor protein or homologue thereof. A nucleic acid molecule of the present invention includes a nucleic acid molecule comprising a nucleic acid sequence encoding any of the isolated PS receptor proteins, including a PS receptor homologue, described above. One embodiment of the present invention relates to an isolated cDNA or RNA molecule (referred to generically as an isolated nucleic acid molecule or isolated nucleotide) selected from the group consisting of:

(a) a nucleic acid sequence encoding a phosphatidylserine receptor protein comprising, consisting essentially of, or consisting of, an amino acid sequence selected from the group consisting of SEQ ID NO:3, SEQ ID NO:5, SEQ ID NO:7, SEQ ID NO:9 and SEQ ID NO:10;

(b) a nucleic acid sequence encoding a homologue of the protein of (a), wherein said homologue comprises, consists essentially of, or consists of, an amino acid sequence that is at least 316 amino acids in length, and preferably between 316 and 414 amino acid residues in length, and that is at least about 70% identical to said amino acid sequence of (a);

(c) a nucleic acid sequence encoding a protein comprising, consisting essentially of, or consisting of, a fragment of said amino acid sequence of (a) selected from the group consisting of: (i) a fragment spanning from between about positions 252 and 289 of SEQ ID NO:3 to position 414 of SEQ ID NO:3; (ii) a fragment spanning from between about positions 252 and 289 of SEQ ID NO:5 to position 403 of SEQ ID NO:5; (iii) a fragment spanning from between about positions 206 and 243 of SEQ ID NO:7 to position 349 of SEQ ID NO:7; (iv) a fragment spanning from between about positions 257 and 294 of SEQ ID NO:9 to position 408 of SEQ ID NO:9; and (v) a fragment spanning from between about positions 252 and 289 of SEQ ID NO:10 to position 414 of SEQ ID NO:10;

(d) a nucleic acid sequence encoding a homologue of the protein of (c), wherein said wherein said homologue comprises, consists essentially of, or consists of, an amino acid sequence that is from 106 to 166 amino acids in length and that is at least about 70% identical to said amino acid sequence of (c); and (e) a nucleic acid sequence that is fully complementary to said nucleic acid sequence of (a), (b), (c) or (d).

In one embodiment, an isolated nucleic acid molecule consists of a nucleic acid sequence encoding one of the following amino acid sequences: SEQ ID NO:3, SEQ ID NO:5, SEQ ID NO:7, SEQ ID NO:9 and SEQ ID NO:10. In a preferred embodiment, the nucleic acid sequence is selected from the group of SEQ ID NO:2, SEQ ID NO:4, SEQ ID NO:6 and SEQ ID NO:8.

In one aspect, a nucleic acid molecule of the present invention comprises, consists essentially of, or consists of a nucleic acid sequence encoding an amino acid sequence that is at least 316 amino acids in length, and preferably between 316 and 414 amino acids in length, and which is at least about 70% identical to any of SEQ ID NO:3, SEQ ID NO:5, SEQ ID NO:7, SEQ ID NO:9 or SEQ ID NO:10, over a length of SEQ ID NO:3, SEQ ID NO:5, SEQ ID NO:7, SEQ ID NO:9 or SEQ ID NO:10 that is at least the same as the length of the protein encoded by the referenced nucleic acid sequence (i.e., over at least 316 amino acids, and more preferably over at least about 325 amino acids, and more preferably over at least about 350 amino acids, and more preferably over at least about 375 amino acids, and more preferably over at least about 400 amino acids, and even more preferably, over the full length of the naturally occurring PS receptor amino acid sequences). More preferably, such a nucleic acid sequence encodes an amino acid sequence that is between 316 and 414 amino acids in length, and is at least about 75% identical, and more preferably at least about 80% identical, and even more preferably at least about 85% identical, and even more preferably at least about 90% identical and even more preferably at least about 95% identical, and even more preferably at least about 96% identical, and even more preferably at least about 97% identical, and even more preferably at least about 98% identical, and even more preferably at least about 99% identical to any of SEQ ID NO:3, SEQ ID NO:5, SEQ ID NO:7, SEQ ID NO:9 or SEQ ID NO:10, over a length of SEQ ID NO:3, SEQ ID NO:5, SEQ ID NO:7, SEQ ID NO:9 or SEQ ID NO:10 that is at least the same as the length of the protein encoded by the referenced nucleic acid sequence, as described above.

In one embodiment, an isolated nucleic acid molecule of the present invention that encodes a PS receptor homologue comprises, consists essentially of, or consists of, a nucleic acid sequence that is at least 948 nucleotides in length, and preferably between 948 and 1242 nucleotides in length, and that is at least about 70% identical to a nucleic acid sequence selected from the group of SEQ ID NO:2, SEQ ID NO:4, SEQ ID NO:6 or SEQ ID NO:8, over a length of SEQ ID NO:2, SEQ ID NO:4, SEQ ID NO:6 or SEQ ID NO:8 that is at least the same as the length of the nucleic acid sequence encoding the PS receptor homologue. More preferably, such a nucleic acid sequence is at least about 75% identical, and more preferably at least about 80% identical, and even more preferably at least about 85% identical, and even more preferably at least about 90% identical and even more preferably at least about 95% identical, and even more preferably at least about 96% identical, and even more preferably at least about 97% identical, and even more preferably at least about 98% identical, and even more preferably at least about 99% identical to any of SEQ ID NO:2, SEQ ID NO:4, SEQ ID NO:6 or SEQ ID NO:8, over a length of SEQ ID NO:2, SEQ ID NO:4, SEQ ID NO:6 or SEQ ID NO:8 that is at least the same as the length of the nucleic acid sequence encoding the PS receptor homologue.

In another aspect, an isolated nucleic acid molecule of the present invention comprises, consists essentially of, or consists of a nucleic acid sequence encoding a protein consisting of the amino acid sequence of one of the following fragments of a naturally occurring PS receptor sequence as described herein: (i) a fragment spanning from between about positions 252 and 289 of SEQ ID NO:3 to position 414 of SEQ ID NO:3; (ii) a fragment spanning from between about positions 252 and 289 of SEQ ID NO:5 to position 403 of SEQ ID NO:5; (iii) a fragment spanning from between about positions 206 and 243 of SEQ ID NO:7 to position 349 of SEQ ID NO:7; (iv) a fragment spanning from between about positions 257 and 294 of SEQ ID NO:9 to position 408 of SEQ ID NO:9; and (v) a fragment spanning from between about positions 252 and 289 of SEQ ID NO:10 to position 414 of SEQ ID NO:10. Such PS receptor proteins have PS receptor biological activity in that they are structurally homologous to the full-length proteins over the length of the fragment, and they bind to phosphatidylserine. In one embodiment, an isolated nucleic acid molecule of the present invention comprises, consists essentially of, or consists of, a nucleic acid sequence selected from the group of: (i) a fragment spanning from between about nucleotides 756 and 867 of SEQ ID NO:2 to nucleotide 1242 of SEQ ID NO:2; (ii) a fragment spanning from between about nucleotides 756 and 867 of SEQ ID NO:4 to nucleotide 1209 of SEQ ID NO:4; (iii) a fragment spanning from between about nucleotides 618 and 729 of SEQ ID NO:6 to nucleotide 1047 of SEQ ID NO:6; or (iv) a fragment spanning from between about nucleotides 771 and 882 of SEQ ID NO:8 to nucleotide 1224 of SEQ ID NO:8.

The present invention also includes isolated nucleic acid molecules comprising, consisting essentially of, or consisting of, nucleic acid sequences encoding homologues of any of the above-identified soluble PS receptor proteins of the present invention, wherein the homologue has PS receptor biological activity as described above for the soluble PS receptors. In one aspect, such a nucleic acid sequence encodes an amino acid sequence that is at least about 106 to about 166 amino acids in length and which is at least about 70% identical to any of the soluble PS receptor fragments of SEQ ID NO:3, SEQ ID NO:5, SEQ ID NO:7, SEQ ID NO:9 or SEQ ID NO:10 described above, over a length of such fragments of SEQ ID NO:3, SEQ ID NO:5, SEQ ID NO:7, SEQ ID NO:9 or SEQ ID NO:10 that is at least the same as the length of the homologue (i.e., over at least 106 amino acids, and more preferably over at least about 110 amino acids, and more preferably over at least about 115 amino acids, and more preferably over at least about 120 amino acids, and more preferably over at least about 125 amino acids, and more preferably over at least about 130 amino acids, and more preferably over at least about 135 amino acids, and more preferably over at least about 140 amino acids, and more preferably over at least about 145 amino acids, and more preferably over at least about 150 amino acids, and more preferably over at least about 155 amino acids, and more preferably over at least about 160 amino acids, and more preferably over at least about 166 amino acids, of the soluble PS receptor amino acid sequences). More preferably, such a nucleic acid sequence encodes an amino acid sequence that is at least about 106 to about 166 amino acids in length, and is at least about 75% identical, and more preferably at least about 80% identical, and even more preferably at least about 85% identical, and even more preferably at least about 90% identical and even more preferably at least about 95% identical, and even more preferably at least about 96% identical, and even more preferably at least about 97% identical, and even more preferably at least about 98% identical, and even more preferably at least about 99% identical to any of the soluble PS receptor fragments of SEQ ID NO:3, SEQ ID NO:5, SEQ ID NO:7, SEQ ID NO:9 or SEQ ID NO:10 described above, over a length of such fragments of SEQ ID NO:3, SEQ ID NO:5, SEQ ID NO:7, SEQ ID NO:9 or SEQ ID NO:10 that is at least the same as the length of the homologue, as described above. In one aspect, such nucleic acid sequences encode soluble PS receptors and homologues thereof that are smaller than 106 amino acids (e.g., 95, 90, 85, 80, 75, 70, 65, 60, 55, 50 amino acids in length), wherein the proteins retain soluble PS receptor biological activity as described above.

In another aspect, such a nucleic acid sequence includes a sequence that is at least about 318 to about 498 nucleotides in length, that is at least about 70% identical to a nucleic acid sequence selected from the group of (i) a fragment spanning from between about nucleotides 756 and 867 of SEQ ID NO:2 to nucleotide 1242 of SEQ ID NO:2; (ii) a fragment spanning from between about nucleotides 756 and 867 of SEQ ID NO:4 to nucleotide 1209 of SEQ ID NO:4; (iii) a fragment spanning from between about nucleotides 618 and 729 of SEQ ID NO:6 to nucleotide 1047 of SEQ ID NO:6; or (iv) a fragment spanning from between about nucleotides 771 and 882 of SEQ ID NO:8 to nucleotide 1224 of SEQ ID NO:8, over a length of such fragments that is at least the same as the length of the reference sequence (i.e., over at least 318 nucleotides, and more preferably over at least about 330 nucleotides, and more preferably over at least about 345 nucleotides, and more preferably over at least about 360 nucleotides, and more preferably over at least about 375 nucleotides, and more preferably over at least about 390 nucleotides, and more preferably over at least about 405 nucleotides, and more preferably over at least about 420 nucleotides, and more preferably over at least about 435 nucleotides, and more preferably over at least about 450 nucleotides, and more preferably over at least about 465 nucleotides, and more preferably over at least about 480 nucleotides, and more preferably over at least about 498 nucleotides, of the above-identified nucleotide fragments encoding soluble PS receptor amino acid sequences). More preferably, such a nucleic acid sequence encodes an amino acid sequence that is at least about 318 to about 498 nucleotides in length, and is at least about 75% identical, and more preferably at least about 80% identical, and even more preferably at least about 85% identical, and even more preferably at least about 90% identical and even more preferably at least about 95% identical, and even more preferably at least about 96% identical, and even more preferably at least about 97% identical, and even more preferably at least about 98% identical, and even more preferably at least about 99% identical to any of the above-identified nucleotide fragments encoding soluble PS receptor amino acid sequences.

In another aspect, an isolated nucleic acid molecule of the present invention comprises, consists essentially of, or consists of a nucleic acid sequence of at least 948 nucleotides in length, and preferably between 948 and 1242 nucleotides in length that encodes a homologue of a PS receptor having PS receptor biological activity, wherein the amino acid sequence of the PS receptor homologue comprises at least 25 contiguous amino acid residues of any of SEQ ID NO:3, SEQ ID NO:5, SEQ ID NO:7, SEQ ID NO:9 or SEQ ID NO:10. In a preferred embodiment, an isolated nucleic acid molecule of the present invention comprises, consists essentially of, or consists of a nucleic acid sequence of at least 948 nucleotides in length, and preferably between 948 and 1242 nucleotides in length, that encodes a homologue of a PS receptor having PS receptor biological activity, wherein the amino acid sequence of the PS receptor homologue comprises at least 50, and more preferably at least 75, and more preferably at least 100, and more preferably at least 115, and more preferably at least 130, and more preferably at least 150, and more preferably at least 200, and more preferably, at least 250, and more preferably, at least 300, and more preferably, at least 350, and more preferably, at least 400, contiguous amino acid residues of any of SEQ ID NO:3, SEQ ID NO:5, SEQ ID NO:7, SEQ ID NO:9 or SEQ ID NO:10. In another aspect, an isolated nucleic acid molecule of the present invention comprises, consists essentially of, or consists of a nucleic acid sequence of at least 948 nucleotides in length, and preferably between 948 and 1242 nucleotides in length that encodes a homologue of a PS receptor having PS receptor biological activity, wherein the amino acid sequence of the PS receptor homologue comprises at least 75, and more preferably at least 150, and more preferably at least 225, and more preferably at least 300, and more preferably at least 345, and more preferably at least 390, and more preferably at least 450, and more preferably at least 600, and more preferably, at least 750, and more preferably, at least 900, and more preferably, at least 1050, and more preferably, at least 1200, contiguous nucleotides of a nucleic acid sequence selected from the group of SEQ ID NO:2, SEQ ID NO:4, SEQ ID NO:6, SEQ ID NO:8.

In one embodiment, isolated nucleic acid molecules of the present invention include isolated nucleic acid molecules that hybridize under low stringency conditions, and more preferably under moderate stringency conditions, and even more preferably under high stringency conditions, and even more preferably under very high stringency conditions with the complement of a nucleic acid sequence encoding a naturally occurring PS receptor (i.e., including naturally occurring allelic variants and fragments encoding a PS receptor). Preferably, an isolated nucleic acid molecule encoding a PS receptor protein of the present invention (including PS receptor homologues) comprises, consists essentially of, or consists of, a nucleic acid sequence that hybridizes under low, moderate, high, or very high stringency conditions to the complement of a nucleic acid sequence that encodes a PS receptor protein consisting of an amino acid sequence represented by SEQ ID NO:3, SEQ ID NO:5, SEQ ID NO:7, SEQ ID NO:9, SEQ ID NO:10, or functional fragments thereof. In one embodiment, an isolated nucleic acid molecule comprises, consists essentially of, or consists of, a nucleic acid sequence that hybridizes under low, moderate, high or very high stringency conditions to the complement of a nucleic acid sequence represented by SEQ ID NO:2, SEQ ID NO:4, SEQ ID NO:6, SEQ ID NO:8, or fragments thereof encoding functional PS receptors (e.g., soluble PS receptors).

As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267–284; Meinkoth et al., ibid., is incorporated by reference herein in its entirety.

More particularly, low stringency hybridization and washing conditions, as referred to herein, refer to conditions which permit isolation of nucleic acid molecules having at least about 50% nucleic acid sequence identity with the nucleic acid molecule being used to probe in the hybridization reaction (i.e., conditions permitting about 50% or less mismatch of nucleotides). Moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C., more preferably, between about 28° C. and about 40° C., and even more preferably, between about 35° C. and about 45° C. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62.

In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., MRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein.

Preferably, an isolated nucleic acid molecule of the present invention is produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect on PS receptor biological activity. Allelic variants and protein homologues (e.g., proteins encoded by nucleic acid homologues) have been discussed in detail above.

A nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

The minimum size of a nucleic acid molecule of the present invention is a size sufficient to encode a PS receptor protein having the desired biological activity, or sufficient to form a probe or oligonucleotide primer that is capable of forming a stable hybrid with the complementary sequence of a nucleic acid molecule encoding the natural protein (e.g., under moderate, high or very high stringency conditions). As such, the size of the nucleic acid molecule encoding such a protein can be dependent on nucleic acid composition and percent homology or identity between the nucleic acid molecule and complementary sequence as well as upon hybridization conditions per se (e.g., temperature, salt concentration, and formamide concentration). The minimal size of a nucleic acid molecule that is used as an oligonucleotide primer or as a probe is typically at least about 12 to about 15 nucleotides in length if the nucleic acid molecules are GC-rich and at least about 15 to about 18 bases in length if they are AT-rich. There is no limit, other than a practical limit, on the maximal size of a nucleic acid molecule of the present invention, in that the nucleic acid molecule can include a portion of a protein-encoding sequence (e.g., a PS receptor-encoding sequence) or a nucleic acid sequence encoding a full-length protein. Preferred lengths of nucleic acid sequences and PS receptor proteins encoded by such sequences have been described previously herein.

One embodiment of the present invention is a recombinant nucleic acid molecule comprising an isolated nucleic acid molecule of the present invention. According to the present invention, a recombinant nucleic acid molecule includes at least one isolated nucleic acid molecule of the present invention that is linked to a heterologous nucleic acid sequence. Such a heterologous nucleic acid sequence is typically a recombinant nucleic acid vector (e.g., a recombinant vector) which is suitable for cloning, sequencing, and/or otherwise manipulating the nucleic acid molecule, such as by expressing and/or delivering the nucleic acid molecule into a host cell to form a recombinant cell. Such a vector contains heterologous nucleic acid sequences, that is nucleic acid sequences that are not naturally found adjacent to nucleic acid molecules of the present invention, although the vector can also contain regulatory nucleic acid sequences (e.g., promoters, untranslated regions) which are naturally found adjacent to nucleic acid molecules of the present invention (discussed in detail below). The vector can be either RNA or DNA, either prokaryotic or eukaryotic, and typically is a virus or a plasmid. The vector can be maintained as an extrachromosomal element (e.g., a plasmid) or it can be integrated into the chromosome. The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. As used herein, the phrase "recombinant nucleic acid molecule" is used primarily to refer to a recombinant vector into which has been ligated the nucleic acid sequence to be cloned, manipulated, transformed into the host cell (i.e., the insert).

In one embodiment, a recombinant vector of the present invention is an expression vector, such that the recombinant nucleic molecule produced by inserting a nucleic acid molecule into the vector can be used to express, or produce the protein encoded by the nucleic acid molecule insert. As used herein, the phrase "expression vector" is used to refer to a vector that is suitable for production of an encoded product (e.g., a protein of interest). More particularly, a nucleic acid sequence encoding the product to be produced (e.g., a PS receptor) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector which enable the transcription and translation of the nucleic acid sequence when the recombinant molecule is introduced into a host cell.

According to the present invention, the phrase "operatively linked" refers to linking a nucleic acid molecule to a transcription control sequence in a manner such that the molecule is able to be expressed when transfected (i.e., transformed, transduced, transfected, conjugated or conduced) into a host cell. Transcription control sequences are sequences which control the initiation, elongation, or termination of transcription. Particularly important transcription control sequences are those which control transcription initiation, such as promoter, enhancer, operator and repressor sequences. Suitable transcription control sequences include any transcription control sequence that can function in at least one of the recombinant cells useful for expressing a PS receptor protein of the present invention. A variety of such transcription control sequences are known to those skilled in the art. Preferred transcription control sequences include those which function in bacterial, fungal (e.g., yeast), insect, plant or animal cells, and particularly, in mammalian cells including, but not limited to, monocytes or macrophages.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention, including those which are integrated into the host cell chromosome, also contains secretory signals (i.e., signal segment nucleic acid sequences) to enable an expressed PS receptor protein to be secreted from the cell that produces the protein. Suitable signal segments include a signal segment that is naturally associated with a PS receptor protein of the present invention or any heterologous signal segment capable of directing the secretion of a PS receptor protein according to the present invention. In another embodiment, a recombinant molecule of the present invention comprises a leader sequence to enable an expressed PS receptor protein to be delivered to and inserted into the membrane of a host cell. Suitable leader sequences include a leader sequence that is naturally associated with a PS receptor protein of the present invention, or any heterologous leader sequence capable of directing the delivery and insertion of a PS receptor protein to the membrane of a cell.

One or more recombinant molecules of the present invention can be used to produce an encoded product (e.g., a PS receptor protein) of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include, but are not limited to, any bacterial, fungal (e.g., yeast), insect, plant or animal cell that can be transfected. Host cells can be either untransfected cells or cells that are already transfected with at least one nucleic acid molecule.

According to the present invention, the term "transfection" is used to refer to any method by which an exogenous nucleic acid molecule (i.e., a recombinant nucleic acid molecule) can be inserted into the cell. The term "transformation" can be used interchangeably with the term "transfection" when such term is used to refer to the introduction of nucleic acid molecules into microbial cells, such as bacteria and yeast. In microbial systems, the term "transformation" is used to describe an inherited change due to the acquisition of exogenous nucleic acids by the microorganism and is essentially synonymous with the term "transfection". However, in animal cells, transformation has acquired a second meaning which can refer to changes in the growth properties of cells in culture after they become cancerous, for example. Therefore, to avoid confusion, the term "transfection" is preferably used with regard to the introduction of exogenous nucleic acids into animal cells, and the term "transfection" will be used herein to generally encompass both transfection of animal cells and transformation of microbial cells, to the extent that the terms pertain to the introduction of exogenous nucleic acids into a cell. Therefore, transfection techniques include, but are not limited to, transformation, electroporation, microinjection, lipofection, adsorption, infection and protoplast fusion.

In one embodiment, an isolated PS receptor protein of the present invention is produced by culturing a cell that expresses the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce a PS receptor protein of the present invention. Such medium typically comprises an aqueous medium having assimilable carbon, nitrogen and phosphate sources, and appropriate salts, minerals, metals and other nutrients, such as vitamins. Examples of suitable media and culture conditions are discussed in detail in the Examples section. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell; be secreted into the culture medium; be secreted into a space between two cellular membranes, such as the periplasmic space in *E. coli*; or be retained on the outer surface of a cell or viral membrane. The phrase "recovering the protein" refers to collecting the whole culture medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Proteins of the present invention are preferably retrieved, obtained, and/or used in "substantially pure" form. As used herein, "substantially pure" refers to a purity that allows for the effective use of the protein in vitro, ex vivo or in vivo according to the present invention. For a protein to be useful in an in vitro, ex vivo or in vivo method according to the present invention, it is substantially free of contaminants, other proteins and/or chemicals that might interfere or that would interfere with its use in a method disclosed by the present invention, or that at least would be undesirable for inclusion with the PS receptor protein when it is used in a method disclosed by the present invention. Such methods include antibody production, agonist/antagonist identification assays, preparation of therapeutic compositions, administration in a therapeutic composition, and all other methods disclosed herein. Preferably, a "substantially pure" protein, as referenced herein, is a protein that can be produced by any method (i.e., by direct purification from a natural source, recombinantly, or synthetically), and that has been purified from other protein components such that the phosphatidylserine receptor protein comprises at least about 80% weight/weight of the total protein in a given composition (e.g., the PS receptor is about 80% of the protein in a solution/composition/buffer), and more preferably, at least about 85%, and more preferably at least about 90%, and more preferably at least about 91%, and more preferably at least about 92%, and more preferably at least about 93%, and more preferably at least about 94%, and more preferably at least about 95%, and more preferably at least about 96%, and more preferably at least about 97%, and more preferably at least about 98%, and more preferably at least about 99%, weight/weight of the total protein in a given composition.

One embodiment of the present invention relates to an antibody or antigen binding fragment that selectively binds to a PS receptor of the present invention. Such an antibody can selectively bind to any of the PS receptor proteins described herein, including fragments and other homologues of such receptors. According to the present invention, the phrase "selectively binds to" refers to the ability of an antibody, antigen binding fragment or binding partner of the present invention to preferentially bind to specified proteins (e.g., a PS receptor of the present invention). More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.

Antibodies are characterized in that they comprise immunoglobulin domains and as such, they are members of the immunoglobulin superfamily of proteins. Generally speaking, an antibody molecule comprises two types of chains. One type of chain is referred to as the heavy or H chain and the other is referred to as the light or L chain. The two chains are present in an equimolar ratio, with each antibody molecule typically having two H chains and two L chains. The two H chains are linked together by disulfide bonds and each H chain is linked to a L chain by a disulfide bond. There are only two types of L chains referred to as lambda (λ) and kappa (κ) chains. In contrast, there are five major H chain classes referred to as isotypes. The five classes include immunoglobulin M (IgM or $\mu$), immunoglobulin D (IgD or δ), immunoglobulin G (IgG or λ), immunoglobulin A (IgA or α), and immunoglobulin E (IgE or ε). The distinctive characteristics between such isotypes are defined by the constant domain of the immunoglobulin and are discussed in detail below. Human immunoglobulin molecules comprise nine isotypes, IgM, IgD, IgE, four subclasses of IgG including IgG1 (γ1), IgG2 (γ2), IgG3 (γ3) and IgG4 (γ4), and two subclasses of IgA including IgA1 (α1) and IgA2 (α2).

Each H or L chain of an immunoglobulin molecule comprises two regions referred to as L chain variable domains ($V_L$ domains) and L chain constant domains ($C_L$ domains), and H chain variable domains ($V_H$ domains) and H chain constant domains ($C_H$ domains). A complete $C_H$ domain comprises three sub-domains (CH1, CH2, CH3) and a hinge region. Together, one H chain and one L chain can form an arm of an immunoglobulin molecule having an immunoglobulin variable region. A complete immunoglobulin molecule comprises two associated (e.g., di-sulfide linked) arms. Thus, each arm of a whole immunoglobulin comprises a $V_{H+L}$ region, and a $C_{H+L}$ region. As used herein, the term "variable region" or "V region" refers to a $V_{H+L}$ region (also known as an Fv fragment), a $V_L$ region or a $V_H$ region. Also as used herein, the term "constant region" or "C region" refers to a $C_{H+L}$ region, a $C_L$ region or a $C_H$ region.

Limited digestion of an immunoglobulin with a protease may produce two fragments. An antigen binding fragment is referred to as an Fab, an Fab', or an F(ab')$_2$ fragment. A fragment lacking the ability to bind to antigen is referred to as an Fc fragment. An Fab fragment comprises one arm of an immunoglobulin molecule containing a L chain ($V_L$+$C_L$ domains) paired with the $V_H$ region and a portion of the $C_H$ region (CH1 domain). An Fab' fragment corresponds to an Fab fragment with part of the hinge region attached to the CH1 domain. An F(ab')$_2$ fragment corresponds to two Fab' fragments that are normally covalently linked to each other through a di-sulfide bond, typically in the hinge regions.

The $C_H$ domain defines the isotype of an immunoglobulin and confers different functional characteristics depending upon the isotype. For example, $\mu$ constant regions enable the formation of pentameric aggregates of IgM molecules and α constant regions enable the formation of dimers.

The antigen specificity of an immunoglobulin molecule is conferred by the amino acid sequence of a variable, or V, region. As such, V regions of different immunoglobulin molecules can vary significantly depending upon their antigen specificity. Certain portions of a V region are more conserved than others and are referred to as framework regions (FW regions). In contrast, certain portions of a V region are highly variable and are designated hypervariable regions. When the $V_L$ and $V_H$ domains pair in an immunoglobulin molecule, the hypervariable regions from each domain associate and create hypervariable loops that form the antigen binding sites. Thus, the hypervariable loops determine the specificity of an immunoglobulin and are termed complementarity-determining regions (CDRs) because their surfaces are complementary to antigens.

Further variability of V regions is conferred by combinatorial variability of gene segments that encode an immunoglobulin V region. Immunoglobulin genes comprise multiple germline gene segments which somatically rearrange to form a rearranged immunoglobulin gene that encodes an immunoglobulin molecule. $V_L$ regions are encoded by a L chain V gene segment and J gene segment (joining segment). $V_H$ regions are encoded by a H chain V gene segment, D gene segment (diversity segment) and J gene segment (joining segment).

Both a L chain and H chain V gene segment contain three regions of substantial amino acid sequence variability. Such regions are referred to as L chain CDR1, CDR2 and CDR3, and H chain CDR1, CDR2 and CDR3, respectively. The length of an L chain CDR1 can vary substantially between different $V_L$ regions. For example, the length of CDR1 can vary from about 7 amino acids to about 17 amino acids. In contrast, the lengths of L chain CDR2 and CDR3 typically do not vary between different $V_L$ regions. The length of a H chain CDR3 can vary substantially between different $V_H$ regions. For example, the length of CDR3 can vary from about 1 amino acid to about 20 amino acids. Each H and L chain CDR region is flanked by FW regions.

Other functional aspects of an immunoglobulin molecule include the valency of an immunoglobulin molecule, the affinity of an immunoglobulin molecule, and the avidity of an immunoglobulin molecule. As used herein, affinity refers to the strength with which an immunoglobulin molecule binds to an antigen at a single site on an immunoglobulin molecule (i.e., a monovalent Fab fragment binding to a monovalent antigen). Affinity differs from avidity which refers to the sum total of the strength with which an immunoglobulin binds to an antigen. Immunoglobulin binding affinity can be measured using techniques standard in the art, such as competitive binding techniques, equilibrium dialysis or BIAcore methods. As used herein, valency refers to the number of different antigen binding sites per immunoglobulin molecule (i.e., the number of antigen binding sites per antibody molecule of antigen binding fragment). For example, a monovalent immunoglobulin molecule can only bind to one antigen at one time, whereas a bivalent immunoglobulin molecule can bind to two or more antigens at one time, and so forth. Both monovalent and bivalent antibodies that selectively bind to PS receptors of the present invention are encompassed herein.

In one embodiment of the present invention, a monovalent antibody can be used as a regulatory compound (discussed below). Such an antibody is not capable of aggregating receptors. Divalent antibodies can also be used in the present invention.

In one embodiment, the antibody is a bi- or multi-specific antibody. A bi-specific (or multi-specific) antibody is capable of binding two (or more) antigens, as with a divalent (or multivalent) antibody, but in this case, the antigens are different antigens (i.e., the antibody exhibits dual or greater specificity). A bi-specific antibody suitable for use in the present method includes an antibody having: (a) a first portion (e.g., a first antigen binding portion) which binds to the PS receptor; and (b) a second portion which binds to a cell surface molecule expressed by a cell which expresses a PS receptor. In this embodiment, the second portion can bind to any cell surface molecule. In a preferred embodiment, the second portion is capable of targeting the regulatory antibody to a specific target cell (i.e., the regulatory antibody binds to a target molecule). For example, the second portion of the bi-specific antibody can be an antibody that binds to another cell surface molecule on a target cell, such as a macrophage, a fibroblast, or an epithelial cell.

Isolated antibodies of the present invention can include serum containing such antibodies, or antibodies that have been purified to varying degrees. Whole antibodies of the present invention can be polyclonal or monoclonal. Alternatively, functional equivalents of whole antibodies, such as antigen binding fragments in which one or more antibody domains are truncated or absent (e.g., Fv, Fab, Fab', or F(ab)$_2$ fragments), as well as genetically-engineered antibodies or antigen binding fragments thereof, including single chain antibodies or antibodies that can bind to more than one epitope (e.g., bi-specific antibodies), or antibodies that can bind to one or more different antigens (e.g., bi- or multi-specific antibodies), may also be employed in the invention.

Genetically engineered antibodies of the invention include those produced by standard recombinant DNA techniques involving the manipulation and re-expression of DNA encoding antibody variable and/or constant regions. Particular examples include, chimeric antibodies, where the $V_h$ and/or $V_L$ domains of the antibody come from a different source to the remainder of the antibody, and CDR grafted antibodies (and antigen binding fragments thereof), in which at least one CDR sequence and optionally at least one variable region framework amino acid is (are) derived from one source and the remaining portions of the variable and the constant regions (as appropriate) are derived from a different source. Construction of chimeric and CDR-grafted antibodies are described, for example, in European Patent Applications: EP-A 0194276, EP-A 0239400, EP-A 0451216 and EP-A 0460617.

Generally, in the production of an antibody, a suitable experimental animal, such as, for example, but not limited to, a rabbit, a sheep, a hamster, a guinea pig, a mouse, a rat, or a chicken, is exposed to an antigen against which an antibody is desired. Typically, an animal is immunized with an effective amount of antigen that is injected into the animal. An effective amount of antigen refers to an amount needed to induce antibody production by the animal. The animal's immune system is then allowed to respond over a pre-determined period of time. The immunization process can be repeated until the immune system is found to be producing antibodies to the antigen. In order to obtain polyclonal antibodies specific for the antigen, serum is collected from the animal that contains the desired antibodies (or in the case of a chicken, antibody can be collected from the eggs). Such serum is useful as a reagent. Polyclonal antibodies can be further purified from the serum (or eggs) by, for example, treating the serum with ammonium sulfate.

Monoclonal antibodies may be produced according to the methodology of Kohler and Milstein (*Nature* 256:495–497, 1975). For example, B lymphocytes are recovered from the spleen (or any suitable tissue) of an immunized animal and then fused with myeloma cells to obtain a population of hybridoma cells capable of continual growth in suitable culture medium. Hybridomas producing the desired antibody are selected by testing the ability of the antibody produced by the hybridoma to bind to the desired antigen.

A preferred method to produce antibodies of the present invention includes (a) administering to an animal an effective amount of a protein, peptide or mimetic thereof of the present invention to produce the antibodies and (b) recovering the antibodies. In another method, antibodies of the present invention are produced recombinantly. For example, once a cell line, for example a hybridoma, expressing an antibody according to the invention has been obtained, it is possible to clone therefrom the cDNA and to identify the variable region genes encoding the desired antibody, including the sequences encoding the CDRs. From here, antibodies and antigen binding fragments according to the invention may be obtained by preparing one or more replicable expression vectors containing at least the DNA sequence encoding the variable domain of the antibody heavy or light chain and optionally other DNA sequences encoding remaining portions of the heavy and/or light chains as desired, and transforming/transfecting an appropriate host cell, in which production of the antibody will occur. Suitable expression hosts include bacteria, (for example, an *E. coli* strain), fungi, (in particular yeasts, e.g. members of the genera Pichia, Saccharomyces, or Kluyveromyces,) and mammalian cell lines, e.g. a non-producing myeloma cell line, such as a mouse NSO line, or CHO cells. In order to obtain efficient transcription and translation, the DNA sequence in each vector should include appropriate regulatory sequences, particularly a promoter and leader sequence operably linked to the variable domain sequence. Particular methods for producing antibodies in this way are generally well known and routinely used. For example, basic molecular biology procedures are described by Maniatis et al. (Molecular Cloning, Cold Spring Harbor Laboratory, New York, 1989); DNA sequencing can be performed as described in Sanger et al. (PNAS 74, 5463, (1977)) and the Amersham International plc sequencing handbook; and site directed mutagenesis can be carried out according to the method of Kramer et al. (*Nucl. Acids Res.* 12, 9441, (1984)) and the Anglian Biotechnology Ltd. handbook. Additionally, there are numerous publications, including patent specifications, detailing techniques suitable for the preparation of antibodies by manipulation of DNA, creation of expression vectors and transformation of appropriate cells, for example as reviewed by Mountain A and Adair, J R in Biotechnology and Genetic Engineering Reviews (ed. Tombs, M P, 10, Chapter 1, 1992, Intercept, Andover, UK) and in the aforementioned European Patent Applications.

Alternative methods, employing, for example, phage display technology (see for example U.S. Pat. Nos. 5,969,108, 5,565,332, 5,871,907, 5,858,657) or the selected lymphocyte antibody method of U.S. Pat. No. 5,627,052 may also be used for the production of antibodies and/or antigen fragments of the invention, as will be readily apparent to the skilled individual.

Antibodies raised against defined proteins can be advantageous because such antibodies are not substantially contaminated with antibodies against other substances that might otherwise cause interference in a diagnostic assay or side effects if used in a therapeutic composition. Antibodies that selectively bind to a PS receptor of the present invention are described in Example 1.

The invention also extends to non-antibody polypeptides, sometimes referred to as binding partners, that have been designed to bind specifically to, and either activate or inhibit as appropriate, a PS receptor of the invention. Examples of the design of such polypeptides, which possess a prescribed ligand specificity are given in Beste et al. (*Proc. Natl. Acad. Sci.* 96:1898–1903, 1999), incorporated herein by reference in its entirety.

Another embodiment of the present invention relates to an agonist of a phosphatidylserine receptor of the present invention. Preferably, such an agonist is an agonist of a PS receptor consisting of an amino acid sequence selected from the group of: SEQ ID NO:3, SEQ ID NO:5, SEQ ID NO:7, SEQ ID NO:9 and SEQ ID NO:10. Such an agonist can be any compound which is capable of associating with (e.g., binding to) such a receptor in a manner that the biological activity of the receptor is stimulated or increased. The phrase "PS receptor agonist compound" or "PS receptor agonist" refers to any compound, including, but not limited to, an antibody that selectively binds to and activates or increases the activation of a phosphatidylserine receptor, phosphatidylserine, phosphatidylserine homologues, and any suitable product of drug design (e.g., a mimetic of phosphatidylserine) which is characterized by its ability to agonize (e.g., stimulate, induce, increase, enhance) the biological activity of a naturally occurring PS receptor as described herein (e.g., by interaction/binding with and/or activation of a PS receptor). Examples of agonist antibodies are described herein and include monoclonal antibodies, mAb 217 and mAb 284 (See Example 1). Agonists of phosphatidylserine receptors of the present invention are particularly useful in methods for regulating inflammation, and particularly, in methods for reducing inflammation and treating diseases or conditions in which it is desirable to reduce inflammation (e.g., transplant rejection, autoimmune disease), and particularly, to reduce the production of proinflammatory cytokines. Contact of a PS receptor with an agonist typically produces at least one result, as compared to in the absence of the agonist which includes, but is not limited to: (1) binding of the agonist to the PS receptor; (2) increased ability (or the induction of the ability) of a cell expressing a PS receptor to recognize apoptotic cells in a phosphatidylserine-specific manner; (3) increased ability (or induction of the ability) of a cell expressing a PS receptor to engulf apoptotic cells in a phosphatidylserine-specific manner; (4) increased production of anti-inflammatory mediators by a cell expressing the PS receptor (e.g., TGFβ, PGE2); (5) decreased production of proinflammatory mediators by a cell expressing the PS receptor (e.g., TNFα, chemokines, GM-CSF, IL-1); and, (6) increased ability (or induction of the ability) of a cell expressing the PS receptor to bind to and/or engulf phosphatidylserine-expressing particles which include, but are not limited to, lipid-symmetric red blood cells, PS-containing liposomes, parasites, viruses and other microbes that express phosphatidylserine or homologues thereof.

Yet another embodiment of the present invention relates to an antagonist of a phosphatidylserine receptor of the present invention. Preferably, such an antagonist is an antagonist of a PS receptor consisting of an amino acid sequence selected from the group of: SEQ ID NO:3, SEQ ID NO:5, SEQ ID NO:7, SEQ ID NO:9 and SEQ ID NO:10. The phrase "PS receptor antagonist compound" or "PS receptor antagonist" refers to any compound which is capable of associating with a PS receptor in a manner that the biological activity of the receptor is decreased (e.g., reduced, inhibited, blocked). Such a compound can include, but is not limited to, an antibody that selectively binds to and blocks access to the receptor by a natural ligand, or reduces or inhibits the activity of a PS receptor, a product of drug design that blocks the receptor or reduces the biological activity of the receptor, an anti-sense nucleic acid molecule that binds to a nucleic acid molecule encoding the receptor and prevents expression of the receptor, a ribozyme that binds to PS receptor RNA and prevents expression of the receptor, and a soluble phosphatidylserine receptor as described herein, which competes with a natural receptor for ligands of the receptor. Antagonists of phosphatidylserine receptors of the present invention are particularly useful in methods to treat (i.e., reduce, ameliorate symptoms associated with) cancer, and infectious diseases, whereby the pathogenic microorganism gains entrance to a host cell via PS receptors. Contact of a PS receptor, or a PS receptor ligand, with a PS receptor antagonist typically produces at least one result, as compared to in the absence of the antagonist, which includes, but is not limited to: (1) inhibited or decreased binding of the natural PS receptor ligand to the PS receptor; (2) decreased ability (or the induction of the ability) of a cell expressing a PS receptor to recognize apoptotic cells in a phosphatidylserine-specific manner; (3) decreased ability (or induction of the ability) of a cell expressing a PS receptor to engulf apoptotic cells in a phosphatidylserine-specific manner; (4) decreased production of anti-inflammatory mediators by a cell expressing the PS receptor (e.g., TGFβ, PGE2); (5) increased production of proinflammatory mediators by a cell expressing the PS receptor (e.g., TNFα, chemokines, GM-CSF, IL-1); and, (6) decreased ability (or induction of the ability) of a cell expressing the PS receptor to bind to and/or engulf phosphatidylserine-expressing particles which include, but are not limited to, lipid-symmetric red blood cells, PS-containing liposomes, parasites, viruses and other microbes that express phosphatidylserine or homologues thereof.

Agonists and antagonists that are products of drug design can be produced using various methods known in the art. Various methods of drug design, useful to design mimetics or other therapeutic compounds useful in the present invention are disclosed in Maulik et al., 1997, *Molecular Biotechnology: Therapeutic Applications and Strategies,* Wiley-Liss, Inc., which is incorporated herein by reference in its entirety. A PS receptor agonist or antagonist can be obtained, for example, from molecular diversity strategies (a combination of related strategies allowing the rapid construction of large, chemically diverse molecule libraries), libraries of natural or synthetic compounds, in particular from chemical or combinatorial libraries (i.e., libraries of compounds that differ in sequence or size but that have the similar building blocks) or by rational, directed or random drug design. See for example, Maulik et al., supra.

In a molecular diversity strategy, large compound libraries are synthesized, for example, from peptides, oligonucleotides, carbohydrates and/or synthetic organic molecules, using biological, enzymatic and/or chemical approaches. The critical parameters in developing a molecular diversity strategy include subunit diversity, molecular size, and library diversity. The general goal of screening such libraries is to utilize sequential application of combinatorial selection to obtain high-affinity ligands for a desired target, and then to optimize the lead molecules by either random or directed design strategies. Methods of molecular diversity are described in detail in Maulik, et al., ibid.

Maulik et al. also disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional receptor structures and small fragment probes, followed by linking together of favorable probe sites.

According to the present invention, a ribozyme typically contains stretches of complementary RNA bases that can base-pair with a target RNA ligand, including the RNA molecule itself, giving rise to an active site of defined structure that can cleave the bound RNA molecule (See Maulik et al., 1997, supra). Therefore, a ribozyme can serve as a targeting delivery vehicle for a nucleic acid molecule, or alternatively, the ribozyme can target and bind to RNA encoding a PS receptor, for example, and thereby effectively inhibit the translation of the PS receptor.

As used herein, an anti-sense nucleic acid molecule is defined as an isolated nucleic acid molecule that reduces expression of a PS receptor by hybridizing under high stringency conditions to a gene encoding the PS receptor. Such a nucleic acid molecule is sufficiently similar to the nucleic acid sequence encoding the PS receptor that the molecule is capable of hybridizing under high stringency conditions to the coding strand of the gene or RNA encoding the natural PS receptor. A PS receptor gene includes all nucleic acid sequences related to a PS receptor gene such as regulatory regions that control production of the protein encoded by that gene (such as, but not limited to, transcription, translation or post-translation control regions) as well as the coding region itself. Preferably, an anti-sense nucleic acid molecule of the present invention (also referred to as a PS receptor anti-sense molecule) hybridizes under high or very high stringency conditions to a nucleic acid sequence of SEQ ID NO:1, SEQ ID NO:2, SEQ ID NO:4, SEQ ID NO:6 and/or SEQ ID NO:8, or to a fragment of such nucleic acid sequences, such fragment being selected from: (a) nucleotides from between 756 and 867 to 1242 of SEQ ID NO:2; (b) nucleotides from between 756 and 867 to 1209 of SEQ ID NO:4; (c) nucleotides from between 618 and 729 to 1047 of SEQ ID NO:6; and/or (d) nucleotides from between 771 and 882 to 1224 of SEQ ID NO:8. In a particularly preferred embodiment, a PS receptor anti-sense molecule of the present invention is 100% identical to the complement of a nucleic acid sequence represented by SEQ ID NO:1, SEQ ID NO:2, SEQ ID NO:4, SEQ ID NO:6 and/or SEQ ID NO:8, or any of the above-identified fragments. Preferably, an anti-sense molecule of the present invention is at least about 25 nucleotides in length, and more preferably at least about 50 nucleotides in length, and more preferably at least about 75 nucleotides in length, and more preferably at least about 100 nucleotides in length, and more preferably at least about 200 nucleotides in length, and more preferably at least about 300 nucleotides in length, and more preferably at least about 400 nucleotides in length, and more preferably at least about 500 nucleotides in length, and more preferably at least about 600 nucleotides in length, and more preferably at least about 700 nucleotides in length, and more preferably at least about 800 nucleotides in length, and more preferably at least about 900 nucleotides in length. In another embodiment, an anti-sense nucleic acid molecule of the present invention is preferably at least about 948 nucleotides in length, and more preferably at least about 975, and more preferably at least about 1000, and more preferably at least about 1025, and more preferably at least about 1050, and more preferably at least about 1075, and more preferably at least about 1100, and more preferably at least about 1125, and more preferably at least about 1150, and more preferably at least about 1175, and more preferably at least about 1200, and more preferably at least about 1225, and more preferably at least about 1250, nucleotides in length. In a particularly preferred embodiment, an anti-sense nucleic acid molecule of the present invention is the exact complement of the coding region of a PS receptor nucleic acid molecule of the present invention (i.e., the exact complement of SEQ ID NO:2, SEQ ID NO:4, SEQ ID NO:6, SEQ ID NO:8). It is noted that the anti-sense of the coding region does not necessarily include the anti-sense of the stop codon.

One embodiment of the present invention relates to a method to identify a regulatory compound of a phosphatidylserine receptor. Such a method includes the steps of: (a) contacting a phosphatidylserine receptor protein, including any PS receptor protein (including homologues thereof) previously described herein, with a putative regulatory compound; (b) detecting whether the putative regulatory compound binds to the receptor; and, (c) detecting whether the putative regulatory compound increases or decreases activity of the receptor as compared to prior to contact with the compound. Compounds that bind to the receptor and increase or decrease activity of the receptor, as compared to a receptor in the absence of the compound, indicates that the putative regulatory compound is a regulator of the phosphatidylserine receptor. The step of detecting can include detecting whether the putative regulatory compound: (a) binds to the receptor; (b) activates the receptor or increases activation of the receptor when in the presence of a stimulator of the receptor; (c) inhibits activation of the receptor; (d) reduces activation of the receptor when in the presence of stimulator of the receptor; and/or (e) regulates a biological activity of a cell that expresses the receptor, such biological activity being associated with the activation of such receptor (e.g., TGFβ production, inflammatory cytokine production/inhibition, phosphorylation of the receptor, phagocytosis of apoptotic cells). Detection of any one or more of such activities as a result of contact of the receptor with the putative regulatory compound indicates that the compound is a regulator of a phosphatidylserine receptor of the present invention. Such a method can be cell based or non-cell based. In one embodiment, a phosphatidylserine receptor of the present invention or a two- or three-dimensional model thereof, is used in a large scale screening of compound libraries and/or in computer-based drug design methods. In one embodiment, the step of detecting whether the putative regulatory compound increases or decreases activation of the receptor comprises the steps of contacting the receptor with a stimulator of the receptor and detecting whether activation of the receptor is increased or decreased in the presence of the putative regulatory compound as compared to in the absence of the putative regulatory compound. In another embodiment, the method further comprises a step of detecting whether the putative regulatory compound regulates a biological activity of a cell that expresses the receptor, the biological activity being selected from the group consisting of transforming growth factor β (TGFβ) production, prostaglandin E2 (PGE2) production, tumor necrosis factor α (TNFα) production, chemokine production, granulocyte-macrophage colony stimulating factor (GM-CSF) production, interleukin-1 (IL-1) production, phosphorylation of the receptor, and phagocytosis of apoptotic cells. Upregulation (increase, stimulation, enhancement) of production of anti-inflammatory factors, including TGFβ and PGE2, and/or down regulation (decrease, inhibition, absence of) of production of proinflammatory factors, including TNFα, chemokines, GM-CSF and IL-1, by a cell expressing the PS receptor, are associated with increased PS receptor activity or the stimulation of PS receptor activity. Similarly, down regulation of production of anti-inflammatory factors and/or upregulation of production of proinflammatory factors by a cell expressing the PS receptor, are associated with decreased, or inhibited, PS receptor activity.

As used herein, the term "putative" refers to compounds having an unknown regulatory activity, at least with respect to the ability of such compounds to regulate PS receptors as described herein. In the method of identifying a regulatory compound according to the present invention, the method can be a cell-based assay, or non-cell-based assay. In one embodiment, the receptor is expressed by a cell (i.e., a cell-based assay). In another embodiment the receptor is in a cell lysate, or is purified or produced free of cells (e.g., a soluble receptor). In accordance with the present invention, a cell-based assay is conducted under conditions which are effective to screen for regulatory compounds useful in the method of the present invention. Effective conditions include, but are not limited to, appropriate media, temperature, pH and oxygen conditions that permit cell growth. An appropriate, or effective, medium refers to any medium in which a cell of the present invention, when cultured, is capable of cell growth and expression of a PS receptor. Such a medium is typically a solid or liquid medium comprising growth factors and assimilable carbon, nitrogen and phosphate sources, as well as appropriate salts, minerals, metals and other nutrients, such as vitamins. Culturing is carried out at a temperature, pH and oxygen content appropriate for the cell. Such culturing conditions are within the expertise of one of ordinary skill in the art.

In one embodiment, the conditions under which a receptor according to the present invention is contacted with a putative regulatory compound, such as by mixing, are conditions in which the receptor is not stimulated (activated) if essentially no regulatory compound is present. For example, such conditions include normal culture conditions in the absence of a stimulatory compound (a stimulatory compound being, e.g., the natural ligand for the receptor (phosphatidylserine), a stimulatory antibody, or other equivalent stimulus). In this embodiment, the putative regulatory compound is then contacted with the receptor. In this embodiment, the step of detecting is designed to indicate whether the putative regulatory compound binds to the PS receptor, and further, whether the putative regulatory compound stimulates the receptor.

In an alternate embodiment, the conditions under which a PS receptor according to the present invention is contacted with a putative regulatory compound, such as by mixing, are conditions in which the receptor is normally stimulated (activated) if essentially no regulatory compound is present. Such conditions can include, for example, contact of said receptor with a stimulator molecule (a stimulatory compound being, e.g., the natural ligand for the receptor (phosphatidylserine), a stimulatory antibody, or other equivalent stimulus) which binds to the receptor and causes the receptor to become activated. In this embodiment, the putative regulatory compound can be contacted with the receptor prior to the contact of the receptor with the stimulatory compound (e.g., to determine whether the putative regulatory compound blocks or otherwise inhibits the stimulation of the PS receptor by the stimulatory compound), or after contact of the receptor with the stimulatory compound (e.g., to determine whether the putative regulatory compound downregulates, or reduces the activation of the receptor).

The present methods involve contacting cells with the compound being tested for a sufficient time to allow for interaction, activation or inhibition of the receptor by the compound. The period of contact with the compound being tested can be varied depending on the result being measured, and can be determined by one of skill in the art. For example, for binding assays, a shorter time of contact with the compound being tested is typically suitable, than when activation is assessed. As used herein, the term "contact period" refers to the time period during which cells are in contact with the compound being tested. The term "incubation period" refers to the entire time during which cells are allowed to grow prior to evaluation, and can be inclusive of the contact period. Thus, the incubation period includes all of the contact period and may include a further time period during which the compound being tested is not present but during which growth is continuing (in the case of a cell based assay) prior to scoring. The incubation time for growth of cells can vary but is sufficient to allow for the binding of the PS receptor, activation of the receptor, and/or inhibition of the receptor. It will be recognized that shorter incubation times are preferable because compounds can be more rapidly screened. A preferred incubation time is between about 1 minute to about 48 hours.

The assay of the present invention can also be a non-cell based assay. In this embodiment, the putative regulatory compound can be directly contacted with an isolated receptor, or a receptor component (e.g., an isolated extracellular portion of the receptor, or soluble receptor), and the ability of the putative regulatory compound to bind to the receptor or receptor component can be evaluated, such as by an immunoassay or other binding assay. The assay can then include the step of further analyzing whether putative regulatory compounds which bind to a portion of the receptor are capable of increasing or decreasing the activity of the PS receptor. Such further steps can be performed by cell-based assay, as described above, or by non-cell-based assay. For example, isolated membranes may be used to identify compounds that interact with the PS receptor being tested. Membranes can be harvested from cells expressing PS receptors by standard techniques and used in an in vitro binding assay. $^{125}$I-labeled (other labels can be used also) ligand (e.g., $^{125}$-labeled PS) is contacted with the membranes and assayed for specific activity; specific binding is determined by comparison with binding assays performed in the presence of excess unlabeled ligand. Membranes are typically incubated with labeled ligand in the presence or absence of test compound. Compounds that bind to the receptor and compete with labeled ligand for binding to the membranes reduced the signal compared to the vehicle control samples.

Alternatively, soluble PS receptors may be recombinantly expressed and utilized in non-cell based assays to identify compounds that bind to PS receptors. Recombinantly expressed PS receptor polypeptides or fusion proteins containing one or more extracellular domains of PS receptor can be used in the non-cell based screening assays. Alternatively, peptides corresponding to the extracellular domain of the PS receptor or fusion proteins containing the extracellular domain of the PS receptor can be used in non-cell based assay systems to identify compounds that bind to the extracellular portion of the PS receptor. In non-cell based assays the recombinantly expressed PS receptor is attached to a solid substrate such as a test tube, microtiter well or a column, by means well known to those in the art. For example, a PS receptor and/or cell lysates containing such receptors can be immobilized on a substrate such as: artificial membranes, organic supports, biopolymer supports and inorganic supports. The protein can be immobilized on the solid support by a variety of methods including adsorption, cross-linking (including covalent bonding), and entrapment. Adsorption can be through van del Waal's forces, hydrogen bonding, ionic bonding, or hydrophobic binding. Exemplary solid supports for adsorption immobilization include polymeric adsorbents and ion-exchange resins. Solid supports can be in any suitable form, including in a bead form, plate form, or well form. The test compounds are then assayed for their ability to bind to the PS receptor.

In vitro cell based assays may be designed to screen for compounds that regulate PS receptor expression at either the transcriptional or translational level. In one embodiment, DNA encoding a reporter molecule can be linked to a regulatory element of the PS receptor gene and used in appropriate intact cells, cell extracts or lysates to identify compounds that modulate PS receptor gene expression. Appropriate cells or cell extracts are prepared from any cell type that normally expresses the PS receptor gene, thereby ensuring that the cell extracts contain the transcription factors required for in vitro or in vivo transcription. The screen can be used to identify compounds that modulate the expression of the reporter construct. In such screens, the level of reporter gene expression is determined in the presence of the test compound and compared to the level of expression in the absence of the test compound.

To identify compounds that regulate PS receptor translation, cells or in vitro cell lysates containing PS receptor transcripts may be tested for modulation of PS receptor mRNA translation. To assay for inhibitors of PS receptor translation, test compounds are assayed for their ability to modulate the translation of PS receptor mRNA in in vitro translation extracts.

In any embodiment of the present invention, the step of detecting includes any method that measures: (a) binding of the putative regulatory compound to the receptor (alone, or in conjunction with measuring the binding of a natural ligand of the receptor to the receptor); (b) activation of the receptor or increases activation of the receptor when in the presence of a stimulator of the receptor; (c) inhibition of activation of the receptor; (d) reduction of activation of the receptor when in the presence of stimulator of the receptor; and/or (e) regulation of a biological activity of a cell that expresses the receptor, such biological activity being associated with the activation of such receptor (e.g., TGFβ production, inflammatory cytokine production/inhibition, phosphorylation of the receptor, phagocytosis of apoptotic cells). For example, the step of detecting can include: any suitable binding assay to determine binding of the compound to the receptor; detection of phosphorylation of the receptor, wherein phosphorylation is indicative of activation of the receptor; detection of the ability of the receptor to transduce a signal as a result of stimulation of the receptor; detection of the ability to be blocked by a PS receptor-specific antibody of the present invention, such as mAb 217 and mAb 284 described in Example 1; detection of the ability of the PS receptor to bind and phagocytose apoptotic cells in a phosphatidylserine-specific manner (increased ability to bind and phagocytose apoptotic cells indicates stimulation of the receptor); detection of production of anti-inflammatory mediators by a cell expressing the PS receptor, including TGFβ and PGE2 (increased production of anti-inflammatory mediators indicates stimulation of the receptor); and, detection of production of proinflammatory mediators by a cell expressing the PS receptor, such as tumor necrosis factor α (TNFα) production, chemokine production, granulocyte-macrophage colony stimulating factor (GM-CSF) production, interleukin-1 (IL-1) production (reduced production of proinflammatory mediators indicates stimulation of the receptor). Such assays include bioassays and molecular assays, including, but not limited to, calcium mobilization assays, phosphorylation assays, kinase assays, cytokine assays, immunofluorescence microscopy, flow cytometry, immunoprecipitation assays, immunoblots, enzyme-linked immunosorbant assays, radioimmunoassays, and other binding assays, biological assays and/or combinations thereof. Several of such assays are described in the Examples section.

Agonists and antagonists of PS receptors identified by the above method or any other suitable method are useful in a variety of therapeutic methods as described herein.

Another embodiment of the present invention relates to a method to stimulate or increase the activity of a phosphatidylserine receptor. The method includes the step of contacting a phosphatidylserine receptor with an agonist of the phosphatidylserine receptor, wherein the agonist increases the activity of the phosphatidylserine receptor, and wherein the receptor comprises an amino acid sequence selected from the group consisting of: SEQ ID NO:3, SEQ ID NO:5, SEQ ID NO:7, SEQ ID NO:9 and SEQ ID NO:10. Agonists of PS receptors have been previously described herein, and include, but are not limited to: an antibody that selectively binds to and activates the phosphatidylserine receptor, phosphatidylserine, and a product of drug design that increases the activity of the receptor as compared to in the absence of the product. In a preferred embodiment, the agonist is an antibody that selectively binds to and activates the receptor.

Preferably, the biological activity of PS receptors contacted by the agonist is increased in a manner sufficient to regulate inflammation in an animal having cells which express the receptor. An agonist typically increases activity of the PS receptor by binding to the receptor and, as a result of such binding or contact, causing one or more signals to be transduced through the receptor, such that the receptor is stimulated (i.e., its activity is induced, upregulated, increased, enhanced). Therefore, one aspect of increasing (i.e., upregulating, stimulating, enhancing) the activity of the PS receptor is the binding of an agonist to the receptor. Preferably, the binding of the PS receptor by the agonist increases production of a factor selected from the group consisting of transforming growth factor β (TGFβ) and prostaglandin E2 (PGE2) by cells that express the PS receptor. In addition, or alternatively, the binding of the agonist to the PS receptor decreases production of a factor selected from the group consisting of tumor necrosis factor α (TNFα), a chemokine, granulocyte-macrophage colony stimulating factor (GM-CSF), and interleukin-1 (IL-1) by cells that express the PS receptor. Reduction of the production of proinflammatory cytokines and increase in production of anti-inflammatory mediators, such as TGFβ and PGE2 is believed to be effective to reduce inflammation in an individual that has a disease or condition in which it is desirable to reduce inflammation. In addition, contact of a PS receptor with an agonist can produce a result that includes: (1) increased ability (or the induction of the ability) of a cell expressing a PS receptor to recognize apoptotic cells in a phosphatidylserine-specific manner; (2) increased ability (or induction of the ability) of a cell expressing a PS receptor to engulf apoptotic cells in a phosphatidylserine-specific manner. Such effects can also reduce inflammatory processes, and can provide other specific therapeutic benefits to certain patients, as described in more detail below.

The step of contacting can be performed in vivo or ex vivo; administration and dosing protocols are described in detail below. Such a method is useful for down-regulating inflammation in any disease or condition in which down-regulation of inflammation is desirable, and is particularly useful for the treatment of a disease selected from the group consisting of allergic airway diseases, hyper-eosinophilic syndrome, helminthic parasitic infection, allergic rhinitis, allergic conjunctivitis, dermatitis, eczema, contact dermatitis, or food allergy, as well as infectious diseases in which it is desirable to temper, or downregulate the inflammatory response, such as viral infections. Allergic airway diseases include, but are not limited to, allergic airway diseases, which can include, but are not limited to, allergic asthma, allergic bronchopulmonary aspergillosis, eosinophilic pneumonia, allergic bronchitis bronchiectasis, occupational asthma (i.e., asthma, wheezing, chest tightness and cough caused by a sensitizing agent, such as an allergen, irritant or hapten, in the work place), reactive airway disease syndrome (i.e., a single exposure to an agent that leads to asthma), and interstitial lung disease.

In one embodiment, such a method of stimulating a PS receptor is useful in a method to promote survival of a transplanted cell or graft. Without being bound by theory, the present inventors believe that stimulation of the PS receptor on dendritic cells and macrophages, in addition to inhibiting the production of certain cytokines as discussed previously herein (and nitrous oxide, in the case of the macrophage), inhibits or prevents antigen presentation by such cells. A major problem associated with transplantation of any tissue or cell is immune-mediated graft rejection in which the recipient's T-lymphocytes recognize donorhistocompatibility antigens as "foreign". Current regimes for transplanting many tissues and organs require lifelong administration of immunosuppressive drugs. These drugs have serious side-effects and can cause increased susceptibility to infection, renal failure, hypertension, and tumor development. Administration of a PS receptor agonist to a transplant recipient is expected to reduce inflammation at the site of the graft due to general effects discussed above, and additionally, is believed to be effective to inhibit or prevent presentation of graft antigens by dendritic cells and/or macrophages to host T cells that are directed against such graft antigens.

In another embodiment, such a method of stimulating a PS receptor is useful in a method to treat an autoimmune disease. Such autoimmune diseases include, but are not limited to, rheumatoid arthritis, systemic lupus erythematosus, insulin dependent diabetes mellitus, multiple sclerosis, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomerulonephritis, or polyarteritis nodosa. Many autoimmune diseases, and particularly those mediated by T-lymphocytes (e.g., rheumatoid arthritis, insulin dependent diabetes mellitus, multiple sclerosis), are characterized by the production of proinflammatory cytokines at the site of the disease. In addition, destruction of host tissue by the host immune system increases inflammation and the infiltration of phagocytic cells into the site of the disease. In addition, due to destruction of the host tissue as a result of an autoimmune disease, some autoimmune patients require transplantation of new cells or organs. Such transplanted tissues, in addition to being subject to normal graft rejection as discussed above, are also subject to disease recurrence, wherein autoreactive T cells invade and destroy the transplant tissue in a manner similar to the original destruction of the host's tissue. Therefore, administration of a PS receptor agonist to a patient that has an autoimmune disease can reduce inflammation at the site of the disease, which can include inhibition of the presentation of autoantigens by dendritic cells at the site of inflammation, reduction in the production of proinflammatory cytokines, and increase in production of anti-inflammatory mediators.

Yet another embodiment of the present invention relates to a method to reduce the activity of a phosphatidylserine receptor. Such a method includes the step of contacting a phosphatidylserine receptor with an antagonist of the phosphatidylserine receptor, wherein the antagonist decreases the activity of the phosphatidylserine receptor, and wherein the receptor comprises an amino acid sequence selected from the group consisting of: SEQ ID NO:3, SEQ ID NO:5, SEQ ID NO:7, SEQ ID NO:9 and SEQ ID NO:10. Antagonists of PS receptors have been discussed in detail above and include, but are not limited to, an antibody that reduces the activity of the receptor, a product of drug design that reduces the biological activity of the receptor, a ribozyme that is specific for PS receptor RNA, an anti-sense nucleic acid molecule that binds to a nucleic acid molecule encoding the receptor, and a soluble phosphatidylserine receptor. In a preferred embodiment, the antagonist is an antibody that selectively binds to the receptor and reduces the activity of the receptor. In another embodiment, the antagonist is a soluble phosphatidylserine receptor as previously described herein. This embodiment of the present invention is useful for the treatment of a variety of conditions that benefit from inhibition or reduction of phagocytosis or uptake of a particular organism or cell type by a PS receptor. An antagonist typically decreases or inhibits activity of the PS receptor by binding to the receptor or by binding to a natural ligand of the receptor (e.g., a soluble PS receptor binds to the natural ligand and thereby competes with the natural PS receptor) and, as a result of such binding or contact, inhibits or prevents the transduction of signals through the receptor (or transduces a negative signal through the receptor), such that the receptor is prevented or inhibited from being stimulated, or such that the activity of the receptor is reduced or downregulated. Therefore, one aspect of decreasing (i.e., down regulating, reducing, inhibiting) the activity of the PS receptor is by the binding of an antagonist to the PS receptor or to a natural ligand of the PS receptor. The antagonist can block (completely or partially) the binding of the receptor by a natural ligand (i.e. by binding to the receptor or the ligand), can transduce a negative signal through the receptor (i.e., as a result of binding the receptor), can inhibit the expression of the receptor, or can even destroy the receptor or at least the ligand binding site on the receptor. Preferably, the contact of the antagonist with the PS receptor or a natural ligand of the receptor decreases production of a factor selected from the group consisting of transforming growth factor β (TGFβ) and prostaglandin E2 (PGE2) by cells expressing the PS receptor. In addition, or alternatively, the contact of the antagonist to the PS receptor or a natural PS receptor ligand preferably increases production of a factor selected from the group consisting of tumor necrosis factor α (TNFα), a chemokine, granulocyte-macrophage colony stimulating factor (GM-CSF), and interleukin-1 (IL-1) by cells expressing the PS receptor. Increasing the production of proinflammatory cytokines and decreasing the production of anti-inflammatory mediators, such as TGFβ and PGE2 is believed to be effective to increase inflammation at a site in an individual where it may be desirable to increase, or at least, to avoid inhibition of, inflammation (e.g., see the method to inhibit phagocytosis of apoptotic tumor cells below). In addition, contact of a PS receptor with an antagonist can produce a result that includes: (1) decreased ability of a cell expressing a PS receptor to recognize apoptotic cells in a phosphatidylserine-specific manner; (2) decreased ability of a cell expressing a PS receptor to engulf apoptotic cells in a phosphatidylserine-specific manner; and importantly for certain embodiments, (3) decreased ability of a cell expressing the PS receptor to bind to and/or engulf phosphatidylserine-expressing particles which include, but are not limited to, lipid-symmetric red blood cells, PS-containing liposomes, parasites, viruses and other microbes that express phosphatidylserine or homologues thereof. Such effects can also reduce inflammatory processes, and can provide other specific therapeutic benefits to certain patients, as described in more detail below. The step of contacting can be performed in vivo or ex vivo; administration and dosing protocols are described in detail below.

For example, one embodiment of the method to reduce PS receptor activity relates to a method to reduce the association of an apoptotic tumor cell with a phosphatidylserine receptor expressed on the surface of bystander tumor cells, macrophages or dendritic cells. This method includes the step of contacting tumor cells of a patient with an antagonist of a phosphatidylserine receptor, wherein the antagonist decreases the activity of the phosphatidylserine receptor, and wherein the phosphatidylserine receptor comprises an amino acid sequence selected from the group consisting of: SEQ ID NO:3, SEQ ID NO:5, SEQ ID NO:7, SEQ ID NO:9 and SEQ ID NO:10. Without being bound by theory, the present inventors believe that tumor cells which express the PS receptor take up apoptotic tumor cells in an effort to reduce or prevent an inflammatory response at the site of the tumor, thereby avoiding or reducing an anti-tumor immune response. By contacting the receptors on live tumor cells (i.e., tumor cells which are not undergoing apoptosis) with a PS receptor antagonist, this process can be inhibited, thereby allowing an anti-tumor immune response to progress. In addition, contacting macrophages and dendritic cells at the site of the tumor with the PS receptor antagonist may slow the process of removal of the tumor antigens. As discussed above, the present inventors believe that stimulating the PS receptor on dendritic cells and macrophages inhibits the ability of such cells to present antigens; therefore, contacting such cells with a PS receptor antagonist would allow such cells to more readily present tumor antigens at the tumor site (see discussion of antigen presentation by dendritic cells and macrophages above), thereby allowing a more potent anti-tumor immune response to progress.

Yet another embodiment of the present invention relates to a method to reduce the infection of a host cell by a parasite, comprising contacting the host cell with an antagonist of a phosphatidylserine receptor, wherein the antagonist decreases the activity of the phosphatidylserine receptor, and wherein the receptor comprises an amino acid sequence selected from the group consisting of: SEQ ID NO:3, SEQ ID NO:5, SEQ ID NO:7, SEQ ID NO:9 and SEQ ID NO:10. Some parasites use the phosphatidylserine receptor of the present invention to gain access to (i.e., infect) host cells. Preferably, the antagonist is targeted to cells which express the PS receptor and which are typically infected by such parasites. By inhibiting the ability of a parasite to gain access to a host cell, the parasite is inhibited from "hiding" from immune surveillance. Parasites that can be inhibited by this method of the present invention include, but are not limited to, Trypanosomes and Leishmania.

Yet another embodiment of the present invention relates to a method to reduce viral infection of host cells, comprising contacting the host cell with an antagonist of a phosphatidylserine receptor, wherein the antagonist decreases the activity of the phosphatidylserine receptor, and wherein the receptor comprises an amino acid sequence selected from the group consisting of: SEQ ID NO:3, SEQ ID NO:5, SEQ ID NO:7, SEQ ID NO:9 and SEQ ID NO:10. Alternatively, the method comprises contacting the virus with a compound that binds to the phosphatidylserine on the virus and inhibits the virus from binding to the phosphatidylserine receptor of the present invention. Such a method is effective to treat a viral disease and particularly, to inhibit viral infections, whereby the virus expresses a phosphatidylserine on its outer membrane, thereby enabling the virus to enter cells by binding to a phosphatidylserine receptor of the present invention. Such viruses include any virus that expresses phosphatidylserine on its outer coat and particularly includes, but is not limited to, members of the Herpes virus family, such as cytomegalovirus.

In order to perform the above-described methods of increasing or decreasing phosphatidylserine receptor activity, a PS receptor agonist or antagonist compound is typically formulated into a therapeutic composition. A composition, and particularly a therapeutic composition, of the present invention generally includes a carrier, and preferably, a pharmaceutically acceptable carrier. According to the present invention, a "pharmaceutically acceptable carrier" includes pharmaceutically acceptable excipients and/or pharmaceutically acceptable delivery vehicles, which are suitable for use in administration of the composition to a suitable in vitro, ex vivo or in vivo site. A suitable in vitro, in vivo or ex vivo site is preferably a cell that expresses a phosphatidylserine receptor of the present invention, including, but not limited to, a macrophage, a fibroblast, an epithelial cell, a dendritic cell, an endothelial cell, and a tumor cell. In some embodiments, a suitable site for delivery is a site of inflammation, a site of a tumor, a site of a transplanted graft, or a site of infection by a pathogenic microorganism. Preferred pharmaceutically acceptable carriers are capable of maintaining a protein, compound, or nucleic acid molecule according to the present invention in a form that, upon arrival of the protein, compound, or nucleic acid molecule at the cell target in a culture or in patient, the protein, compound or nucleic acid molecule is capable of interacting with its target (e.g., a naturally occurring PS receptor or a ligand of a naturally occurring PS receptor, including membrane and/or soluble PS receptors).

Suitable excipients of the present invention include excipients or formularies that transport or help transport, but do not specifically target a composition to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m or o cresol, formalin and benzol alcohol. Compositions of the present invention can be sterilized by conventional methods and/or lyophilized.

One type of pharmaceutically acceptable carrier includes a controlled release formulation that is capable of slowly releasing a composition of the present invention into a patient or culture. As used herein, a controlled release formulation comprises a compound of the present invention (e.g., a protein (including homologues), a drug, an antibody, a nucleic acid molecule, or a mimetic) in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other carriers of the present invention include liquids that, upon administration to a patient, form a solid or a gel in situ. Preferred carriers are also biodegradable (i.e., bioerodible). When the compound is a recombinant nucleic acid molecule, suitable delivery vehicles include, but are not limited to liposomes, viral vectors or other delivery vehicles, including ribozymes. Natural lipid-containing delivery vehicles include cells and cellular membranes. Artificial lipid-containing delivery vehicles include liposomes and micelles. A delivery vehicle of the present invention can be modified to target to a particular site in a patient, thereby targeting and making use of a compound of the present invention at that site. Suitable modifications include manipulating the chemical formula of the lipid portion of the delivery vehicle and/or introducing into the vehicle a targeting agent capable of specifically targeting a delivery vehicle to a preferred site, for example, a preferred cell type. Other suitable delivery vehicles include gold particles, poly-L-lysine/DNA-molecular conjugates, and artificial chromosomes.

A pharmaceutically acceptable carrier which is capable of targeting is herein referred to as a "delivery vehicle." Delivery vehicles of the present invention are capable of delivering a composition of the present invention to a target site in a patient. A "target site" refers to a site in a patient to which one desires to deliver a composition. For example, a target site can be any cell which is targeted by direct injection or delivery using liposomes, viral vectors or other delivery vehicles, including ribozymes and antibodies. Examples of delivery vehicles include, but are not limited to, artificial and natural lipid-containing delivery vehicles, viral vectors, and ribozymes. Natural lipid-containing delivery vehicles include cells and cellular membranes. Artificial lipid-containing delivery vehicles include liposomes and micelles. A delivery vehicle of the present invention can be modified to target to a particular site in a subject, thereby targeting and making use of a compound of the present invention at that site. Suitable modifications include manipulating the chemical formula of the lipid portion of the delivery vehicle and/or introducing into the vehicle a compound capable of specifically targeting a delivery vehicle to a preferred site, for example, a preferred cell type. Specifically, targeting refers to causing a delivery vehicle to bind to a particular cell by the interaction of the compound in the vehicle to a molecule on the surface of the cell. Suitable targeting compounds include ligands capable of selectively (i.e., specifically) binding another molecule at a particular site. Examples of such ligands include antibodies, antigens, receptors and receptor ligands. Manipulating the chemical formula of the lipid portion of the delivery vehicle can modulate the extracellular or intracellular targeting of the delivery vehicle. For example, a chemical can be added to the lipid formula of a liposome that alters the charge of the lipid bilayer of the liposome so that the liposome fuses with particular cells having particular charge characteristics.

One preferred delivery vehicle of the present invention is a liposome. A liposome is capable of remaining stable in an animal for a sufficient amount of time to deliver a nucleic acid molecule (e.g., an anti-sense nucleic acid molecule that hybridizes to a nucleic acid sequence encoding a PS receptor) to a preferred site in the animal. A liposome, according to the present invention, comprises a lipid composition that is capable of delivering a nucleic acid molecule described in the present invention to a particular, or selected, site in a patient. A liposome according to the present invention comprises a lipid composition that is capable of fusing with the plasma membrane of the targeted cell to deliver a nucleic acid molecule into a cell. Suitable liposomes for use with the present invention include any liposome. Preferred liposomes of the present invention include those liposomes commonly used in, for example, gene delivery methods known to those of skill in the art. More preferred liposomes comprise liposomes having a polycationic lipid composition and/or liposomes having a cholesterol backbone conjugated to polyethylene glycol. Complexing a liposome with a nucleic acid molecule of the present invention can be achieved using methods standard in the art.

A liposome delivery vehicle is preferably capable of remaining stable in a patient for a sufficient amount of time to deliver a nucleic acid molecule or other compound of the present invention to a preferred site in the patient (i.e., a target cell). A liposome delivery vehicle of the present invention is preferably stable in the patient into which it has been administered for at least about 30 minutes, more preferably for at least about 1 hour and even more preferably for at least about 24 hours. A preferred liposome delivery vehicle of the present invention is from about 0.01 microns to about 1 microns in size.

Another preferred delivery vehicle comprises a viral vector. A viral vector includes an isolated nucleic acid molecule useful in the present invention, in which the nucleic acid molecules are packaged in a viral coat that allows entrance of DNA into a cell. A number of viral vectors can be used, including, but not limited to, those based on alphaviruses, poxviruses, adenoviruses, herpesviruses, lentiviruses, adeno-associated viruses and retroviruses.

A composition which includes an agonist or antagonist of a PS receptor of the present invention can be delivered to a cell culture or patient by any suitable method. Selection of such a method will vary with the type of compound being administered or delivered (i.e., protein, nucleic acid, mimetic), the mode of delivery (i.e., in vitro, in vivo, ex vivo) and the goal to be achieved by administration/delivery of the compound or composition. According to the present invention, an effective administration protocol (i.e., administering a composition in an effective manner) comprises suitable dose parameters and modes of administration that result in delivery of a composition to a desired site (i.e., to a desired cell) and/or in regulation of PS receptor biological activity, including, but not limited to: (1) binding of an agonist or antagonist to a PS receptor; (2) regulation of production of transforming growth factor β (TGFβ) production and/orprostaglandin E2 (PGE2) production by a cell expressing a PS receptor; (3) regulation of production of inflammatory cytokines (e.g., tumor necrosis factor α (TNFα), chemokines, granulocyte-macrophage colony stimulating factor (GM-CSF), interleukin-1 (IL-1)) by a cell expressing a PS receptor; (4) regulation of the ability of a cell expressing a PS receptor to engulf apoptotic cells in a phosphatidylserine-specific manner; (5) regulation of the ability of a cell expressing a PS receptor to recognize apoptotic cells in a phosphatidylserine-specific manner; and, (6) regulation of the binding to and/or engulfment of phosphatidylserine-expressing particles which include, but are not limited to, lipid-symmetric red blood cells, PS-containing liposomes, parasites, viruses and other microbes that express phosphatidylserine or homologues thereof.

Administration routes include in vivo, in vitro and ex vivo routes. In vivo routes include, but are not limited to, oral, nasal, intratracheal injection, inhaled, transdermal, rectal, and parenteral routes. Preferred parenteral routes can include, but are not limited to, subcutaneous, intradermal, intravenous, intramuscular and intraperitoneal routes. In a preferred embodiment of the present invention, a composition containing a PS receptor agonist or antagonist is administered by a parenteral route. Intravenous, intraperitoneal, intradermal, subcutaneous and intramuscular administrations can be performed using methods standard in the art. Aerosol (inhalation) delivery can also be performed using methods standard in the art (see, for example, Stribling et al., Proc. Natl. Acad. Sci. USA 189:11277–11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Direct injection techniques are particularly useful for suppressing graft rejection by, for example, injecting the composition into the transplanted tissue, or for site-specific administration of a compound, such as at the site of a tumor. Preferably, a PS receptor agonist or antagonist alone, or contained within a pharmaceutically acceptable carrier, is administered by direct injection into or locally within the area of a transplanted tissue or tumor. Administration of a composition locally within the area of a transplanted tissue or tumor refers to injecting the composition centimeters and preferably, millimeters within the transplanted tissue or tumor. Such routes can include the use of pharmaceutically acceptable carriers as described above. Ex vivo refers to performing part of the regulatory step outside of the patient, such as by transfecting a population of cells removed from a patient with a recombinant molecule comprising a nucleic acid sequence encoding a protein according to the present invention under conditions such that the recombinant molecule is subsequently expressed by the transfected cell, and returning the transfected cells to the patient. In vitro and ex vivo routes of administration of a composition to a culture of host cells can be accomplished by a method including, but not limited to, transfection, transformation, electroporation, microinjection, lipofection, adsorption, protoplast fusion, use of protein carrying agents, use of ion carrying agents, use of detergents for cell permeabilization, and simply mixing (e.g., combining) a compound in culture with a target cell and/or target PS receptor.

In accordance with the present invention, a suitable single dose size of a PS receptor agonist or antagonist is a dose that is capable of regulating PS receptor biological activity, as previously described herein, when administered one or more times over a suitable time period. Doses can vary depending upon the goal of the administration or the condition or the disease being treated. Preferably, a protein or antibody of the present invention is administered in an amount that is between about 50 U/kg and about 15,000 U/kg body weight of the patient. In another embodiment, a protein or antibody is administered in an amount that is between about 0.01 $\mu$g and about 10 mg per kg body weight of the patient, and more preferably, between about 0.1 $\mu$g and about 100 $\mu$g per kg body weight of the patient. When the compound to be delivered is a nucleic acid molecule, an appropriate single dose results in at least about 1 pg of protein expressed per mg of total tissue protein per $\mu$g of nucleic acid delivered. More preferably, an appropriate single dose is a dose which results in at least about 10 pg of protein expressed per mg of total tissue protein per $\mu$g of nucleic acid delivered; and even more preferably, at least about 50 pg of protein expressed per mg of total tissue protein per $\mu$g of nucleic acid delivered; and most preferably, at least about 100 pg of protein expressed per mg of total tissue protein per $\mu$g of nucleic acid delivered. A preferred single dose of a naked nucleic acid vaccine ranges from about 1 nanogram (ng) to about 100 $\mu$g, depending on the route of administration and/or method of delivery, as can be determined by those skilled in the art. Suitable delivery methods include, for example, by injection, as drops, aerosolized and/or topically. In one embodiment, pure DNA constructs cover the surface of gold particles (1 to 3 $\mu$m in diameter) and are propelled into skin cells or muscle with a "gene gun." It will be obvious to one of skill in the art that the number of doses administered to a patient is dependent upon the goal of the administration (e.g., the extent of the disease or condition to be treated and the response of an individual patient to the treatment). Therefore, it is within the scope of the present invention that a suitable number of doses includes any number required to regulate PS receptor biological activity, or to regulate a disease or condition related thereto. Effective in vivo dose parameters can be determined using methods standard in the art. Such methods include, for example, determination of survival rates, side effects (i.e., toxicity), determination of inflammatory responses, and/or effects on conditions related to phagocytosis of apoptotic cells.

In the method of the present invention, agonists and antagonists of PS receptors, including proteins (including homologues), antibodies, nucleic acid molecules and/or mimetics, as well as compositions comprising such compounds, can be administered to any organism, and particularly, to any member of the Vertebrate class, Mammalia, including, without limitation, primates, rodents, livestock and domestic pets. Livestock include mammals to be consumed or that produce useful products (e.g., sheep for wool production). Preferred mammals to protect include humans. Typically, it is desirable to modulate (e.g., regulate (up or down)) PS receptor biological activity to obtain a therapeutic benefit in a patient. Patients who are suitable candidates for the method of the present invention which includes administering an agonist of a PS receptor, include, but are not limited to, patients that will benefit from a reduction in inflammation, including patients that have, or are at risk of developing, any disease or condition in which down-regulation of inflammation is desirable, such disease selected from the group consisting of allergic airway diseases, hyper-eosinophilic syndrome, helminthic parasitic infection, allergic rhinitis, allergic conjunctivitis, dermatitis, eczema, contact dermatitis, or food allergy, as well as infectious diseases in which it is desirable to temper, or downregulate the inflammatory response, such as viral infections. Patients whom are suitable candidates for the method of the present invention which includes administering an agonist of a PS receptor further include patients who are recipients of a transplanted cell or tissue graft, as well as patients who have, or are at risk of developing an autoimmune disease. Patients who are suitable candidates for the method of the present invention which includes administering an antagonist of a PS receptor, include patients that will benefit from prevention of the PS-specific uptake of a particular cell or organism. Such patients include, but are not limited to, patients that have a tumor, whereby reduction of the association of an apoptotic tumor cell with a phosphatidylserine receptor expressed on the surface of bystander tumor cells, macrophages or dendritic cells, reduces phagocytosis of such cells by the bystander cells, and allows the immune system of the patient to identify and respond to tumor cell antigens. Such patients also include patients who have or are at risk of being infected with a pathogenic microorganism, including certain parasites and viruses, which enter host cells via PS receptors.

According to the present invention, the method of the present invention is primarily directed to the regulation of the biological activity of PS receptor biological activity in a subject with the added, but not required, goal of providing some therapeutic benefit to a patient. Regulating PS receptor activity in a patient in the absence of obtaining some therapeutic benefit can be useful for the purposes of determining factors involved (or not involved) in a disease and preparing a patient to more beneficially receive another therapeutic composition. In a preferred embodiment, however, the methods of the present invention are directed to the modulation of PS receptor biological activity which is useful in providing some therapeutic benefit to a patient. As such, a therapeutic benefit is not necessarily a cure for a particular disease or condition, but rather, preferably encompasses a result which can include alleviation of the disease or condition, elimination of the disease or condition, reduction of a symptom associated with the disease or condition, prevention or alleviation of a secondary disease or condition resulting from the occurrence of a primary disease or condition, and/or prevention of the disease or condition. As used herein, the phrase "protected from a disease" refers to reducing the symptoms of the disease; reducing the occurrence of the disease, and/or reducing the severity of the disease. Protecting a patient can refer to the ability of a composition of the present invention, when administered to a patient, to prevent a disease from occurring and/or to cure or to alleviate disease symptoms, signs or causes. As such, to protect a patient from a disease includes both preventing disease occurrence (prophylactic treatment) and treating a patient that has a disease (therapeutic treatment) to reduce the symptoms of the disease. In particular, protecting a patient from a disease or enhancing another therapy (e.g., transplantation) is accomplished by regulating PS receptor activity such that a beneficial effect is obtained. A beneficial effect can easily be assessed by one of ordinary skill in the art and/or by a trained clinician who is treating the patient. The term, "disease" refers to any deviation from the normal health of a mammal and includes a state when disease symptoms are present, as well as conditions in which a deviation (e.g., infection, gene mutation, genetic defect, etc.) Has occurred, but symptoms are not yet manifested.

The following examples are provided for the purpose of illustration and are not intended to limit the scope of the present invention.

EXAMPLES

Example 1

The following example describes the identification, cloning and characterization of the novel phosphatidyl serine (PS) receptor of the present invention.
Results Monoclonal antibodies were generated against human macrophages (HMDM) treated with TGFβ and β-glucan to induce PS recognition (Fadok et al., *J Immunol* 161:6250–6257 (1998)). Two IgM antibodies (denoted mAb 217 and mAb 284) bound at higher levels to stimulated HMDM compared to unstimulated HMDM (data not shown). As shown in FIG. 1 for mAb 217, this binding was inhibited by preincubating the macrophages with PS liposomes at 4° C. prior to staining (FIG. 1, N=4; p=0.0008). Liposomes containing PI (FIG. 1) or pure phosphatidylcholine (data not shown) had no effect. Binding was also reduced by down regulating the antigen with PS liposomes for 30 minutes at 37° C. (not shown). Both antibodies inhibited uptake of apoptotic cells by stimulated HMDM, but not by unstimulated HMDM (data not shown). For these experiments, 48.9%+/−8.6 unstimulated macrophages contained apoptotic bodies and 55.2%+/−6.1 stimulated macrophages contained apoptotic bodies (N=5; +/−s.e.m). Although not shown, liposomes containing PI and the tetrapeptide control RGES had no effect on uptake.

Next, mAb 217 was used to examine a variety of adherent and suspension cells by flow cytometry. The ability of this antibody to bind to macrophages was not species specific. Mouse bone marrow-derived macrophages only bound to the antibody if they were stimulated to recognize PS (Fadok et al., *J Immunol* 151:4274–4285 (1993)). In contrast, thioglycollate-elicited macrophages which constitutively recognize PS (Fadok et al., *J Immunol* 148:2207–2216 (1992); Fadok et al., *J Immunol* 149:4029–4035 (1992); Pradhan et al., *Mol Biol Cell* 8:767–778 (1997)) bound to mAb 217. Also positive for expression were the mouse macrophage cell lines J774 and RAW264.7, as well as macrophages derived in vitro from embryonic stem cells. mAb 217 failed to bind to circulating human blood cells (monocytes, lymphocytes, neutrophils, red blood cells) or cell lines mimicking them, including the lymphocytic lines, Jurkat T cells and mouse M12.C3 cells, and the myelocytic lines HL-60, PLB985, THP-1 and U937. Treatment of the myelocytic, but not lymphocytic, cell lines with PMA induced expression of the antigen (data not shown). Several fibroblastic and epithelial cell lines (including NIH3T3, COS-1, COS-7, CHO-K1, HeLA, HC-11, HT1080, HEK293) as well as primary lung fibroblasts and primary mammary epithelial cells, were positive for binding to mAb 217.

Inhibition of apoptotic cell uptake by mAb 217 corresponded well with inhibition by PS liposomes. Thus, uptake by β-glucan-stimulated bone marrow macrophages, thioglycollate-elicited peritoneal macrophages, PMA-stimulated THP-1 cells, primary lung fibroblasts, 3T3 fibroblasts (data not shown), and the mammary epithelial cell line HC-11 was inhibited by PS liposomes and by mAb 217 to similar degrees (FIGS. 2A–2E). In these experiments, mouse bone marrow-derived macrophages were stimulated induce the ability to recognize PS (Fadok et al., *J Immunol* 151:4274–4285 (1993)). The mean percentages of phagocytes containing apoptotic bodies were as follows: unstimulated BMDM, 45% (FIG. 2A; stimulated BMDM, 42% (FIG. 2A); thioglycollate-elicitedmacrophages, 62% (FIG. 2B); PMA-stimulated THP-1 cells, 24% (FIG. 2C); HC-11 mouse mammary epithelial cells, 15% (FIG. 2D); and primary lung fibroblasts, 17.8% (FIG. 2E); (N=5; +/−s.e.m.).

Western blots using mAb 217 were performed on whole cell extracts from human Jurkat T lymphocytes, mouse M12.C3 B lymphocytes, human THP-1 cells differentiated into macrophages using phorbol ester, human HT1080 fibrosarcoma cells, and mouse 3T3 fibroblasts. A band of approximately 70 kD was observed in only those cell lines which showed surface expression of the antigen for mAb 217 (data not shown). The antibody was then used to determine if the receptor clustered at the sites of binding and/or engulfment of apoptotic cells. Interestingly, there was a punctuate distribution on the surface of the phagocytic fibroblast (data not shown). However, it was clear that the antibody recognized the antigen clustering around apoptotic cells.

The antigen for mAb 217 was cloned using phage display (T7-Select, Novagen, Madison, Wis.) and biopanning with mAb 217. The sequence obtained from the clones was used to search the GenBank databases. One significant match was made to a cDNA from a human brain library. It was a novel protein (KIAA 0585; GenBank Accession No. AB011157) of unknown function highly homologous to an uncharacterized ORF in *C. elegans* (Nagase et al., *DNA Res.* 5:31–39 (1998)). These authors assessed its tissue distribution by RT-PCR, and found high expression in the heart, skeletal muscle, and kidney, and moderate or low expression in brain, placenta, lung, liver, pancreas, spleen, thymus, prostate, testis, and ovary (Nagase et al., ibid.). A number of homologous sequences were present in human, mouse, Drosophila, and *C. elegans* expressed sequence tag (EST) databases. An EST clone was obtained (Accession No. R24727) through the I.M.A.G.E. consortium for further sequencing and transfection studies; sequencing suggested that it was a full-length cDNA clone.

Figure 3:
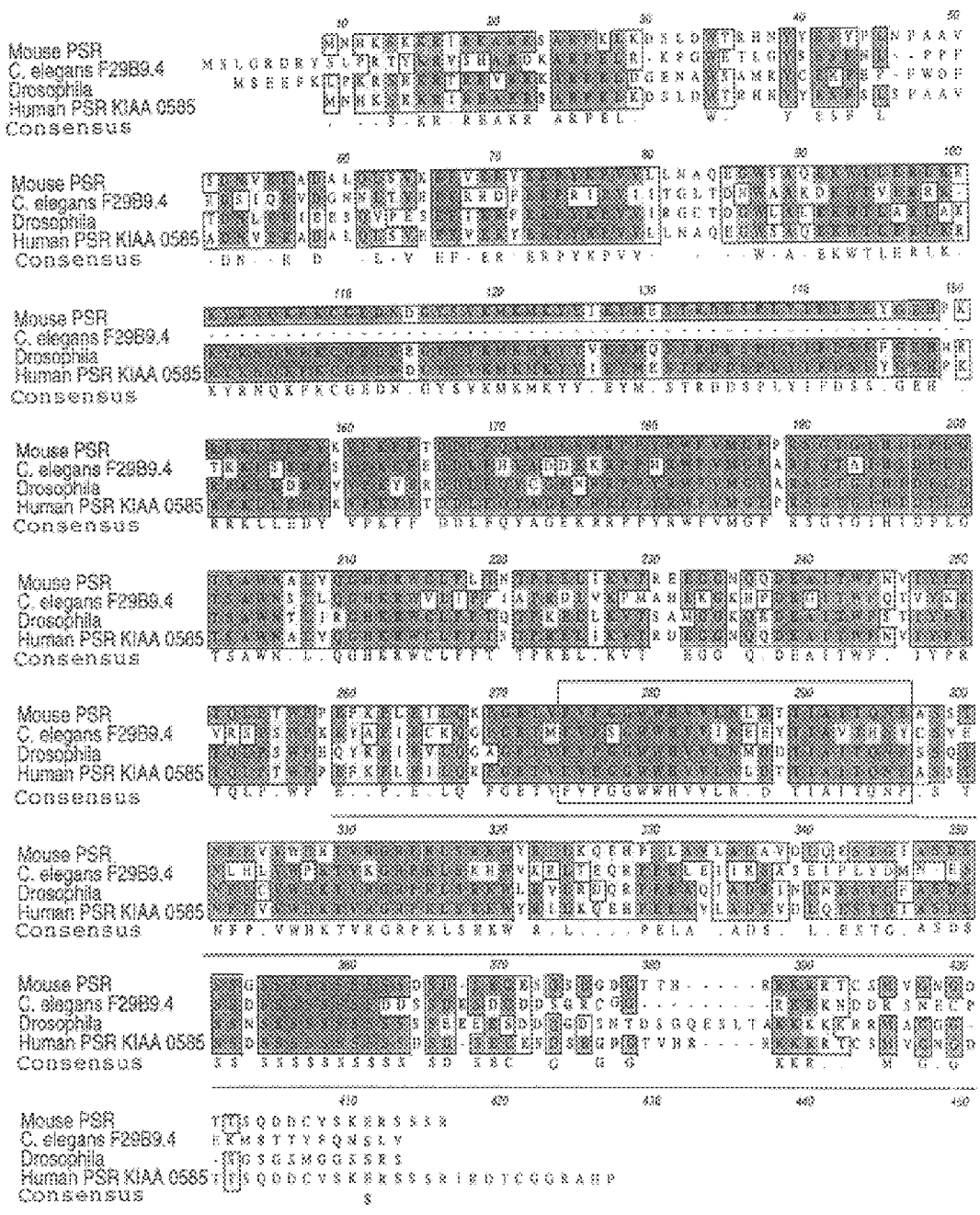
FIG. 3 is an alignment and comparison of the human (SEQ ID NO:3), mouse (SEQ ID NO:5), C. elegans (SEQ ID NO:7), and Drosophila (SEQ ID NO:9), predicted protein sequences, as well as the consensus sequence (SEQ ID NO:10) for the PS receptor of the present invention.

FIG. 3 shows a comparison of the human, mouse, Drosophila, and *C. elegans* predicted protein sequences for the candidate PS receptor. The boxed-in area of FIG. 3 represents a predicted transmembrane domain. The underlined area of FIG. 3 represents the peptide actually cloned from the phage display library. The remaining mouse sequence was deduced by aligning entries in the mouse EST databases at NCBI. Three out of four bioinformatics programs predicted a transmembrane orientation. One in particular (TopPred 2; Heijne, G. *J. Mol. Biol.* 225:487–494 (1992)) predicted a type II protein, which was consistent with the present inventors' observation that biopanning yielded clones containing sequences corresponding to the C terminus only (this antibody binds to a surface protein, as was seen by flow cytometry above). The topology programs varied slightly in their specific assignments; therefore, the area boxed in FIG. 3 (e.g., FVPGGWWHVVLNLDTTI-AITQNF of the human sequence, or positions 266 to 288 of SEQ ID NO:3; equivalent to positions 266 to 288 of SEQ ID NO:5, positions 220 to 242 of SEQ ID NO:7, positions 271 to 293 of SEQ ID NO:9 and positions 266 to 288 of SEQ ID NO:10) is a estimate based on assessment of topology and hydrophobicity. It cannot be ruled out that the protein is membrane-associated rather than membrane-spanning at this time. However, there are several basic residues in the predicted extracellular domain, including runs of lysines and arginines that could provide potential binding sites for PS, a negatively charged phospholipid. The consensus sequence for the PS binding motif (FxFxLKxxxKxR; SEQ ID NO:11) found in protein kinase C isoforms, phospholipase C, and phosphatidylserine decarboxylase is not present (Igarashi et al., *J. Biol. Chem.* 270:29075–29078 (1995)). Lastly, there is a potential tyrosine phosphorylation site (KCGEDNDGY, residues 102–110 of human KTAA 0585; positions 100 to 108 of SEQ ID NO:3) which is well within the predicted intracellular domain.

The predicted molecular weight for this protein, based on sequence analysis, was 47–48 kD for the human (SEQ ID NO:3), mouse (SEQ ID NO:5), and Drosphila (SEQ ID NO:9) gene products, and 40 kD for the nematode (SEQ ID NO:7). Because Western blotting suggested an apparent molecular weight of 70 kd, it was important to determine if deglycosylation would reduce the apparent size. Extracts from HT1080 and NIH3T3 cells were enzymatically deglycosylated, the proteins separated by PAGE, and a Western blot performed using mAb 217. Treatment with deglycosylases resulted in a shift from 70 kD to approximately 50 kD, compatible with the predicted molecular weight of 47 kD (N=3; data not shown).

Figure 4A:
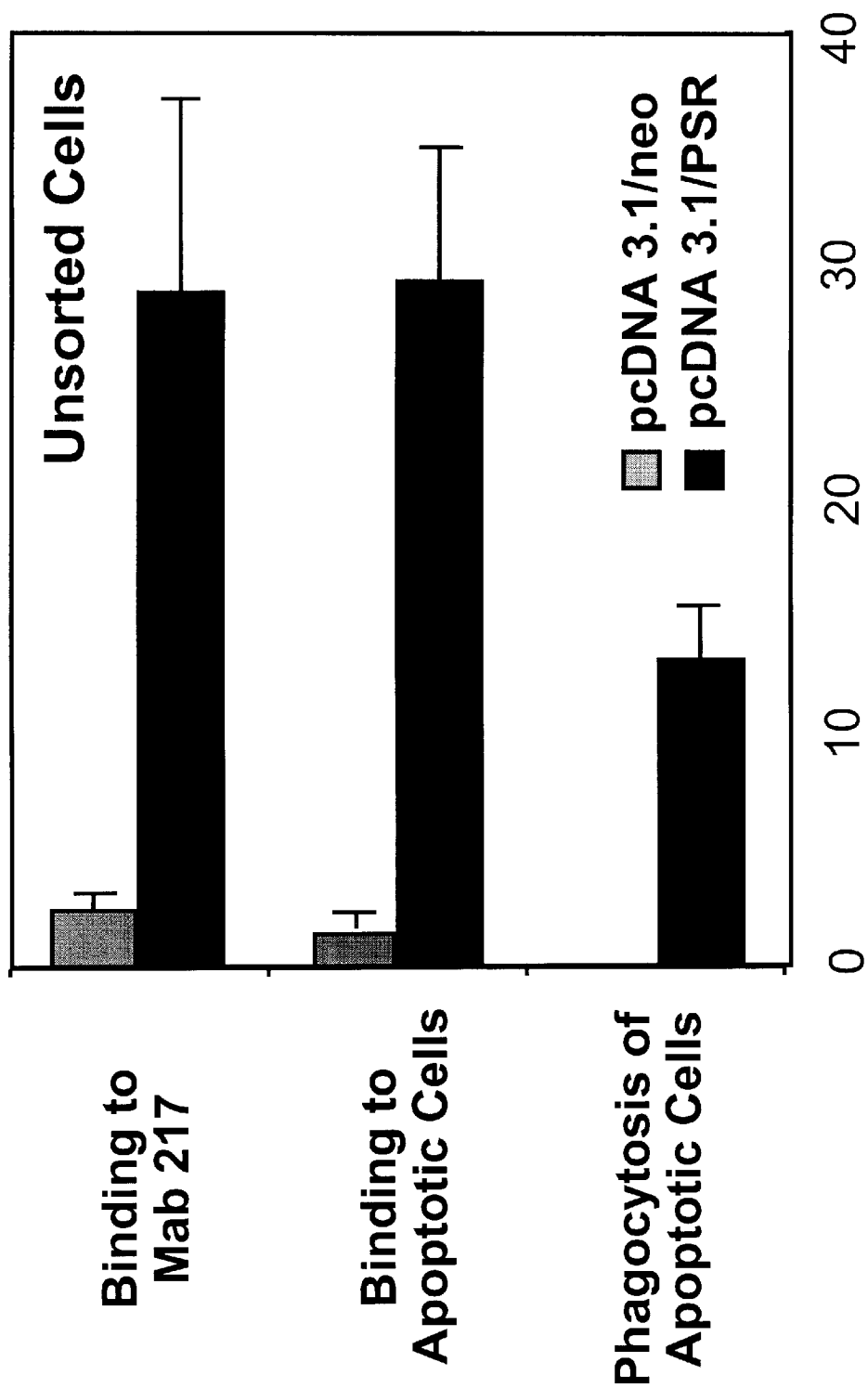
FIGS. 4A–4B are bar graphs showing that M12.C3 B cells transiently transfected with the candidate PSR phagocytose bind to and phagocytose apoptotic cells.
Figure 4B:
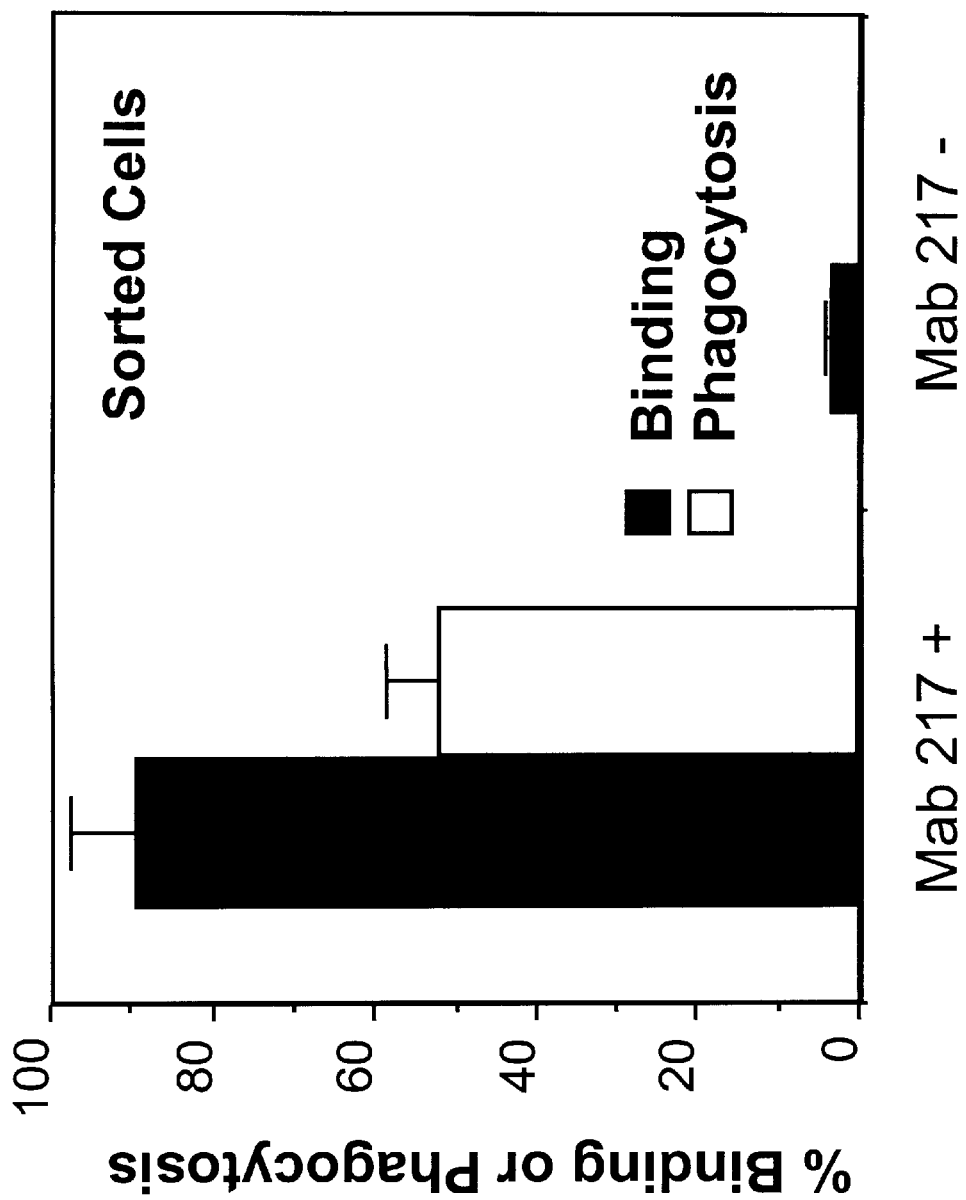

Since the adherent cell lines one would normally use for transfection (COS-7, COS-1, CHO-K1, HEK 293) already showed surface expression of the antigen for mAb 217, two unambiguously negative lymphocyte lines, the mouse Class II negative B cell line M12.C3 and the human Jurkat T cell, were selected. Neither is capable of binding or phagocytosing apoptotic cells. Using flow cytometry, it was demonstrated that transiently transfected mouse M12.C3 cells and human Jurkat T cells bound to mAb 217 (data not shown). Transiently transfected M12.C3 cells were used to examine the function of this receptor in mediating the binding and phagocytosis of apoptotic cells. Approximately 25% M12.C3 cells were able to bind mAb 217 and to apoptotic targets, and half that number were able to engulf apoptotic cells (FIG. 4A). When the transfected cells were sorted into those positive for binding to mAb 217 and those negative, it was apparent that only the positive cells were able to bind to and engulf apoptotic cells (FIG. 4B). M12.C3 cells transfected with the empty vector showed little binding to, and absolutely no phagocytosis of, apoptotic cells, in spite of expressing low levels of αvβ3, an integrin incriminated in uptake of apoptotic cells (Savill et al., *Nature* 343:170–173 (1990)). Therefore, it became important to confirm that the putative PS receptor could mediate uptake of apoptotic cells by Jurkat T cells, as they do not express any of the known surface receptors for uptake of apoptotic cells, including αvβ3. Following successful transient transfections, Jurkat T cells could bind to and engulf apoptotic cells. To overcome the problems of transient transfection, the Jurkat T cells were stably transfected by selection in G418. Four lines were obtained that consistently expressed low levels of the receptor following stimulation with 160 nM PMA (data not shown).

Figure 4C:
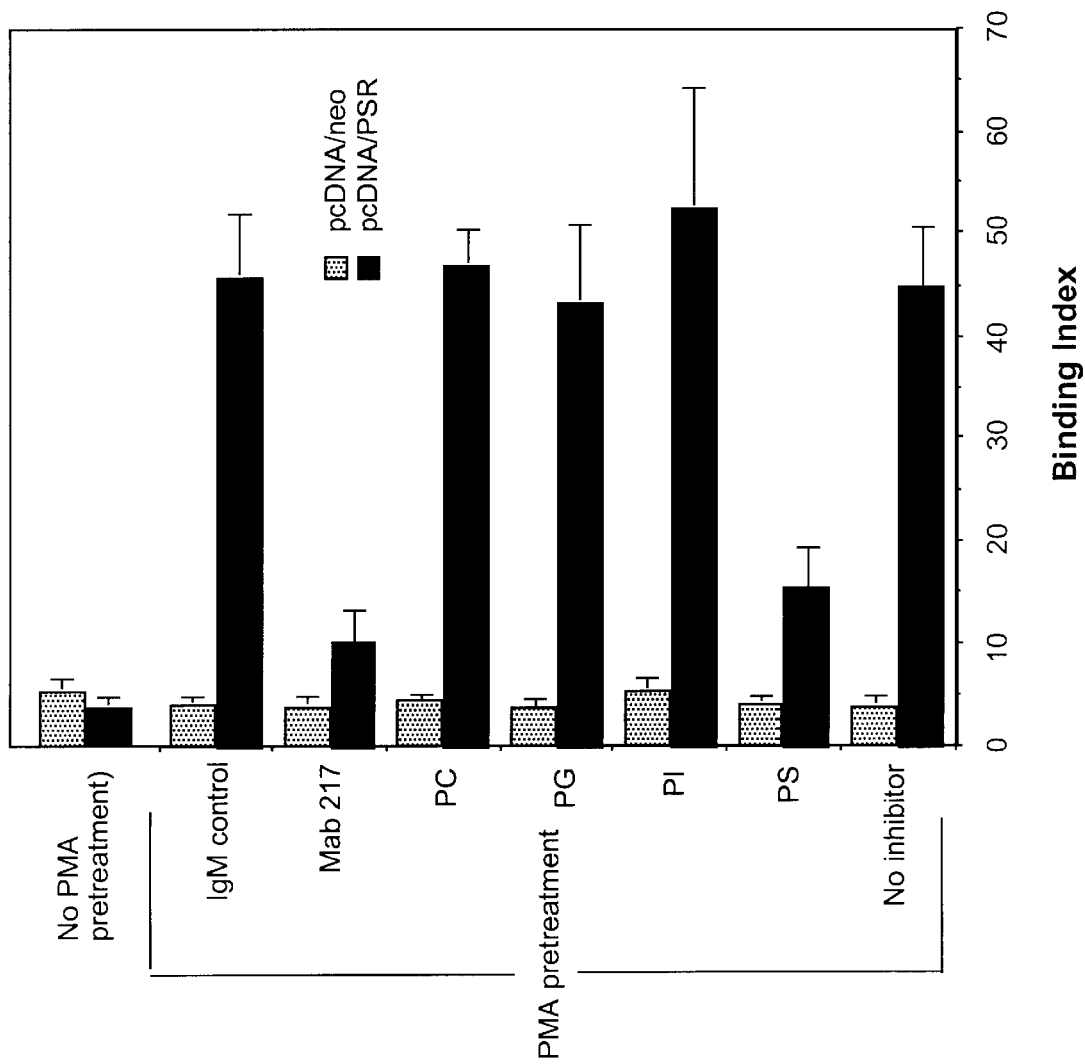
FIG. 4C is a bar graph illustrating that apoptotic cells bind to stably transfected Jurkat T cells in a PS-dependent manner, which is inhibited by mAb 217.
Figure 5:
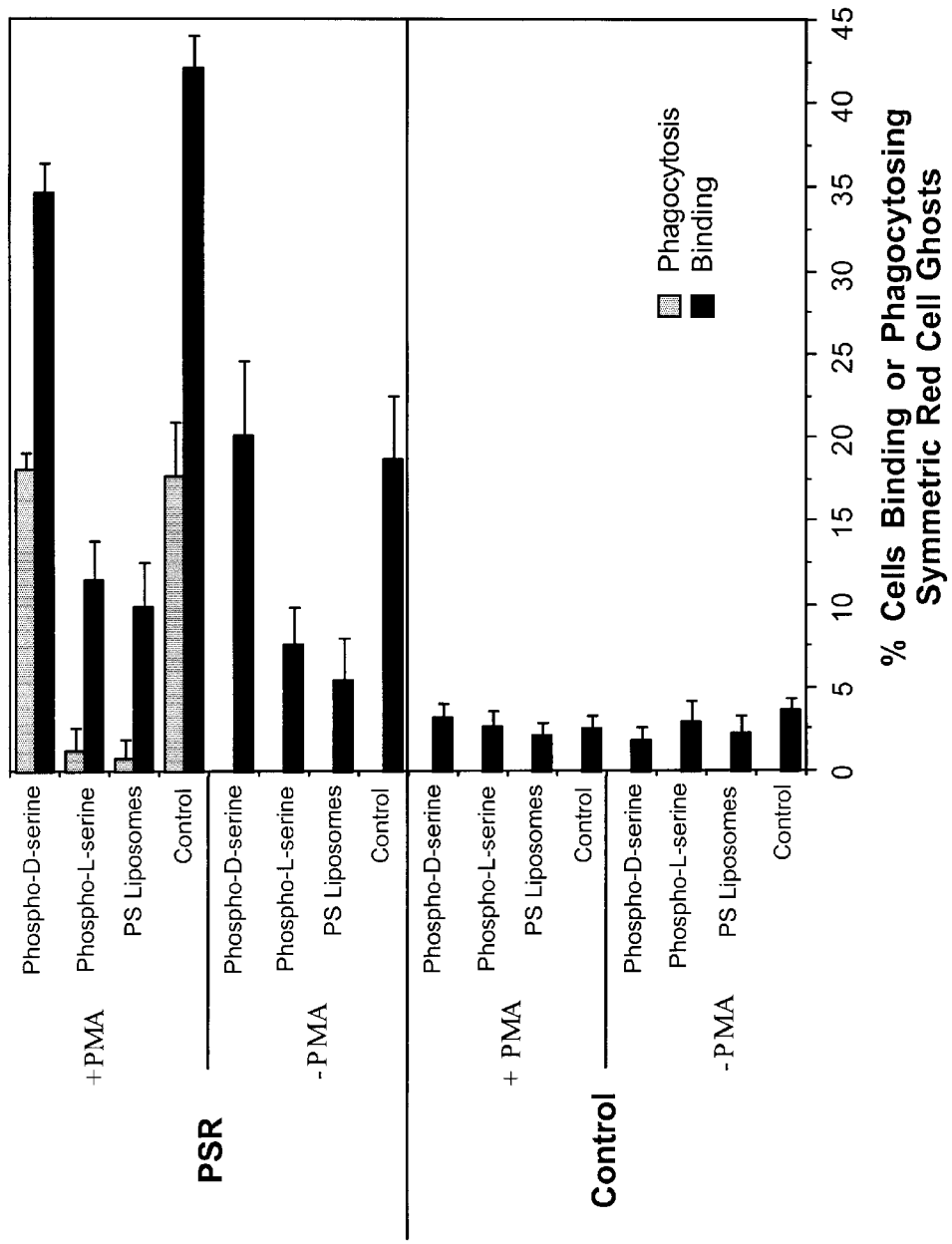
FIG. 5 is a bar graph showing that binding and phagocytosis of symmetric red cell ghosts by Jurkat T cells stably transfected with candidate PSR is inhibited stereospecifically by phospho-L-serine and not phospho-D-serine.

The stable Jurkat T cells reliably bound to apoptotic cells only when PS receptor expression was induced with PMA (FIG. 4C). mAb 217 and PS inhibited binding, whereas control IgM and other anionic phospholipids did not (FIG. 4C). These results exactly recapitulated the present inventors' previous observations with macrophages that recognize PS (Fadok et al., *J Immunol* 148:2207–2216 (1992); Fadok et al., *J Immunol* 161:6250–6257 (1998)). In addition, 5.8+/−1.2% of the stably transfected cells phagocytosed apoptotic cells; phagocytosis was never observed in Jurkat cells transfected with the control plasmid (e.g., FIG. 4C). It was also observed that Jurkat T cells transfected with the candidate PSR could bind to symmetric red cell ghosts, and that binding was inhibited by PS liposomes and by phospho-L-serine, not phospho-D-serine, showing the same stereospecificity seen with macrophages (FIG. 5). If, however, the transfectants were pretreated with PMA to increase surface expression of the receptor, their ability to bind symmetric red cells was increased and they engulfed them as well.

Figure 6B:
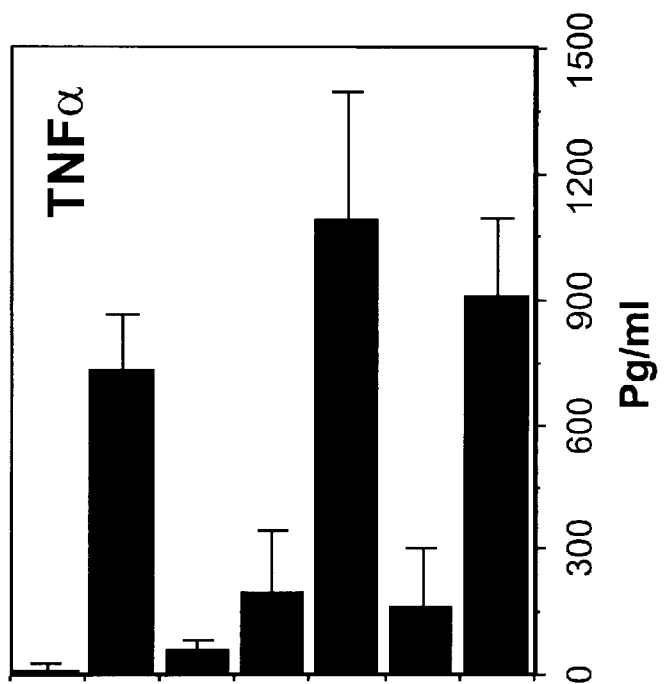
FIGS. 6A–6B are bar graphs showing that treatment of J774 mouse macrophages with mAb 217, PS-containing liposomes, or apoptotic cells stimulates TGFβ secretion and inhibits LPS-induced TNFα production.
Figure 6A:
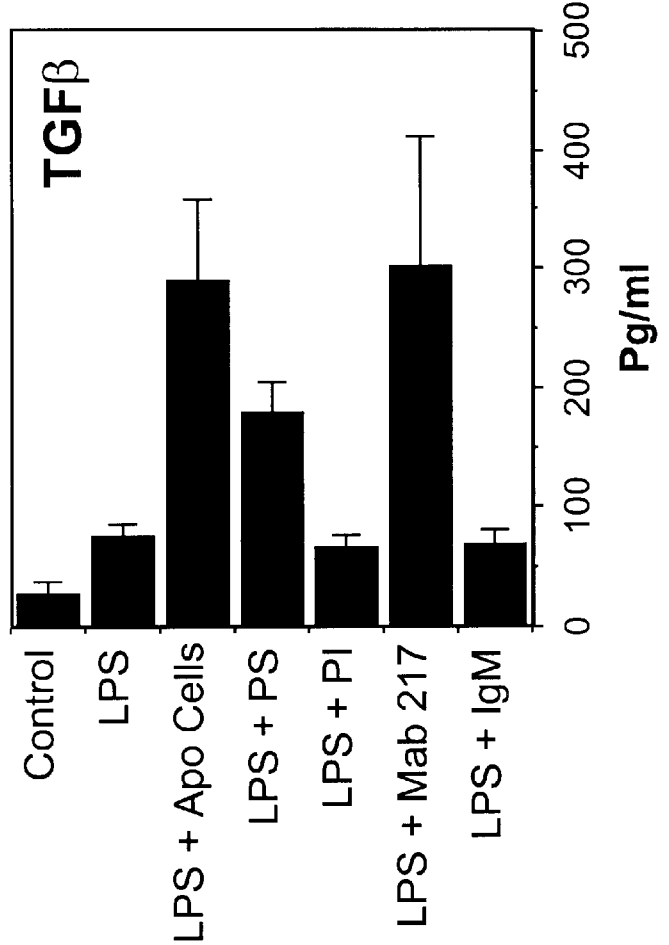

Uptake of apoptotic cells by macrophages is associated with the production of TGFβ and the down regulation of inflammatory cytokines (Fadok et al., *J Clin Invest* 101:890–898 (1998); McDonald et al., *J Immunol.* 163:6164–6172 (1999)). Because phosphatidylserine has been shown to downregulate several macrophage functions, including TNFα production (Aramaki et al., *Biochem Biophys Res Commun* 231:827–830 (1997)), it was important to determine if the candidate PS receptor could provide the signal for this cytokine response. PS-containing liposomes and mAb 217 stimulated TGFβ and decreased TNFα production in LPS-stimulated J774 macrophages (FIGS. 6A and 6B), suggesting that the candidate PS receptor plays an important role in the down regulation of inflammatory responses following uptake of apoptotic cells by macrophages. TGFβ induced by macrophage uptake of apoptotic cells was recently shown to promote intracellular growth of trypanosomes (Freire-de-Lima et al., *Nature* 403:199–203 (2000)). This antibody was also able to stimulate TGFβ production from NIH3T3 cells; their engulfment of apoptotic cells was inhibited by PS and by mAb 217 (data not shown).

Of great interest is the observation that there is high homology between the mammalian protein and genes of unknown function in *C. elegans* and *Drosophila melanogaster*, implying that PS recognition may have been preserved across phylogeny. Three of the 6 genes known to be involved in phagocytosis of apoptotic bodies in *C. elegans* are homologous to mammalian proteins (Wu et al., *Nature* 392:501–504 (1998); Wu et al., *Cell* 93:951–960 (1998); Liu et al., *Cell* 93:961–972 (1998)), suggesting that the basic machinery mediating phagocytosis may be conserved in most multicellular organisms. Clearance of apoptotic bodies is also a feature of apoptotic cell death in Drosophila (Franc et al., *Science* 284:1991–1994 (1999)). For example, croquemort, a homologue of mammalian CD36, has been shown to play a critical role (Franc et al., ibid.). It will be important to determine if the PS receptor of the present invention also mediates uptake in Drosophila and *C. elegans*.

Based on the data shown here, the present inventors propose that the gene product described in this example is a PS-specific receptor, and that this protein is critical in mediating uptake of apoptotic cells and the anti-inflammatory effects of clearance in mammals.

Materials and Methods
Cells and Cell Lines

Human monocytes were obtained from normal donors, and cultured in X-Vivo 10 (BioWhitaker) containing 10% human serum. The differentiated macrophages (HMDM) were used at 7 days of culture. Mouse bone-marrow derived macrophages were derived by culturing bone marrow cells in M-CSF for 5–7 days.

Development of Monoclonal Antibodies

HMDM stimulated to induce PS receptor expression (Fadok et al., *J Immunol* 161:6250–6257 (1998)) were injected 4× at monthly intervals intraperitoneally into BALB/c mice. The sera was tested for ability to bind at higher titre to stimulated vs unstimulated HMDM using whole cell ELISA. Supernatants resulting from the fusion were tested by whole cell ELISA using stimulated macrophages, by flow cytometry on unstimulated macrophages and stimulated macrophages preincubated or not with 100 μM of PS or PI liposomes (containing 50:50 molar ratios of PS or PI to PC) (Fadok et al., *J Immunol* 148:2207–2216 (1992)) for 30 minutes at 4° C. Two hybridoma supernatants (mAb 217, mAb 284, IgM, kappa chain) were found which bound at higher levels to stimulated macrophages and which were inhibited from binding by PS liposomes, but not PI or PC liposomes.

Flow Cytometry, Cell Sorting, Fluorescence Microscopy

Approximately $0.51 \times 10^6$ cells were incubated in 100 μl of HBSS containing 2% FCS and 100 μl of hybridoma supernatant. Isotype controls included anti-CD15s (PharMingen, San Diego, Calif.), a mouse IgM which bound at high levels to human macrophages, and mouse myeloma IgM (Calbiochem, San Diego). The secondary antibody was Cy-3 conjugated goat anti-mouse IgM, mu chain-specific (F(ab')2, Jackson Immunoresearch Laboratories, West Grove, Pa.). Stained cells were analyzed using a Becton-Dickson Facs-CAN cytometer. Data were analyzed using PCLysis software. For the transfected cells, purified mAb 217 was used as the primary reagent at 100 μg/ml. Adherent cells were prepared for flow cytometry by harvesting at 4° C. in Hank's BSS containing 5 mM EDTA for 15 minutes, followed by gentle scraping. Trypsin was not used, as it removed the antigen from the cell surface. Transiently transfected M12.C3 were sorted into mAb 217 positive or negative using the Mo-Flow cell sorter. For fluorescence microscopy, 3T3 cells were given apoptotic Jurkat T cells, fixed with 2% paraformaldehyde/15% sucrose in PBS, blocked with 10% goat serum overnight, stained with mAb 217 (100 μg/ml), followed by 1:500 dilution of Cy-3 goat anti-mouse IgM, 1:50 Alexa 488 phalloidin (Molecular Probes, Eugene, Oreg.), and 2.5 mg/ml DAPI to stain the nuclei.

Western Blot

Cells were lysed in 50 mM Tris (pH 7.4) containing 150 mM NaCl, 1% Triton-X 100, 0.25% deoxycholate, and a protease inhibitor cocktail (Sigma, St. Louis, Mo., AEBSF, pepstatin A, E-64, bestatin, leupeptin, aprotinin), proteins separated by SDS-PAGE, and transferred to nitrocellulose. The membranes were blocked with 5% dried milk, incubated with mAb 217 at 3 μg/ml overnight at 4° C., treated with peroxidase-labeled goat anti-mouse mu chain-specific $F(ab')^2$ for one hour (Jackson Immunoresearch, West Grove, Pa.), and developed by chemiluminescence (ECL, Amersham Pharmacia Biotech, Piscataway, N.J.).

Cloning of the Receptor

A directional cDNA library was made using the T7 Select system available from Novagen (Madison, Wis.). First, mRNA was isolated from J774 cells using Fast-Track (Invitrogen, Carlsbad, Calif.). cDNA was generated using directional HindIII random primers (Novagen, Madison, Wis.) by reverse transcription using MMLV reverse transcriptase. The ends were flushed with T4 DNA polymerase and directional Eco RI/Hind III linkers added. The sample was digested with Eco RI and HindIII and ligated into the T7 Select 1–1b vector (Novagen), then was amplified using the plate lysate amplification method recommended for this system. Sixty mm dishes were coated with purified mAb 217, an IgM control (anti-TNP, Pharmingen), or BSA, and blocked with 1% BSA and 5% dry milk. Viral lysates (2 ml) were added to the plates, incubated at room temp for 2 hours, then thoroughly washed with TBST. The bound virus particles were removed using 1% SDS, and 250 μl was added to 50 mls of the bacterial host strain (BLT5615) for lysis again. Lysis was seen only from material biopanned from plates coated with mAb 217; materials from plates coated with nonspecific IgM or BSA were not lytic. Following 5 rounds of biopanning, plaques were isolated and 12 were selected for sequencing using the ABI PRISM dRhodamine cycle sequencing system (PE Biosystems). Sequences were analyzed and aligned using MacVector 6.0 (Oxford Molecular Group); six were identical. Digoxigenin-labeled probes (DIG System, Boehringer Mannheim) were made from the 6 identical sequences and used to probe mRNA derived from J774 cells by Northern analysis. A 2 kb band was observed, confirming that the clones were derived from J774.

The full mouse sequence was obtained by aligning multiple entries in the mouse EST databases (GenBank). The sequence for the human homologue KIAA 0585 (Nagase et al., *DNA Res.* 5:31–39 (1998)) was available in GenBank (Accession No. ABO11157). The *C. elegans* homologue can be found in cosmid F29B9 (U70849.1) as Accession No. AAB09116. The complete sequence of the *Drosophila melanogaster* homologue was determined by sequencing a cDNA clone L0022859, whose partial sequence was already known (GenBank Accession No. AA940716). The clone was obtained from the Berkeley Drosophila Genome Project (BDGP/HHMI EST project) and Research Genetics.

Transfection of M12.C3 and Jurkat T cells

A human EST clone (Accession No. R24727) containing the full length gene was obtained through the IMAGE Consortium via ATCC (Manassas, Va.). The insert was subcloned into pcDNA 3.1/neo at Hind III/Not I sites (Invitrogen, Carlsbad, Calif.). M12.C3 cells were transfected in OptiMEM I medium using Lipofectamine Plus (both from GibcoBRL Life Science Technologies, Grand Island, N.Y.). Jurkat T cells were transfected in OptiMEM I medium using DMRIE C Jurkat T cells were stimulated with PHA alone (1 $\mu$g/ml) or with PMA (1.6 nM) and PHA to induce expression of the receptor. After 48 hrs, the cells were analyzed for expression of the PS receptor using mAb 217 and flow cytometry. For stable transfections, Jurkat T cells were selected in G418 (1 mg/ml). Surface expression of the receptor was induced by treatment of the stably transfected cells with 160 nM PMA in the absence of G418 for 48 hours. The candidate PSR was also inserted into pRc/RSV (PharMingen, San Diego, Calif.), or pUP (provided by Brian Schaefer), and transfected into Jurkat T cells or M12.C3 cells by electroporation.

Binding and Phagocytosis of Apoptotic Cells

Macrophages, fibroblasts, or epithelial cells were preincubated with 100 $\mu$M liposomes (containing 50:50 molar ratio of PS:PC or PI:PC), 1 mM RGDS or RGES, undiluted hybridoma supernatants containing mAb 217 or mAb 284 (for HMDM) or 100 $\mu$g/ml purified mAb 217, or 100 $\mu$g/ml isotype controls for 30 minutes prior to adding apoptotic Jurkat T cells at ratio of 5:1 target:phagocyte. Apoptosis was induced in Jurkat T cell by UV irradiation as described (Fadok et al., *J Clin Invest* 101:890–898 (1998)). THP-1 cells were stimulatedwith PMA (160 nM) for 72 hours to induce a macrophage phenotype, the ability to adhere, and the ability to take up apoptotic cells. After 1 hr, the phagocytes were washed and fixed for light microscopic evaluation of uptake. Apoptotic Jurkat T cells, HL-60 cells, or human neutrophils (induced by UV irradiation) (Fadok et al., ibid.; McDonald et al., 1999, supra) were added to the transfected M12.C3 or Jurkat T cells at ratio of 5:1 target to transfectant and incubated for 1 hour to assess binding in the presence or absence of mAb 217 (100–200 $\mu$g/ml), IgM controls (100–200 $\mu$g/ml), or 100 $\mu$M liposomes containing PC, or 50:50 molar ratios of PS:PC, PI:PC, or PG:PC (all phospholipids obtained from Avanti Polar Lipids, Alabaster, Ala.). Aliquots were removed and assessed for binding and phagocytosis by light microscopy as described (Fadok et al., *J Immunol* 148:2207–2216 (1992); Fadok et al., *J Immunol* 149:4029–4035 (1992); Fadok et al., *J Immunol* 151:4274–4285 (1993); Fadok et al., *J Immunol* 161:6250–6257 (1998)). For phagocytosis, the stably transfected Jurkat T cells were immobilized on glass slides treated with poly-L-lysine (100 $\mu$g/ml). Apoptotic cells were added for 2 hrs, then the slides were washed, fixed with methanol and stained with a modified Wright's Giemsa stain.

Binding and Phagocytosis of Symmetric Red Cell Ghosts

Human red blood cells were lysed in 1:50 PBS containing 1 mM $CaCl_2$ on ice for one hour; they were resealed at 37° C. for 30 minutes by addition of 5×PBS. Exposure of phosphatidylserine was confirmed by binding of annexin-FITC, assessed by flow cytometry.

Cytokine Analysis

J774 cells were treated with 10 ng/ml LPS in X-Vivo 10 medium and either apoptotic Jurkat T cells, 100 $\mu$M liposomes containing 50 molar % PS or PI, 100 $\mu$g/ml mAb 217, or 100 $\mu$g/ml mouse IgM isotype control added. Supernatants were evaluated for cytokine production by ELISA 18 hours later (Fadok et al., *J Clin Invest* 101:890–898 (1998)). 3T3 fibroblasts were treated with mAb 217 or isotype control and assessed for TGF$\beta$ production 18 hours later.

Statistical Analysis

Statistical analysis (ANOVA and Tukey-Kramer HSD) was performed using JMP software (SAS Institute, Inc., Cary, N.C.).

Example 2

This example demonstrates that the PS receptor of the present invention is present on all resident peritoneal macrophages harvested from mice and from at least 30% of freshly isolated mouse alveolar macrophages.

Resident peritoneal macrophages were collected by lavaging the abdominal cavity of euthanized mice with 10 ml Hank*s balanced salt solution. Resident alveolar macrophages were collected by lavaging the lungs of mice with 1 ml Hank's balanced salt solution. The lavage was repeated 2–3× per mouse. The cells were washed twice and suspended in staining buffer (Hank's balanced salt solution containing 2% fetal calf serum) for flow cytometric analysis using mAb 217 for assessment of PS receptor expression. The results demonstrated that the PS receptor of the present invention (as indicated by the ability to bind to mAb 217) is present on all resident peritoneal macrophages harvested from mice and from at least 30% of freshly isolated mouse alveolar macrophages (data not shown).

Example 3

This example demonstrates that 3T3 fibroblasts, primary mammary epithelial cells, and lymphocytes transfected with the PS receptor respond to treatment with mAb 217 by releasing TGF$\beta$.

Figure 7:
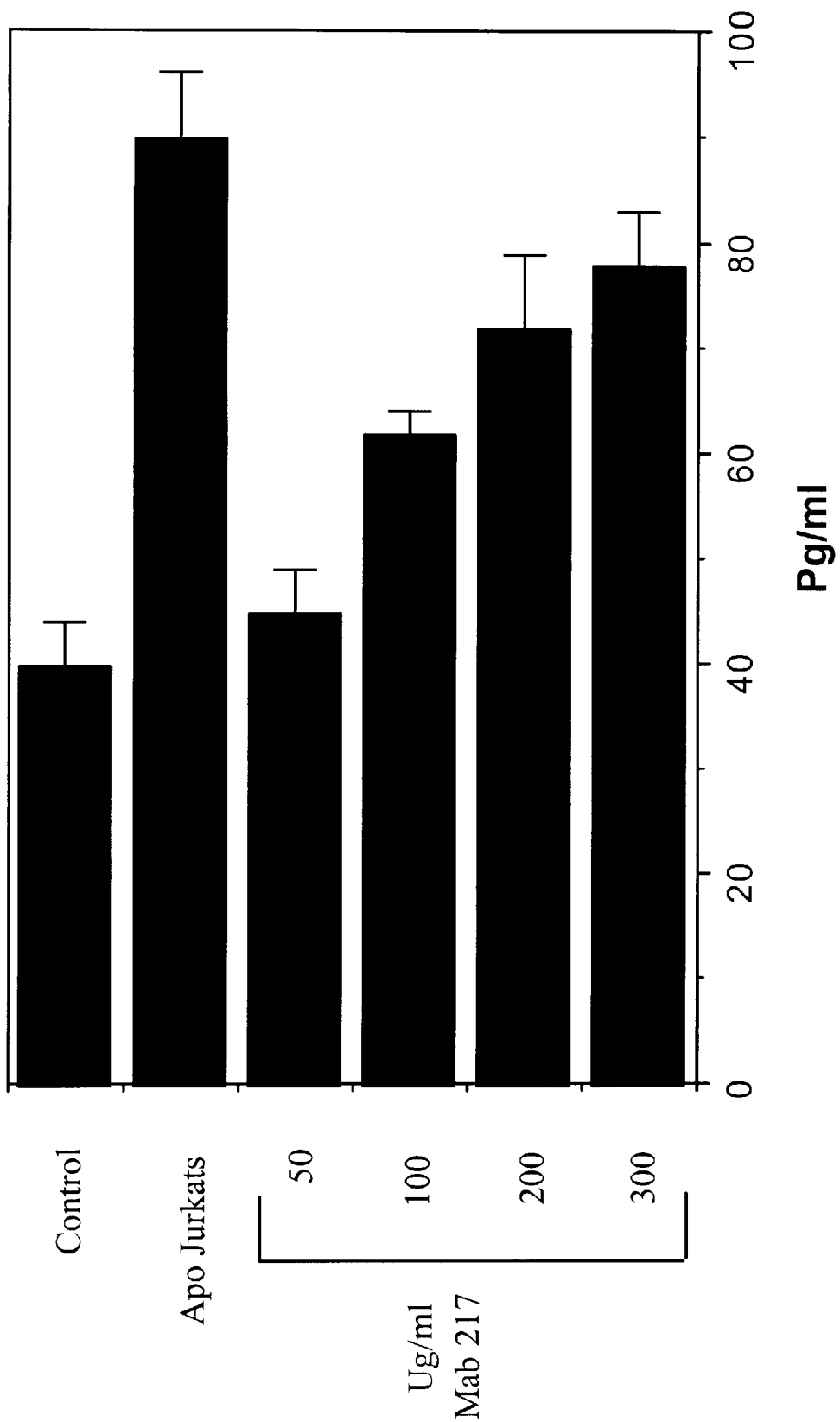
FIG. 7 is a bar graph showing that treatment of 3T3 fibroblasts with mAb 217 induces TGFβ secretion.
Figure 8:
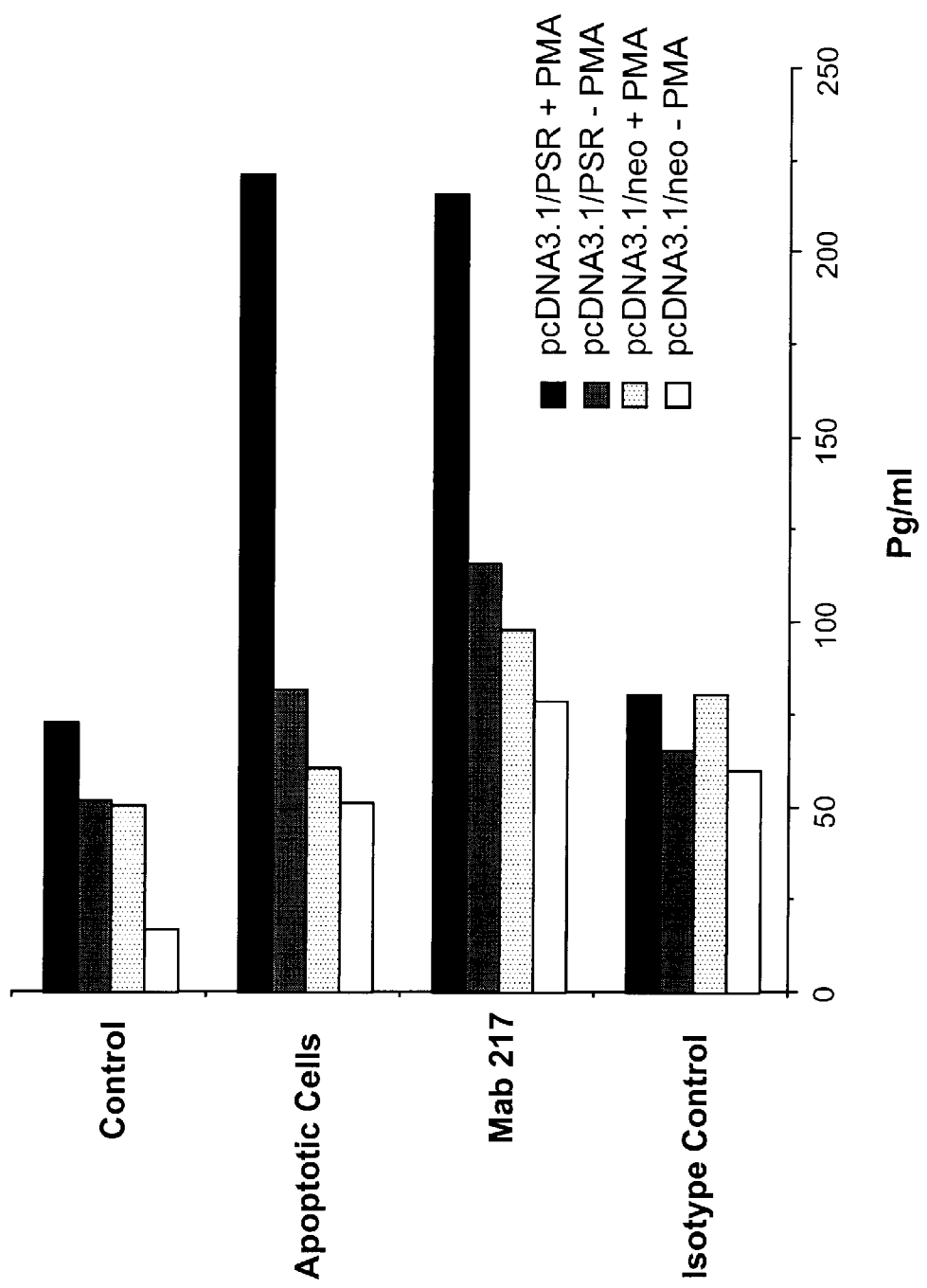
FIG. 8 is a bar graph showing that lymphocytes transfected with the PS receptor of the present invention can be triggered to release TGFβ by treatment with mAb 217 (200 μg/ml).

NIH 3T3 fibroblasts were plated, and cultured overnight so that the final confluency was 30–40%. Primary mammary epithelial cells were obtained by harvesting mammary glands from day 15–16 pregnant mice. The glands were minced, digested in collagenase and trypsin, and the epithelial cells purified by differential centrifugation. They were plated in growth medium containing insulin and EGF, and cultured for 4–5 days prior to use. Jurkat T cells stably transfected with the PS receptor were treated with 160 nM PMA for 48 hours to upregulate surface expression of the PS receptor. Then, 200 $\mu$g/ml mAb 217 or an isotype control were added to all populations, and cells cultured overnight in X-Vivo (serum-free) medium. Supernatants were collected, centrifuged to remove particulate debris, and frozen at −70° C. TGF$\beta$ levels were assessed by ELISA. FIGS. 7 and 8 show that 3T3 fibroblasts (FIG. 7), primary mammary epithelial cells (not shown), and lymphocytes transfected with the PS receptor (FIG. 8) respond to treatment with mAb 217 by releasing TGF$\beta$, which mimics their response to uptake of apoptotic cells.

Example 4

This example demonstrates that instillation of apoptotic cells into the lung and peritoneum of normal mice induces a rapid release of TGF$\beta$.

Either Jurkat T cells (which express phosphatidylserine externally during apoptosis) or undifferentiated PLB 985 cells (which do not express phosphatidylserine externally during apoptosis) (Fadok et al., 2000, *J. Biol. Chem.* 276:1071–1077) were treated with UV irradiation to induce apoptosis, then cultured for 2 hours. The cells were harvested and suspended in sterile Hank's balanced salt solution. Mice were anesthetized with Avertin, then the tracheas were cannulated. Apoptotic cells were subsequently instilled and the lungs lavaged one hour later with Hank's balanced salt solution. Bronchoalveolar lavage fluids were collected, centrifuged to remove particulate debris, then frozen at −70° C. TGFβ levels were assessed by ELISA. Results demonstrated that instillation of apoptotic cells into the lung and peritoneum of normal mice induces a rapid (detectable within 1 hour) release of TGFβ (data not shown).

Example 5

This example demonstrates that exposure of phosphatidylserine on apoptotic cells is required for engulfment by macrophages and fibroblasts.

Macrophages were generated by harvesting bone marrow from C3H/HeJ mice and culturing in DMEM containing 10% fetal calf serum and 10% L929 cell-conditioned medium as a source of macrophage-colony stimulating factor (M-CSF). NIH 3T3 cells were obtained from the American Type Tissue Culture Collection and cultured as recommended. To generate apoptotic cells, Jurkat T cells, HL-60 cells, or PLB 985 cells were irradiated with UV and cultured for two hours to induce apoptosis. Apoptosis was quantitated by morphological assessment using light microscopy; exposure of phosphatidylserine was assessed by flow cytometry using FITC-conjugated annexin V (see Fadok et al., 2000, J. Biol. Chem. 276:1071–1077). Jurkat T cells and HL-60 cells expose phosphatidylserine during apoptosis; PLB 985 cells do so poorly. The apoptotic populations were then added to macrophages or fibroblasts and engulfment assessed by light microscopy.

Figure 9A:
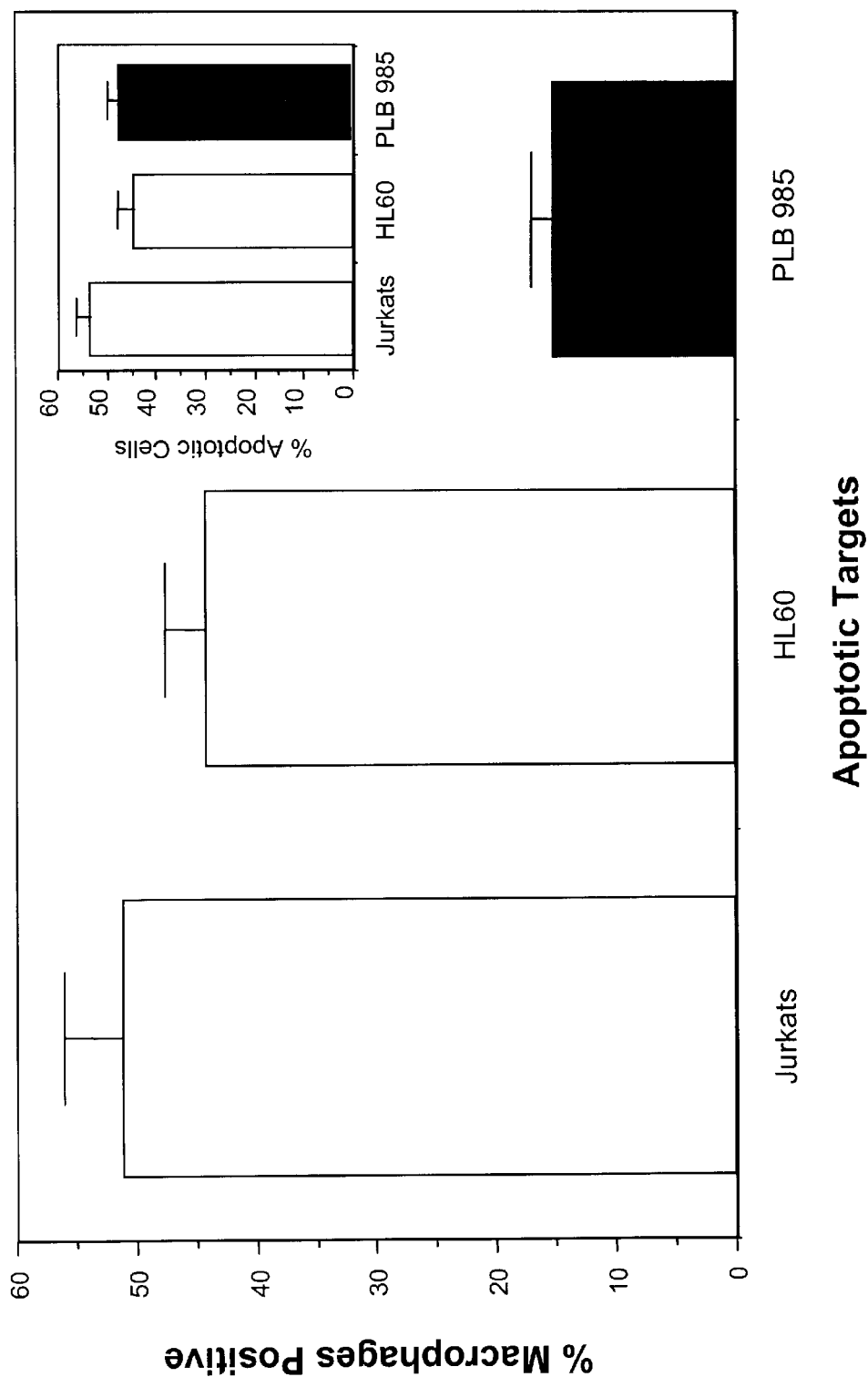
FIG. 9A is a bar graph showing that apoptotic cells that do not lose phospholipid asymmetry are recognized poorly by macrophages.

FIG. 9A shows that mouse bone marrow derived macrophages do not engulf apoptotic cells (undifferentiated PLB 985 cells) which express PS poorly. The Y-axis shows the percentage of macrophages that were positive for engulfed apoptotic cells. The inset bar graph shows the percentage of apoptosis as assessed by light microscopy for each of the apoptotic populations used.

Figure 9B:
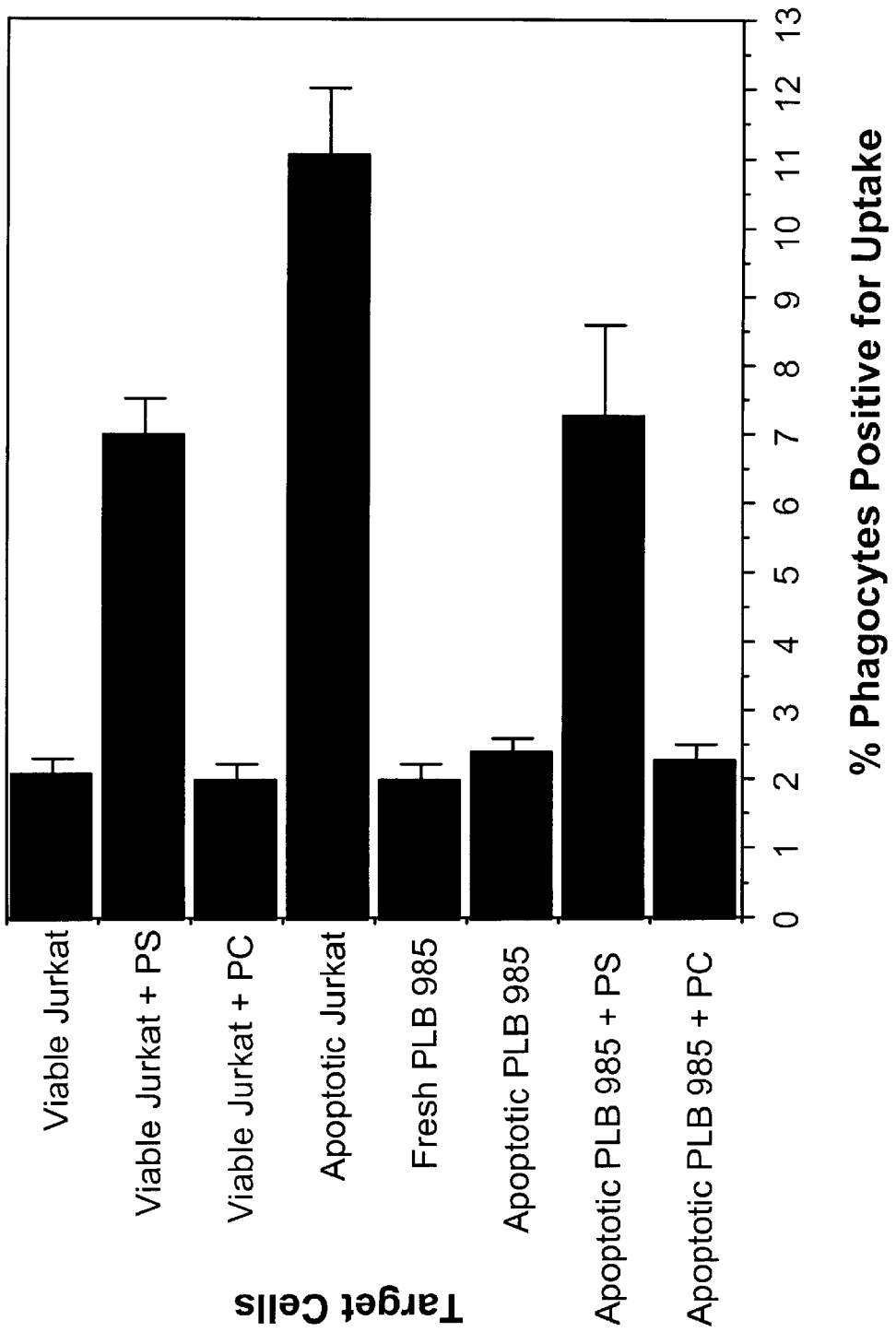
FIG. 9B is a bar graph showing that fibroblasts only ingest apoptotic cells that express PS externally.

FIG. 9B shows similar results when fibroblasts are used as the phagocyte. When phosphatidylserine is restored to the inner leaflet using liposome transfer, uptake by the fibroblasts is restored. Liposomes containing the control phospholipid, phosphatidylcholine, do not restore uptake. "Fresh" PLB 985 cells are viable, and therefore not recognized. Moreover, when phosphatidylserine is transferred to viable Jurkat T cells, they are recognized and engulfed.

Figure 9C:
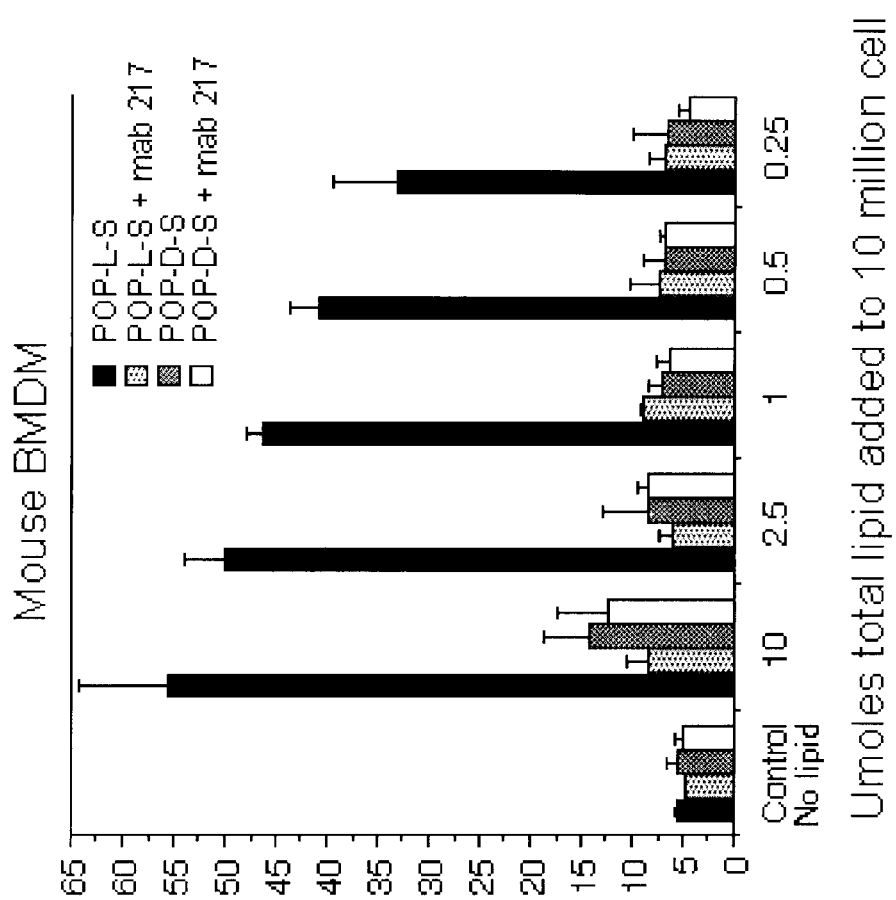
FIG. 9C is a bar graph showing that PLB cells are only recognized if PS is inserted by liposome transfer.

FIG. 9C shows that recognition of apoptotic PLB 985 cells is restored when the plasma membrane is reconstituted with PS by liposome transfer. Only physiological (L-stereoisomers) are effective at restoring recognition, and recognition is blocked by mAb 217 (Fadok et al., 2000, *J. Biol. Chem.* 276:1071–1077).

Example 6

This example demonstrates that the uptake of apoptotic cells is dependent on the PS receptor.

Figure 10:
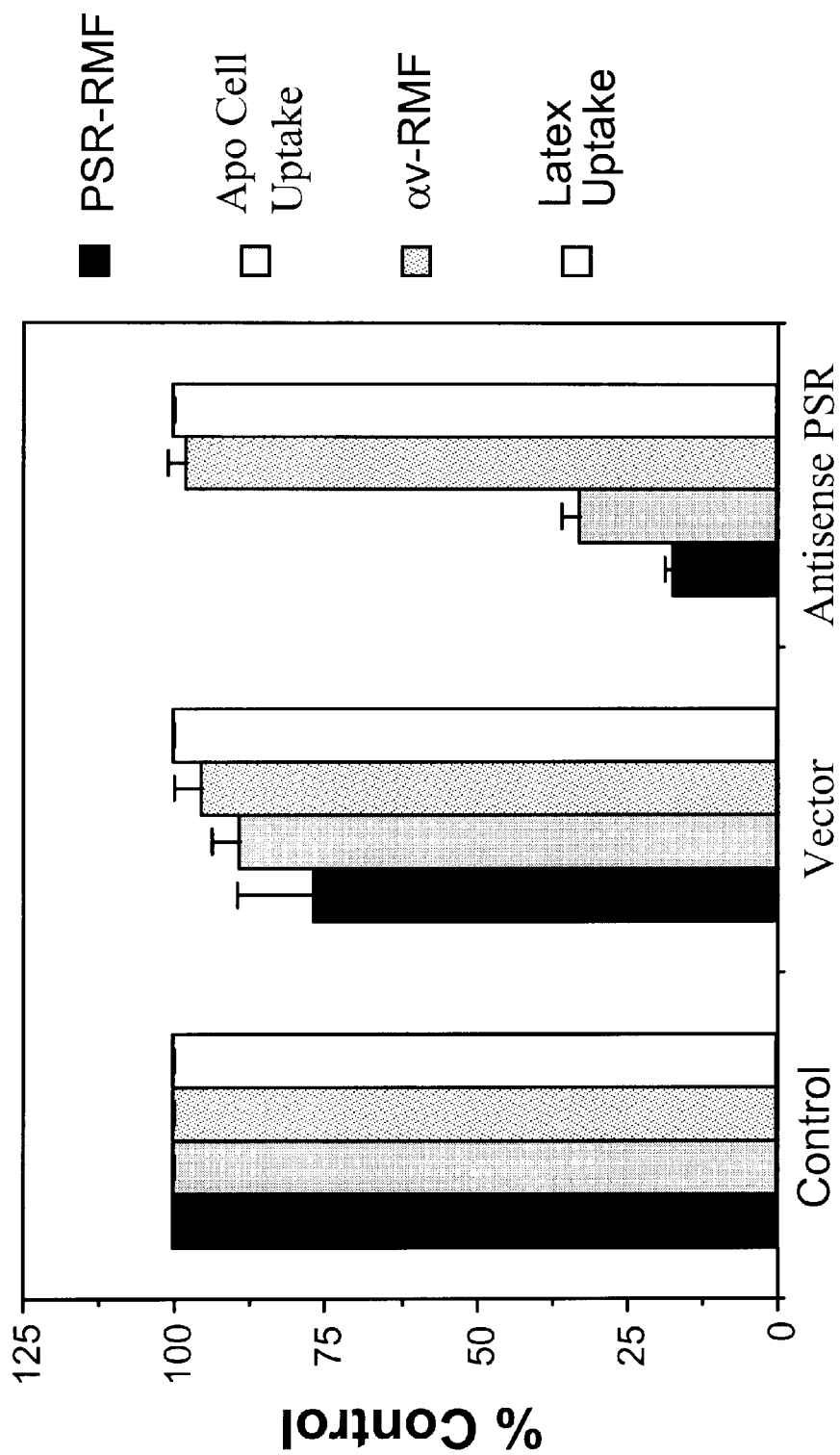
FIG. 10 is a bar graph showing the effects of PS receptor antisense on PSR expression and apoptotic cell uptake.

NIH 3T3 fibroblasts were transfected with pcDNA 3.1 (Invitrogen, Carlsbad, Calif.) containing the PS receptor in an antisense configuration (i.e., the full complementary nucleic acid sequence of SEQ ID NO:4) or with empty vector using lipofection. The cells were assessed for expression of the PS receptor by flow cytometry using mAb 217 (FIG. 10; PSR-RMF; RMF=relative mean fluorescence), and for uptake of apoptotic Jurkat T cells 18–24 hours after transfection (FIG. 10; Apo Cell Uptake). Effects of antisense on vitronectin receptor expression (FIG. 10; αv-RMF) and uptake of latex beads (FIG. 10; Latex Uptake) were assessed as controls. The results illustrated in FIG. 10 demonstrate that the transfection of PS receptor antisense significantly reduced both PSR expression and apoptotic cell uptake by the fibroblasts, as compared to controls. Transfection of the sense construct had no effect on receptor expression or apoptotic cell uptake.

Example 7

This example demonstrates that production of TGFβ in response to apoptotic cells is dependent on PS receptor.

Figure 11:
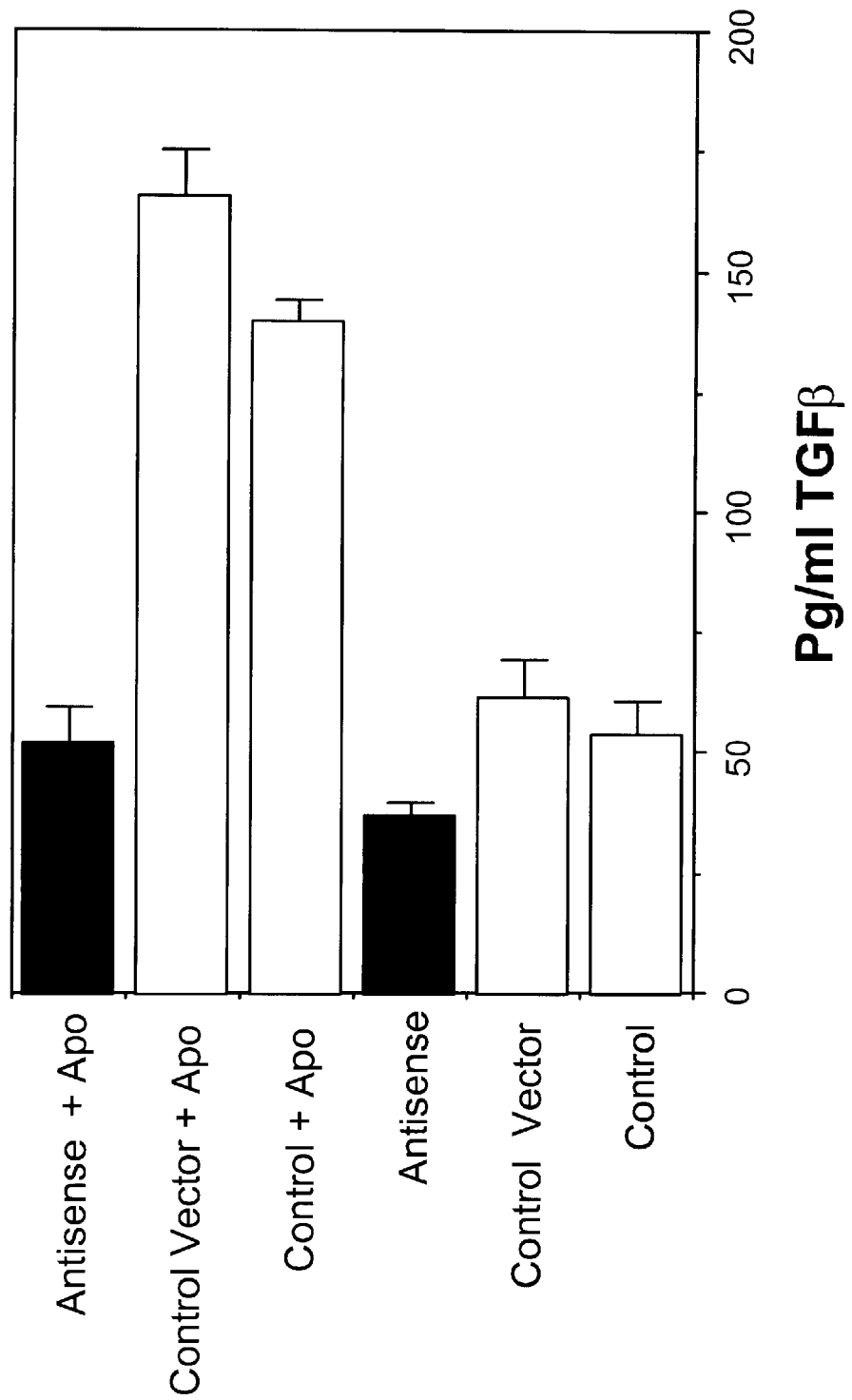
FIG. 11 is a bar graph showing the effects of PS receptor antisense on the TGFβ response to apoptotic cells.

NIH 3T3 fibroblasts were transfected with antisense as described for Example 6. Then, apoptotic Jurkat T cells were added 18–24 hours after transfection, and the cells cultured overnight. Supernatants were collected, centrifuged to remove particulate debris, and frozen at −70° C. TGFβ production was assessed by ELISA. The results shown in FIG. 11 demonstrate that PS receptor antisense significantly reduced the production of TGFβ by the transfected cells in response to apoptotic cells as compared to normal and empty vector controls.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated phosphatidylserine receptor protein selected from the group consisting of:
   a. a protein consisting essentially of an amino acid sequence spanning from a starting poaltion of one of amino acid residues from about 252–289 of SEQ ID NO:3 to an ending position of about amino acid residue 414 of SEQ ID No::3; and,
   b. a homologue of the protein of (a), wherein said homologue consists essentially of an amino acid sequence that is at least about 70% identical to said amino acid sequence of (a);

wherein said isolated phosphatidylserine receptor protein is a soluble phosphatidylserine receptor protein and has a phosphatidylserine receptor biological activity.

2. The isolated phosphatidylserine receptor protein of claim 1, wherein said protein consists essentially of an amino acid sequence spanning from a starting position of about amino acid residue 289 of SEQ ID NO:3 to an ending position of about amino acid residue 414 of SEQ ID NO:3.

3. The isolated phosphatidylserine receptor protein of claim 1, wherein said homologue is at least about 80% identical to said amino acid sequence of (a).

4. The isolated phosphatidylserine receptor protein of claim 1, wherein said homologue is at least about 90% identical to said amino acid sequence of (a).

5. The isolated phosphatidylserine receptor protein of claim 1, wherein said protein of (a) consists essentially of an amino acid sequence spanning from a starting position of one of amino acid residues 252–289 of SEQ ID NO:3 to an ending position of about amino acid residue 414 of SEQ ID NO:3.

6. A fusion protein comprising the protein of claim 1 operatively linked to a heterologous protein sequence.

7. A composition comprising at least about 1 μg of an isolated phosphatidylserine receptor protein selected from the group consisting of:
   a. an isolated phosphatidylserine receptor homologue comprising an amino acid sequence that is at least 316 amino acid residues in length, that is less than 100% identical to the amino acid sequence represented by SEQ ID NO:3, and that is at least about 70% identical to said the amino acid sequence represented by SEQ ID NO:3;
   b. a phosphatidylserine receotor protein consisting essentially of an amino acid sequence spanning from a starting position of one of amino acid residues from about 252–289 of SEQ ID NO:3 to an ending position of about amino acid residue 414 of SEQ ID NO:3, wherein said fragment is a soluble phosphatidylserine receptor protein; and
   c. a homologue of the fragment of (b), wherein said homologue consists essentially of an amino acid sequence that is at least about 70% identical to said amino acid sequence of (b);
   wherein said isolated phosphatidylserine receptor protein has a phosphatidylserine receptor biological activity.

8. The composition of claim 7, wherein said protein consists essentially of an amino acid sequence selected from the group consisting of:
   a. an isolated phosphatidylserine receptor homologue comprising an amino acid sequence that is at least 316 amino acid residues in length, that is less than 100% identical to the amino acid seciuence represented by SEQ ID NO:3, and that is at least about 70% identical to the amino acid sequence represented by SEQ ID NO:3; and
   b. a phosphatidylserine receptor protein comprising an amino acid sequence spanning from a starting position of one of amino acid residues from about 252–289 of SEQ ID NO:3 to an ending position of about amino acid residue 414 of SEQ ID NO:3, wherein said protein is a soluble phosphatidylserine receptor protein;
   wherein said protein has a phosphatidylserine receptor biological activity.

9. The composition of claim 7, wherein said homologue of (a) is less than about 100% identical to SEQ ID NO:3 and at least about 80% identical to SEQ ID NO:3.

10. The composition of claim 7, wherein said homologue of (a) is less than about 100% identical to SEQ ID NO:3 and at least about 90% identical to SEQ ID NO:3.

11. The composition of claim 7, wherein said homologue of (a) comprises at least about 25 contiguous amino acid residues of SEQ ID NO:3.

12. The composition of claim 7, wherein said homologue of (a) comprises at least about 100 contiguous amino acid residues of SEQ ID NO:3.

13. An isolated phosphatidylserine receptor homologue, wherein said homologue comprises an amino acid sequence that is:
   a. at least 316amino acids in length;
   b. at least about 70% identical to an amino acid sequence represented by SEQ ID NO:3; and,
   c. less than 100% identical to said amino acid sequence represented by SEQ ID NO:3;
   wherein said isolated phosphatidylserine receptor homologue has a phosphatidylserine receptor biologicalactivity.

14. The isolated phosphatidylserine receptor homologue of claim 13, wherein said amino acid sequence of said homologue differs from said amino acid sequence represented by SEQ ID NO:3 by at least one modification selected from the group consisting of an amino acid deletion, an amino acid insertion, and an amino acid substitution.

15. The isolated phosphatidylserine receptor homologue of claim 13, wherein said homologue is less than about 95% identical to said amino acid sequence represented by SEQ ID NO:3.

16. The isolated phosphatidylserine receptor homologue of claim 13, wherein said homologue is at least about 80% identical to an amino acid sequence represented by SEQ ID NO:3.

17. The isolated phosphatidylserine receptor homologue of claim 13, wherein said homologue is at least about 90% identical to an amino acid sequence represented by SEQ ID NO:3.

18. A method to identify a regulator of a phosphatidylserine receptor, comprising:
   a. contacting a phosphatidylserine receptor protein with a putative regulatory compound, wherein said phosphatidylserine receptor protein is selected from the group consisting of:
      i. a protein comprising an amino acid sequence represented by SEQ ID NO:3;
      ii. a homologue of the protein of (a), wherein said homologue comprises an amino acid sequence that is at least 316 amino acid residues in length and that is at least about 70% identical to said amino acid sequence of (a);
      iii. a protein consisting essentially of a fragment spanning from a starting position of one of amino acid residues from about 252-289 of SEQ ID NO:3 to an ending position of about amino acid residue 414 of SEQ ID NO:3, wherein said fragment is a soluble phosphatidylserine receptor protein; and,
      iv. a homologue of the protein of (iii), wherein said homologue comprises an amino acid sequence that is at least about 70% identical to said amino acid sequence of (iii);
   wherein said phosphatidylserine receptor protein has a phosphatidylserine receptor biological activity;
   b. detecting whether said putative regulatory compound binds to said receptor; and,
   c. detecting whether said putative regulatory compound increases or decreases activity of the receptor as compared to prior to contact with said compound;
   wherein compounds that bind to said receptor and increase or decrease activity of the receptor, as compared to a receptor in the absence of said compound, indicates that said putative regulatory compound is a regulator of said phosphatidylserine receptor.

19. The method of claim 18, wherein said step of detecting whether said putative regulatory compound increases or decreases activation of the receptor comprises the steps of contacting said receptor with a stimulator of said receptor and detecting whether activation of said receptor is increased or decreased in the presence of said putative regulatory compound as compared to in the absence of said putative regulatory compound.

20. The method of claim 18, wherein said method further comprises a step of detecting whether said putative regulatory compound regulates a biological activity of a cell that expresses the receptor, said biological activity being selected from the group consisting of iransforming growth factor β (TGFβ) production, prostaglandin E2 (PGE2) production, tumor necrosis factor α (TNFα) production, chemokine production, granulocyte-macrophage colony stimulating factor (GM-CSF) production, interleukin-1 (IL-1) production, phosphorylation of the receptor, and phagocytosis of apoptotic cells.

21. A composition comprising an isolated phosphatidylserine receptor protein selected from the group consisting of:
  a. an isolated phosphatidylserine receptor homologue comprising an amino acid sequence that is at least 316 amino acid residues in length, that is less than 100% identical to the amino acid sequence represented by SEQ ID NO :3, and that is at least about 70% identical to the amino acid sequence represented by SEQ ID NO:3;
  b. a phosphatidylserine receptor protein consisting essentially of an amino acid sequence spanning from a starting position of one of amino acid residues from about 252–289 of SEQ ID NO:3 to an ending position of about amino acid residue 414 of SEQ ID NO:3, wherein said fragment is a soluble phosphatidylserine receptor protein; and
  c. a homologue of the fragment of (b), wherein said homologue consists essentially of an amino acid sequence that is at least about 70% identical to said amino acid sequence of (b);

wherein said isolated, phosphatidylserine receptor protein has a phosphatidylserine receptor biological activity; and wherein at least about 80% weight/weight of total protein in said composition is said isolated phosphatidylserine receptor protein.

22. An isolated phosphatidylserine receptor protein selected from the group consisting of:
  a. a protein consisting of an amino acid sequence spanning from a starting position of one of amino acid residues from about 252-289 of SEQ ID NO:3 to an ending position of about amino acid residue 414 of SEQ ID NO:3; and,
  b. a homologue of the protein of (a), wherein said homologue consists of an amino acid sequence that is at least about 70% identical to said amino acid sequence of(a);

wherein said isolated phosphatidylserine receptor protein is a soluble phosphatidylserine receptor protein and has a phosphatidylserine receptor biological activity.

23. The isolated phosphatidylserine receptor protein of claim 22, wherein said protein consists of an amino acid sequence spanning from a starting position of about amino acid residue 289 of SEQ ID NO:3 to an ending position of about amino acid residue 414 of SEQ ID NQ:3.

24. The isolated phosphatidylserine receptor protein of claim 22, wherein said protein consists of an amino acid sequence spanning from a starting position of about amino acid residue 252 of SEQ ID NO:3 to an ending position of about amino acid residue 414 of SEQ ID NO:3.

* * * * *